(12) United States Patent
Xu et al.

(10) Patent No.: US 9,458,203 B2
(45) Date of Patent: Oct. 4, 2016

(54) INTEGRIN-BLOCKING POLYPEPTIDES AND USES THEREOF

(71) Applicant: Hanmei Xu, Nanjing (CN)

(72) Inventors: Hanmei Xu, Nanjing (CN); Chunyan Pu, Nanjing (CN); Zhian Kang, Nanjing (CN)

(73) Assignee: Hanmei Xu (CN)

( * ) Notice: Subject to any disclaimer, the term of this patent is extended or adjusted under 35 U.S.C. 154(b) by 0 days.

(21) Appl. No.: 14/368,960

(22) PCT Filed: Dec. 26, 2012

(86) PCT No.: PCT/CN2012/087465
§ 371 (c)(1),
(2) Date: Jun. 26, 2014

(87) PCT Pub. No.: WO2013/097709
PCT Pub. Date: Jul. 4, 2013

(65) Prior Publication Data
US 2014/0316106 A1    Oct. 23, 2014

(30) Foreign Application Priority Data

Dec. 27, 2011  (CN) .......................... 2011 1 0443052

(51) Int. Cl.
| | |
|---|---|
| *A61K 38/16* | (2006.01) |
| *C07K 14/00* | (2006.01) |
| *A61P 35/00* | (2006.01) |
| *A61K 38/39* | (2006.01) |
| *C07K 14/78* | (2006.01) |
| *C07K 7/06* | (2006.01) |

(52) U.S. Cl.
CPC ............. *C07K 14/001* (2013.01); *A61K 38/39* (2013.01); *C07K 7/06* (2013.01); *C07K 14/00* (2013.01); *C07K 14/78* (2013.01)

(58) Field of Classification Search
CPC ........ C07K 14/78; C07K 7/06; C07K 14/00; C07K 14/001; A61K 38/39
See application file for complete search history.

(56) References Cited

FOREIGN PATENT DOCUMENTS

| CN | 1827640 A | * | 9/2006 | ............. C07K 14/00 |
| CN | 1876186 A | * | 12/2006 | ............. A61P 27/02 |

OTHER PUBLICATIONS

Machine translation of CN 1827640 A, pp. 1-22, accessed Jul. 30, 2014.*
Pu et al, RGD-modified endostatin fragments showed an antitumor effect through antiangiogenesis, Anti-Cancer Drugs, 2012, 23, pp. 788-802, published on Sep. 2012.*
Machine translation of CN 1827640 A, pp. 1-58, accessed Jul. 7, 2015.*
Machine translation of CN 1876186 A, pp. 1-13, accessed Jul. 7, 2015.*
Lateef et al, An Improved Protocol for Coupling Synthetic Peptides to Carrier Proteins for Antibody Production Using DMF to Solubilize Peptides, Journal of Biomolecular Techniques, 2007, 18, pp. 173-176.*
Human Endostatin, from https://www.peprotech.com/en-US/Pages/Product/150-01, p. 1, accessed Dec. 9, 2015.*
Rehn et al, Interaction of endostatin with integrins implicated in angiogenesis, PNAS, 2001, 98, pp. 1024-1029.*

* cited by examiner

*Primary Examiner* — Julie Ha
*Assistant Examiner* — Li Ni Komatsu
(74) *Attorney, Agent, or Firm* — Schmeiser, Olsen & Watts, LLP

(57) ABSTRACT

A series of integrin blockers that present strong angiogenesis inhibiting performance, high integrin affinity and integrin-bonding capacity is provided. This series of integrin blockers can be adopted in treatment of solid tumors and rheumatoid arthritis. Specifically, said series of integrin blockers include polypeptide I, polypeptide II and polypeptide III (see SEQ ID NO: 1, SEQ ID NO: 2 and SEQ ID NO: 3) that can be adopted in treatment of solid tumors and rheumatoid arthritis. This invention also relates to application of these three integrin-blocking polypeptides in preparation of anti-tumor drugs, wherein the tumors that can be treated include those primary or secondary cancers originated from head and neck region or other organs such as brain, thyroid, esophagus, pancreas, lung, liver, stomach, breast, kidney, gallbladder, colon, rectum, ovary, cervix, uterus, prostate, bladder and testicle, as well as melanoma and sarcomas.

6 Claims, 2 Drawing Sheets

INTEGRIN-BLOCKING POLYPEPTIDES AND USES THEREOF

CROSS-REFERENCE TO RELATED APPLICATIONS

Figure 1:

This application claims priority to PCT Application No. PCT/CN2012/087465, having a filing date of Dec. 26, 2012, based off of CN Application No. 201110443052.2 having a filing date of Dec. 27, 2011, the entire contents of which are hereby incorporated by reference.

FIELD OF TECHNOLOGY

This follows relates to the pharmaceutical field, specifically to a series of integrin blockers that present strong angiogenesis-inhibiting performance, high integrin affinity and integrin-bonding capacity. This series of integrin blockers include two polypeptides and can be adopted in treatment of solid tumors and rheumatoid arthritis.

BACKGROUND

Unlimited proliferation, infiltration and metastasis constitute the characteristics of a malignant tumor, and also the major reasons leading to failed treatment and death. Therefore, effective control of proliferation, infiltration and metastasis is the essential measure to improve prognosis and survival rate of tumor-bearing patients. In 1971, Folkman firstly pointed out that the growth of tumor relies on angiogenesis, which is the morphological basis for tumor proliferation and metastasis in that it not only provides nutrition required for tumor growth, but also transfers numerous tumor cells to the host's other organs and consequently results in metastasis. Most of malignant solid tumors, such as ovarian cancer, liver cancer, cervical cancer and breast cancer, are angiogenesis-dependent. As the new blood vessels formed through angiogenesis can on the one hand provide nutrition and oxygen for the tumor, and on the other hand act as important channel for tumor metastasis, inhibiting the process of angiogenesis is one of the most important measures to fight against cancer.

Integrins are a type of receptors widely found on the cell surface. They can induce adhesion of vascular endothelial cells and tumor cells, and facilitate angiogenesis and tumor metastasis by means of mediating interaction between intracelluar cytoskeletal proteins and extracellular matrix molecules. Currently, at least 8 integrins (α1β1, α2β1, α3β1, α6β1, α6β4, α5β1, αvβ3, αvβ5) have been found closely related to tumor angiogenesis, among them αvβ3 being the most important. Integrin αvβ3 is also called VN receptor. It is a transmembrane heterodimer glycoprotein consisting of an αv subunit (CD51, 150 kD) and a β3 subunit (CD61, 105 kD). Integrin αvβ3 is expressed in many cell types and can combine with a variety of ligands during multicellular activities; therefore, it is extensively involved in tumor angiogenesis, infiltration and metastasis. It has been found that integrin αvβ3 can recognize the sequence Arg-Gly-Asp (RGD) in its ligands, which means that an RGD-containing polypeptide can function as an integrin antagonist and inhibit angiogenesis by means of reducing the expression of adhered molecules on the cell surface and mediating intracellular signal transduction. This eventually slows down tumor growth and metastasis. In other words, integrin-targeting polypeptides can block intracellular signaling pathways downstream of the integrin and effectively inhibit tumor growth and metastasis by means of slowing down angiogenesis. These features provide integrin-targeting polypeptides very promising prospects in tumor treatment.

Currently, some integrin blockers have been developed out on the international market and are undergoing the phase II clinical trial. However, no such products are seen on the Chinese market. It is of great necessity to develop this type of drugs with China's independent intellectual property. The Chinese patent "Angiogenesis-inhibiting Polypeptides and Preparation and Application Thereof"(ZL 200610039298 .2) disclosed a series of polypeptides obtained through restructuring and modifying the 6-49 amino acids on the integrin sequence. In contrast with endostatin, the restructured polypeptides present higher in vivo activity and tumor-targeting performance. In this cited patent, several integrin inhibitors were introduced, two of which were Arg-Gly-Asp-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Phe (SEQ ID NO: 4) (EDSM-1 for short) and Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Phe-Gly-Gly-Gly-Gly-Ala-Cys-Arg-Gly-Asp- Cys-Phe-Cys (SEQ ID NO: 5) (EDSM-2 for short,). Both of the sequences contain an integrin ligand sequence, consisting of Arg-Gly-Asp and Gly-Gly-Gly-Gly-Ala-Cys-Arg-Gly-Asp-Cys-Phe-Cys (SEQ ID NO: 6), and an angiogenesis-inhibiting sequence, namely, Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Phe (SEQ ID NO: 7). The above mentioned patent only conducted preliminary researches on cloning of polypeptides EDSM-1 and EDSM-2, construction of prokaryotically expressed vectors, and the application of EDSM-1 in treatment of liver cancer and gastric cancer. In contrast, the present invention, on the basis of further studies on the endostatin sequence, found out that the 6-48 amino acids on the integrin sequence demonstrate even better angiogenesis-inhibiting function, and then tried to modify this angiogenesis-inhibiting sequence, namely, Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Ala-Val-Gly-Leu-Ala-Gly-Thr-Phe- Arg-Ala (SEQ ID NO: 1), by adding an integrin ligand sequence (Arg-Gly-Asp-Gly-Gly-Gly-Gly) (SEQ ID NO: 14) to its N-terminal and C-terminal ends respectively. The modification results in two new integrin blockers, namely, polypeptide II (Arg-Gly-Asp-Gly-Gly-Gly-Gly-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg- Ala) (SEQ ID NO: 2) and polypeptide III (Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Gly-Gly-Gly-Gly-Arg-Gly-Asp) (SEQ ID NO: 3). These newly designed polypeptides, can on the one hand effectively bind to the integrin subtype specifically expressed by tumors as the RGD (Arg-Gly-Asp) sequence contained in the integrin ligand sequence can targetedly recognize the integrin, and on the other hand successfully inhibit tumor growth and metastasis by means of inhibiting the process of angiogenesis—a function realized by the angiogenesis-inhibiting sequence contained in them. Therefore, both polypeptide II and polypeptide III demonstrate strong tumor-targeting performance and high integrin affinity simultaneously. It has been found that they exhibit desirable therapeutic effect on many types of tumors, which means they have a wide range of indications and entail great social benefits and market potential.

Rheumatoid arthritis (RA) is one of the commonest autoimmune inflammatory arthropathies and major causes for disability. It is a chronic, symmetrical multi-synovial arthritis of unknown etiology. The incidence rate of RA is about 0.5%-1.0% throughout the world and about 0.4% in China. It can attack people at any age, but the risk goes higher with the increase of age. In addition, RA is closely related to gender, and the male to female incidence ratio is 1:3. The female at the age of 45-55 are at the highest risk. The initial symptoms of RA are progressive pain and swelling in hands and wrists, particularly the swelling at the back of wrists. Though such symptoms can be relieved with common symptomatic treatments, they tend to reappear repeatedly due to irregular or underdosed medication. With the development of the disease, progressive stiffness of joints may appear early in the morning and usually lasts for more than one hour, meanwhile, some joint dysfunctions may also appear.

As is mentioned above, the etiology and pathogenesis of RA remain unknown, and its basic pathological manifestations include vasculitis and synovitis. When RA attacks, a layer of pannus forms on the synovial membrane due to angiogenesis, which consequently results in thickening of synovial membrane, increase of exudate, release of various cytokines, cartilage destruction and bone erosion. It can also affect surrounding tissues, such as muscular compartments, ligaments, tendon sheaths and muscles, and finally affect the stability of joints and lead to joint deformation and disability. The RA vasculitis may attack other organs throughout the body and manifests itself as a systemic disease.

Currently, drugs for RA treatment can be categorized into two types: symptom-controlling drugs and disease-controlling drugs. The symptom-controlling drugs can be further divided into 4 groups: 1. NSAIDs, long regarded as first-line anti-RA agents; there are more than dozens of NSAIDs available on the Chinese market; 2. glucocorticoids, very good anti-inflammatory agents; but they cannot significantly improve the symptoms and will lead to many serious side effects if being used alone for a long time. They can be used, however, in the short term in moderate dose before the slow-onset agents take effect, and would be necessary to form combined medication with the second-line agents in pulse therapy of RA flare-ups, particularly for those patients with extra-articular manifestations; 3. slow-onset, anti-rheumatic drugs, usually regarded as second-line agents, including antimalarials, sodium aurothiomalate (gold), penicillamine and sulfasalazine; they take effect considerably slowly, but have positive functions in improving the overall condition of RA patients. They are also called disease-modifying antirheumatic drugs (DMARDs); 4. immunosuppressants, including methotrexate, cyclophosphamide, azathioprine, tripterygium and sinomenine, etc.

Angiogenesis is one of the main histological characteristics of rheumatoid arthritis. It causes hyperplasia of synovial membrane and infiltration of inflammatory cells—the basis for the formation of pannus and final destruction of joints. Due to angiogenesis, newly-formed blood vessels invade the joint cartilage, which under healthy conditions contains no blood vessels. The invasion of blood vessels leads to the erosion of cartilage, pain and eventually deformation of the whole joint. Also due to angiogenesis, the thickness of patients' synovial membrane increases. Normally, the inner layer of synovial membrane in a health people contains only 1-2 layers of cells; however, it would increase to 4-10 layers (sometimes 20 layers) of cells when RA attacks. These increased cells are not only in great quantity, but also extremely active. They can secrete a large quantity of cytokines, signaling molecules and proteases, all of which accelerate the process of joint destruction. In addition, there are a large quantity of inflammatory cells, such as T cells, B cells and monocytes infiltrating in the synovial membrane of RA patients.

Under normal physiological conditions, angiogenesis is strictly regulated and is a necessary process particularly important for reproduction, fetal development, tissue repair and wound healing. It also takes place under many pathological conditions, including growth and metastasis of tumors, inflammatory disorders such as RA, psoriasis, osteoarthritis, inflammatory bowel disease (IBD, including Crohn's disease and ulcerative colitis) and others.

Integrin $\alpha v\beta 3$ can recognize the Arg-Gly-Asp (RGD) sequence in ligand molecules and bind with a variety of ligands during the multicellular activities. These features enable it to participate in such tumor processes as angiogenesis, infiltration and metastasis as well as other physiological and pathological processes such as inflammation, wound healing, blood coagulation, etc. Therefore, polypeptides bearing the RGD sequence can function as integrin antagonists, and the RGD sequence can be adopted as a vector, targetedly delivering therapeutic polypeptides to the endothelium of newly generated blood vessels so that those angiogenesis-related diseases can be effectively treated. The RGD-bearing, angiogenesis-inhibiting polypeptides can not only block the pathways of oxygen and nutrients to the synovial membrane by inhibiting angiogenesis, but also directly lead to degeneration of blood vessels therein. Therefore, they can inhibit hyperplasia of synovial membrane of RA patients. In short, inhibition of angiogenesis is an essential step for treatment of RA, while the proliferation and migration of endothelial cells are two crucial mechanisms for angiogenesis.

The RGD (Arg-Gly-Asp) sequence contained in polypeptide II and polypeptide III enables these polypeptides to realize effective combination with integrins. Such a combination on the one hand inhibits the interaction between intracellular cytoskeletal proteins and extracellular matrix molecules, and on the other hand inhibits the cell—cell adhesion and the adhesion between cells and extracellular matrix. The intercellular signaling as well as signal transduction between cells and extracellular matrix are consequently blocked, and angiogenesis is therefore inhibited. Meanwhile, there also exists an angiogenesis-inhibiting sequence in the above mentioned polypeptides. Researchers have found that this sequence presents high effect in inhibiting angiogenesis—a feature bearing great significance in treatment of RA and other similar diseases. In short, Integrin-inhibiting polypeptides demonstrate desirable performance in treating RA by targeting at RA's angiogenesis process. This provides a new orientation for developing new anti-RA drugs.

The newly designed polypeptides disclosed in the present invention, namely, polypeptide II and polypeptide III, present strong integrin-targeting performance and high integrin affinity. The preliminary research has indicated that polypeptide II and polypeptide III can inhibit the proliferation and migration of endothelial cells as well as capillary formation; with flow cytometry analysis, it detected out that the function target of polypeptide II and polypeptide III is integrin $\alpha v\beta 3$. Later research also found out that polypeptide II and polypeptide III can inhibit the formation of capillary structures of rats' aortic rings, and with the cell adhesion assay, it further proved that the function target of the polypeptides is integrin αvβ3, and concluded that the polypeptides can be adopted in treatment of RA. These conclusions broaden the indication range of said polypeptides and highlight their social benefits and market potential.

SUMMARY

One aspect relates to verifying the therapeutic effect of a series of polypeptides, including polypeptide I, polypeptide II and polypeptide III, on solid tumors and RA, and to broaden the indication range of these integrin inhibitors.

A series of integrin-blocking polypeptides, their amino acid sequence is: X-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Y (SEQ ID NO: 17), wherein the X sequence can be missing, Arg-Gly-Asp, Arg-Gly-Asp-Gly-Gly-Gly-Gly (SEQ ID NO: 14), Ala-Cys-Asp-Cys-Arg-Gly-Asp-Cys-Phe-Cys (SEQ ID NO: 15), or Ala-Cys-Asp-Cys-Arg-Gly-Asp-Cys-Phe-Cys-Gly-Gly-Gly-Gly (SEQ ID NO: 16); and the Y sequence can be missing, Arg-Gly-Asp, Arg-Gly-Asp-Gly-Gly-Gly-Gly (SEQ ID NO: 14), Ala-Cys-Asp-Cys-Arg-Gly-Asp-Cys-Phe-Cys (SEQ ID NO: 15) or Ala-Cys-Asp-Cys-Arg-Gly-Asp-Cys-Phe-Cys-Gly-Gly-Gly-Gly (SEQ ID NO: 16).

The series of integrin-blocking polypeptides as defined above, wherein said amino acid sequence is:
polypeptide I: Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala (SEQ ID NO: 1);
polypeptide II: Arg-Gly-Asp-Gly-Gly-Gly-Gly-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala (SEQ ID NO: 2);
polypeptide III: Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Gly-Gly-Gly-Gly-Arg-Gly-Asp (SEQ ID NO: 3);
polypeptide IV: Ala-Cys-Asp-Cys-Arg-Gly-Asp-Cys-Phe-Cys-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala (SEQ ID NO: 8);
polypeptide V: Ala-Cys-Asp-Cys-Arg-Gly-Asp-Cys-Phe-Cys-Gly-Gly-Gly-Gly-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala (SEQ ID NO: 9);
polypeptide VI: Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Arg-Gly-Asp (SEQ ID NO: 10);
polypeptide VII: Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Gly-Gly-Gly-Gly-Ala-Cys-Asp-Cys-Arg-Gly-Asp-Cys-Phe-Cys (SEQ ID NO: 11);
polypeptide VIII: Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Ala-Cys-Asp-Cys-Arg-Gly-Asp-Cys-Phe-Cys (SEQ ID NO: 12);
polypeptide IX: Arg-Gly-Asp-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala (SEQ ID NO:13), including an effective amount of salts (or if necessary, pharmaceutically acceptable vectors or excipients) that can be accepted by said polypeptides.

The application of integrin blockers as defined in claim 1 or 2 in preparation of anti-tumor drugs, wherein the tumors that can be treated thereby include those primary or secondary cancers originated from head and neck region or other organs such as brain, thyroid, esophagus, pancreas, lung, liver, stomach, breast, kidney, gallbladder, colon, rectum, ovary, cervix, uterus, prostate, bladder and testicle, as well as melanoma and sarcomas. The application of integrin blockers as defined in claim 1 or 2 in preparation of drugs for treating or preventing rheumatoid arthritis.

The method for preparing integrin blockers as defined claim 1 or 2, wherein said polypeptides are obtained by means of solid-phase synthesis or recombination of expression vectors.

Integrin blockers as defined in claim 1 or 2, wherein the adjuvant adopted for covalent connection of polypeptides is bovine serum albumin (BSA), human serum albumin (HSA) or polyethylene glycol (PEG).

The application of integrin blockers in preparation of anti-tumor drugs as defined in claim 4, wherein a variety of routes for administering the pharmaceutical composite can be adopted in treatment of primary or secondary cancers, melanoma and sarcomas; said routes include hypodermic injection, intramuscular injection, intravenous injection or drip, oral administration (in the form of pills, capsules, etc.) and nasal spray.

1. The prior patent (ZL200610039298.2) cited in the present invention disclosed that the 6-49 amino acids on the endostatin sequence presented good anti-tumor performance. The present invention, on the basis of this finding, has conducted extensive researches and finally found that the 6-48 amino acids (namely, polypeptide I, EDSM for short, see SEQ ID NO: 1) on the endostatin sequence presented even better anti-tumor performance; it also found that polypeptide I had excellent performance in treatment of rheumatoid arthritis, which consequently broadened the indication range of the polypeptide. In addition, as the newly found polypeptide is one amino acid shorter than the sequence disclosed in the prior patent, the cost for synthesizing it is comparatively lower, which means the present invention bears better social benefits and market potential.

Polypeptide II and polypeptide III are two amino acid sequences newly designed in the present invention. No patent rights have been authorized throughout the world on these two polypeptide sequences. In contrast with the cited patent (ZL200610039298.2), wherein the number of amino acids in sequence EDSM-1 and sequence EDSM-2 is 47 and 55 respectively, polypeptide II and polypeptide III disclosed in the present invention were undergone the following restructuring: a sequence containing four Glycines is added between the integrin ligand sequence (RGD) and the angiogenesis-inhibiting sequence. As far as EDSM-1 is concerned, this restructuring further increases the activity of EDSM-1 by enhancing its flexibility and facilitating the integrin ligand sequence (RGD) to combine the target; as far as EDSM-2 is concerned, this restructuring reduces the number of amino acids on the sequence while keeping its anti-tumor activity intact, which means it would greatly reduce the production cost. Besides, the present invention has also found out that polypeptide II and polypeptide III present desirable effect in treatment of rheumatoid arthritis, which consequently broadens their indication range and highlights their social benefits and market potential.

2. Introduction to the pharmacological mechanism of the polypeptides Researches have shown that on the one hand polypeptide I demonstrates high effect in inhibiting tumor angiogenesis and progression of rheumatoid arthritis, and on the other hand the argnine-glycine-aspartic acid (RGD) sequence is one of important ligands of integrin, which means that the RGD-containing peptide Gly-Gly-Gly-Gly-Arg-Gly-Asp (SEQ ID NO: 35) can specifically recognize integrin. In view of these findings, the present invention discloses two integrin-blocking polypeptides prepared through combining the sequence Gly-Gly-Gly-Gly-Arg-Gly-Asp (SEQ ID NO: 35), which presents high integrin affinity and high integrin-bonding capacity due to the RGD sequence contained therein, with both the N-terminal and C-terminal ends of the angiogenesis-inhibiting sequence (Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala) (SEQ ID NO: 1) respectively. Both polypeptides so constructed, namely, polypeptide II (Arg-Gly-Asp-Gly-Gly-Gly-Gly-Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-eu-Ala-Gly-Thr-Phe-Arg-Ala) (SEQ ID NO: 2) and polypeptide III (Phe-Gln-Pro-Val-Leu-His-Leu-Val-Ala-Leu-Asn-Ser-Pro-Leu-Ser-Gly-Gly-Met-Arg-Gly-Ile-Arg-Gly-Ala-Asp-Phe-Gln-Cys-Phe-Gln-Gln-Ala-Arg-Ala-Val-Gly-Leu-Ala-Gly-Thr-Phe-Arg-Ala-Gly-Gly-Gly-y-Arg-Gly-Asp) (SEQ ID NO: 3) contain 50 amino acids. These two polypeptides on the one hand can inhibit the expression of molecules adhering to the cell surface and the intracellular signal transduction due to existence of the RGD sequence that presents desirable infinity and bonding capacity specifically targeting at integrin αvβ3, and on the other hand can inhibit tumor growth and metastasis by inhibiting tumor angiogenesis—a function of the angiogenesis-inhibiting sequence they contain.

As is indicated by many researches, both in and outside China, tumors, even those of the same histological type and at the same degree of differentiation, may present different sensitivity toward the same drug. Therefore, a procedure to screen the anti-tumor spectrum is needed during the development of a new anti-tumor drug. During this procedure, experiments are conducted to identify the therapeutic effect of a new drug on different tumors—it may have high effect on specific tumors while have low or even no effect on others. With a large quantity of experiments, the inventor of the present invention found out that the integrin blockers have a definitive function target; they on the one hand can significantly inhibit the migration, proliferation and capillary formation of human umbilical vein endothelial cells (HUVECs) as well as the proliferation of some types of tumor cells under in vitro conditions, and on the other hand demonstrate high anti-tumor effect under in vivo conditions. In addition, they present fewer side effects, smaller effective dose and less production cost in comparison with some other anti-tumor drugs. The method for preparing the integrin-blocking polypeptides disclosed in the present invention is reasonably designed and enjoys high feasibility. The drug prepared with this method can be applied in treatment of various solid tumors. This enormously expands the therapeutic spectrum of these integrin blockers, which on the one hand provides a new perspective for developing anti-tumor drugs of the same kind, and on the other hand entails great social benefits and market potential.

The RGD sequence contained in polypeptide II and polypeptide III disclosed in the present invention can targetedly inhibit the activity of endothelial cells of newly generated blood vessels during the formation of pannus in RA patients; therefore, this process can effectively inhibit angiogenesis and be adopted in prevention and treatment of RA. With a large quantity of experiments, the inventor of the present invention found out that polypeptide II and polypeptide III can effectively inhibit the development of adjuvant-induced RA in rats and collagen-induced RA in DBA/1 mice. The in vivo experiments have proved that this series of polypeptides have prominent effect in treatment of RA; they also demonstrate such advantages as few side effect, small effective dose and low production cost. The method for preparing the integrin-blocking polypeptides disclosed in the present invention is reasonably designed and enjoys high feasibility. The drug prepared with this method can be applied in prevention and treatment of RA. This enormously expands the therapeutic spectrum of these integrin blockers, which on the one hand provides a new perspective for developing anti-RA drugs of the same kind, and on the other hand entails great social benefits and market potential.

BRIEF DESCRIPTION

Figure 2:
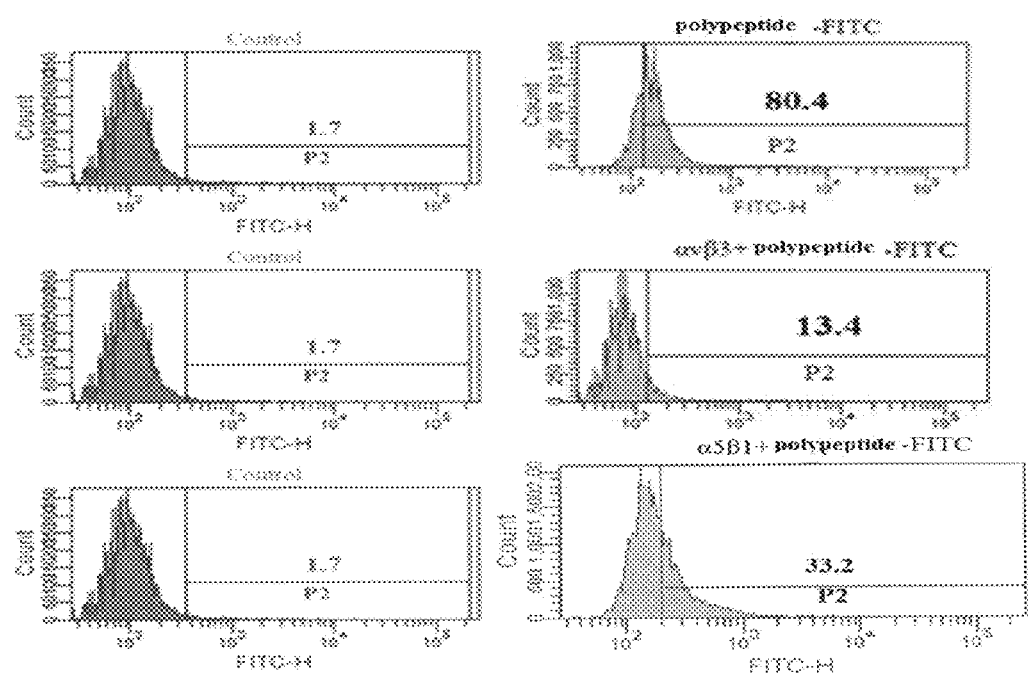
Figure 3:
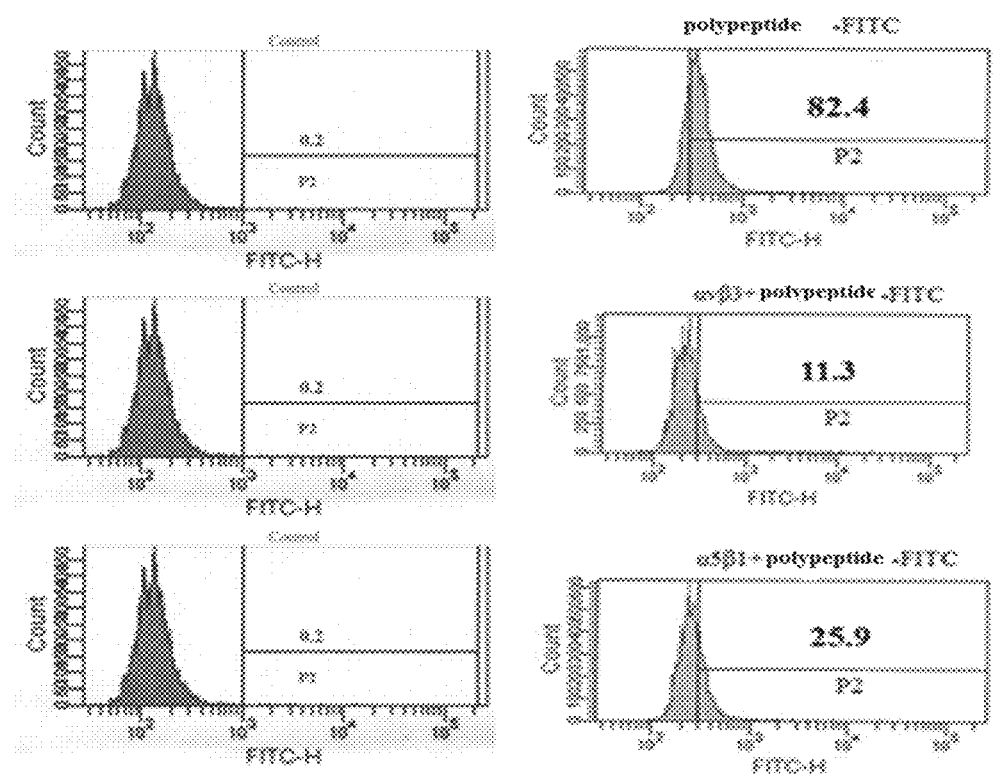

Some of the embodiments will be described in detail, with reference to the following figures, wherein like designations denote like members, wherein:

FIG. 1 expression of integrin αv and integrin β3 in Bel-7402 cells characterized by Western blotting;

FIG. 2 combination between integrin-blocking polypeptide II and the target characterized by flow cytometry; and FIG. 3 combination between integrin-blocking polypeptide III and the target characterized by flow cytometry.

DETAILED DESCRIPTION

Embodiment 1

Synthesization and Detecting Measures of Integrin-Blocking Polypeptides

The solid-phase synthesis was adopted to synthesize polypeptide I, polypeptide II, and polypeptide III. The synthesized products were purified with the high performance liquid chromatography (HPLC), and then the mass spectrometry (MS) and the reversed phase high performance liquid chromatography (RP-HPLC) were adopted to determine the molecular weight and purity of synthesized polypeptides respectively.

Taking Fmoc-Phe (Otbu)-wang resin or Fmoc-Arg (Otbu)-CTC resin as the starting material for the solid-phase synthesis of polypeptide I, Fmoc-Arg (Otbu)-wang resin or Fmoc-Arg (Otbu)-CTC resin as the starting material for the solid-phase synthesis of polypeptide II, and Fmoc-Phe (Otbu)-wang resin or Fmoc-Phe (Otbu)-CTC resin as the starting material for the solid-phase synthesis of polypeptide III; adopting the protected amino acids to consecutively synthesize peptides containing 2 to 43/50 amino acids; washing the product when the synthesis process was completed; after the cleavage and post-treatment processes, the crude product of polypeptide II/polypeptide III was obtained. Dissolving the crude product, purifying it with a preparative HPLC twice, and then freeze-condensing the product to obtain the pure polypeptide II/polypeptide III. The method adopted here can not only ensure high synthesis efficiency but also improve the product purity.

1. steps of peptide synthesis (including formation of the peptide containing 2 to 43/50 amino acids):

polypeptide I: pouring an appropriate amount of Fmoc-Phe(Otbu)-wang resin or Fmoc-Arg (Otbu)-CTC resin into a glass sand-core reaction column, then adding in an appropriate amount of $CH_2Cl_2$ to realize full expansion of the resin.

polypeptide II: pouring an appropriate amount of Fmoc-Arg(Otbu)-wang resin or Fmoc-Arg (Otbu)-CTC resin into a glass sand-core reaction column, then adding in an appropriate amount of $CH_2Cl_2$ to realize full expansion of the resin.

polypeptide III: pouring an appropriate amount of Fmoc-Phe(Otbu)-wang resin or Fmoc-Phe (Otbu)-CTC resin into a glass sand-core reaction column, then adding in an appropriate amount of $CH_2Cl_2$ to realize full expansion of the resin.

a. DECAPPING: adding in an appropriate amount of hexahydropyridine/dimethylformamide (DMF) solution for the decapping process, draining off the decapping reagent after a period of reaction and then washing the resin with DMF; adding in an appropriate amount of the decapping reagent again to remove the Fmoc protecting group.

b. WASHING: draining off the decapping solution, washing the resin with DMF several times in order to sufficiently rinse off by-products.

c. CONDENSING: dissolving the protected amino acids and the activator in DMF and the condensing reagent, evenly stirring the mixture to guarantee sufficient reaction therein.

d. WASHING: draining off the reaction solution, washing the resin with DMF several times in order to sufficiently rinse off by-products.

The peptide cleavage contained the following steps:

First, loading the drained-off resin into a round-bottom flask; then, adding in the cleavage reagent for sufficiently splitting the newly synthesized 50-AA intermediate sequence; finally, separating the resin from the polypeptide with a sand-core funnel. The volume ratio of the components contained in said cleaving reagent was trifluoroacetic acid (TFA):phenol:water:thioanisole:ethylene diamine tartrate (EDT)=88-92:2.5-3.5:2.5-3.5:1.5-2.5:1.5-2.5.

2. The post-treatment process contained the following steps: first, separating out the polypeptide by adding absolute ether into the cleavage reagent; then, centrifuging the mixture and throwing away the supernatant; finally, washing the polypeptide with absolute ether and draining off the absolute ether to obtain the crude polypeptide.

3. The purification process contained the following steps:

a. DISSOLUTION: dissolving the crude polypeptide in water to form 5-20 g/l solution and then filtrating the solution with 0.45 μm hybrid membrane.

PREPARATION: ① primary purification: running 30%-40% acetonitrile and 60%-70% buffer solution at the flow rate of 50-100 ml/min for 10-20 min to equilibrate the preparative column; loading the sample with a metering pump, setting the baseline and collecting the solution with absorption value over 200 mv at the UV wavelength of 220 nm; detecting whether there was the sample in the eluate; adopting gradient elution, starting at 30%-40% acetonitrile and progressing linearly at 80-90% acetonitrile over 30-50 min; collecting the solution with absorption value over 200 mv at the UV wavelength of 220 nm; converging the part with detected purity over 95% as the peak and ready for the secondary purification. ② secondary purification: adopting rotary evaporation to remove the organic solvent contained in the peak component collected in the primary purification, loading the sample again with a metering pump; eluting the column with 30%-40% acetonitrile and 60%-70% buffer solution at the flow rate of 50-100 ml/min; setting the baseline and collecting the solution with absorption value over 200 mv at the UV wavelength of 220 nm; detecting whether there was the sample in the eluate; adopting gradient elution, starting at 30%-40% acetonitrile and progressing linearly at 80-90% acetonitrile over 30-50 min; collecting the solution with absorption value over 200 mv at the UV wavelength of 220 nm; the part with detected purity over 95% was regarded as qualified.

b. CONDENSING, FILTRATING AND FREEZE-DRYING: adopting a rotary evaporator to condense the qualified solution at 37° C. so that the residual solvent and eluting water could be removed; finally, filtrating the solution with 0.22 μm membrane; placing the filtrate in a freeze-drying plate and freeze-drying the filtrate in a freeze-dryer.

4. determination of purity and molecular weight

Collecting the freeze-dried pure product, adopting the reversed phase high performance liquid chromatography (RP-HPLC) to determine and analyze the purity of the polypeptide.

In the present invention, the solid-phase synthesis was successfully adopted to synthesize the integrin-blocking polypeptides I, II and III. This method presented many advantages such as high repeatability, high practicality and little pollution. Two types of resin could be used in the present invention, namely, wang resin and CTC resin; in contrast with other types of resin, the wang resin demonstrates higher stability, less side reactions, higher yield and better peak shape of the crude product, which mean less production cost; in contrast with other types of resin, the CTC resin is less affected by reaction temperature and presents higher reaction rate. The present invention also adopted RP-HPLC to purify the synthesized polypeptide; in addition, in contrast with isocratic elution, the gradient elution adopted in the present invention presented better separating effect as this mode of elution guaranteed appropriate retention time during the separation reaction, which consequently led to higher production efficiency and higher purity.

RESULT: RP-HPLC analysis showed that the purity of the synthesized polypeptide I, II and III was 95.39%, 98.41%, 96.40% respectively; the result met the required purity standard.

Embodiment 2

Analysis of the Target of Integrin-Blocking Polypeptide II and Polypeptide III (1) the Target Integrin αvβ3 Expressed by Cells was Analyzed with Western Blotting Digesting Bel-7402 cells in logarithmic phase with 0.25% trypsinase, centrifuging the collected cells at 800 rpm for 5 min; counting the cells and adding in protein extraction solution at the rate of 20 μl per $1 \times 10^5$ cells; scattering cells through blow-suctioning and placing them at 4° C. for 30 min for lysis; adding in ¼ volume of 5× protein loading buffer and incubating the sample in boiling water for 5-10 min. Taking 20 μl protein sample for 10% SDS-PAGE electrophoresis; transferring the protein from the gel to PVDF membrane through semi-dry electrotransfer (constant current 1 mA/cm$^2$, 3 h); dyeing the PVDF membrane in ponceau for 30 s then decoloring it with dH$_2$O till clear bands emerged on the membrane; cutting the upper right corner of the membrane to mark the protein side; blocking the PVDF membrane with blocking buffer at room temperature for 1.5 h, and then washing the PVDF membrane with PBST 2-3 times, 5-10 min each time. Adding in the primary antibody, incubating the sample at 4° C. overnight or 37° C. for 1.5 h, and washing the membrane with PBST 3-5 times, 5-10 min each time. Adding in the secondary antibody, incubating the sample at 4° C. overnight or 37° C. for 1.5 h, and then washing the membrane with PBST 3-5 times, 5-10 min each time. In a darkroom (red light allowed), placing the PVDF membrane on preservative film with the protein side upward; evenly dripping a luminescent solution on the membrane surface and waiting for 5 min of reaction; wrapping the PVDF membrane within preservative film and cutting a piece of X-ray film of the same size as the membrane, and putting them together in a cassette for 0.5-5 min (dependent on the light intensity of luminescent bands); taking out the X-ray film and putting it into the developing solution till band images emerged on the film, then transferring the film into the stop bath (5% glacial acetic acid) and keep the film there for 1 min; washing the film with flowing water for 1 min and then putting it into the fixing solution till the background part of the film turned into transparent; finally, washing the film with flowing water for 20 min to fixate the images.

(2) Combination Between Integrin-Blocking Polypeptide II/III and the Target Analyzed with Flow Cytometry culturing Bel-7402 cells in a culture flask to 80% confluence, then digesting and collecting cells and washing them with pre-cooled PBS buffer twice, resuspending cells with 1% BSA-containing PBS buffer for 30 min; incubating 2 µl mouse anti-human integrin αvβ3 monoclonal antibody (function-blocking) and 2 µl mouse anti-human integrin α5β1 monoclonal antibody (function-blocking) with the cell suspension (1.0 µg/µl, 1:200) respectively at 4° C. for 1.5 h; collecting the cells and washing them with pre-cooled PBS buffer twice, then incubating polypeptide II and polypeptide III modified with 100 µl FITC (2 mg/ml) with the cell suspension respectively at 4° C. for 1.5 h; collecting cells after this labeling process and washing them with pre-cooled PBS buffer twice; resuspending cells with 400 µl PBS buffer and analyzing them with flow cytometry; detecting intensity of FITC fluorescence with FL1 channel.

RESULTS: Determination of the target (integrin αvβ3) through cell expression. As is indicated in FIG. 1, integrin αvβ3 was expressed on the surface of Bel-7402 cells, which means integrin αvβ3 can be used as the combination target for later experiments.

Combination between integrin-blocking polypeptide II/III and the target analyzed with flow cytometry. As is shown in FIG. 2, the fluorescence intensity of integrin-blocking polypeptide II labeled with FITC was 80.4% before adding in the antibody and the incubation process; however, it reduced to 13.4% when adding in integrin αvβ3 antibody and 33.2% when adding in integrin α5β1 antibody. As is shown in FIG. 3, the fluorescence intensity of polypeptide III labeled with FITC was 82.4% before adding in the antibody and the incubation process; however, it reduced to 11.3% when adding in integrin αvβ3 antibody and 25.9% when adding in integrin α5β1 antibody. The flow cytometry analysis showed that polypeptide II and polypeptide III could combine with both integrin αvβ3 and integrin α5β1, however, their major combination target was integrin αvβ3.

Embodiment 3

Test on Integrin-Blocking Polypeptides in Inhibiting the Migration of Human Umbilical Vein Endothelial Cells (HUVECs)

Diluting 10 mg/ml Matrigel (BD Company, USA) with HUVEC culture medium at the ratio of 1:2, smearing the Matrigel solution on the membrane of a transwell chamber, and drying at the room temperature. Digesting the HUVECs with trypsinase when they reached the logarithmic phase; collecting the cells and washing them with PBS buffer twice, and then resuspending the cells with blank HUVECs culture medium. Counting the cells under a microscope, adjusting the cell concentration to 1×10$^5$ cells/ml. Preparing the testing solution for all groups, and diluting with blank HUVECs culture medium to 100 µl. Seeding the cells into the transwell chamber, 100 µl for each insert, adding also the testing solution of all groups into the transwell chamber. Adding 0.6 ml endothelial cell culture medium containing 5% fetal calf serum (FCS) and 1% endothelial cell growth supplement (ECGS) into the 24-well plate to stimulate cell migration, and incubating the cells in 5% CO$_2$ at 37° C. for 24 h. Removing the culture solution, fixing the cells with 90% ethanol at the room temperature for 30 min, and staining the cells with 0.1% crystal violet at the room temperature for 10 min, then washing with clean water and gently scraping off non-migrated cells with cotton swabs; observing cells under a microscope and choosing 4 FOVs for cell counting and photographing. The migration inhibition (MI) rate was calculated in accordance with the following formula:

$$MI(\%) = 1 - \frac{N_{test}}{N_{control}} \times 100\%$$

wherein $N_{test}$ is the number of migrated cells in the test groups while $N_{control}$ is the number of migrated cells in the negative control group.

Conducting the same experiment three times independently, calculating mean and standard deviation (mean±SD) of all detected data and analyzing the data with T-test, wherein *P<0.05 refers to significant difference and **P<0.01 extremely significant difference.

TABLE 1 inhibition effect of integrin-blocking polypeptide I on migration of HUVECs

| group (n = 8) | dose (µg/ml) | number of migrated cells (mean ± SD) | MI rate (%) |
| --- | --- | --- | --- |
| polypeptide I | 0.5 | 979.8 ± 75.3** | 18.69% |
|  | 1 | 956.0 ± 78.2** | 20.66% |
|  | 2 | 961.3 ± 89.5** | 20.23% |
|  | 4 | 903.5 ± 68.7** | 25.02% |
|  | 8 | 815.5 ± 62.32** | 32.32% |
|  | 16 | 706.3 ± 48.7** | 41.39% |
|  | 32 | 871.8 ± 67.9** | 27.66% |
|  | 64 | 929.5 ± 99.7** | 22.86% |
| ES | 20 | 911.7 ± 33.5** | 24.34% |
| control | 0 | 1204.8 ± 29.3 | — | a:
* P < 0.05,
**P < 0.01.

TABLE 2 inhition effect of integrin-blocking
polypeptide II on migration of HUVECs

| group (n = 8) | dose (μg/ml) | number of migrated cells (mean ± SD) | MI rate (%) |
|---|---|---|---|
| polypeptide II | 0.13 | 875.0 ± 35.3** | 24.44% |
| | 0.25 | 800.7 ± 64.8** | 30.85% |
| | 0.5 | 685.7 ± 32.5** | 40.78% |
| | 1 | 611.0 ± 74.1** | 47.24% |
| | 2 | 600.3 ± 39.3** | 48.15% |
| | 4 | 531.5 ± 72.6** | 54.10% |
| | 8 | 348.8 ± 39.9** | 69.87% |
| | 16 | 460.1 ± 97.3** | 60.27% |
| ES | 20 | 880.2 ± 33.3** | 23.99% |
| control | — | 1158.0 ± 54.5** | — | a:
* P < 0.05,
**P < 0.01.

TABLE 3 inhibition effect of integrin-blocking
polypeptide III on migration of HUVECs

| group (n = 8) | dose (μg/ml) | number of migrated cells (mean ± SD) | MI (%) |
|---|---|---|---|
| polypeptide III | 0.13 | 787.1 ± 46.3** | 23.08% |
| | 0.25 | 595.7 ± 29.3** | 41.78% |
| | 0.5 | 490.7 ± 17.1** | 52.04% |
| | 1 | 237.6 ± 19.0** | 76.78% |
| | 2 | 384.1 ± 43.0** | 62.46% |
| | 4 | 482.3 ± 19.2** | 52.86% |
| ES | 20 | 866.0 ± 27.2 | 15.37% |
| control | — | 1023.2 ± 11.1 | — | a:
* P < 0.05,
**P < 0.01.

RESULTS: the inhibition effect of integrin-blocking polypeptide I on migration of HUVECs is shown in Table 1. In contrast with the negative control group, integrin-blocking polypeptide I could inhibit the migration of HUVECs induced by 5% FCS and 1% ECGS; the inhibition effect presented a certain dose-dependency at medium and low doses. The inhibition effect of polypeptide I on cell migration presented extremely significant difference (**P<0.01) at either high, medium or low dose in contrast with the negative control group; however, the inhibition effect of polypeptide I on cell migration slightly decreased at high dose in contrast with that at medium dose. When the dose of polypeptide I was 16 μg/ml, its inhibition effect on cell migration reached the highest 41.39%.

The inhibition effect of integrin-blocking polypeptide II on migration of HUVECs is shown in Table 2. In contrast with the negative control group, integrin-blocking polypeptide II could inhibit the migration of HUVECs induced by 5% FCS and 1% ECGS; the inhibition effect presented a certain dose-dependency at medium and low doses. The inhibition effect of polypeptide II on cell migration presented extremely significant difference (**P<0.01) at either high, medium or low dose in contrast with the negative control group; however, the inhibition effect of polypeptide II on cell migration slightly decreased at high dose in contrast with that at medium dose. The inhibition rates at the dose of 4 μg/ml, 8 μg/ml and 16 μg/ml were all over 50%, reaching 54.10%, 69.87% and 60.27% respectively. When the dose of polypeptide II was 8 μg/ml, its inhibition effect on cell migration reached the highest 69.87%.

The inhibition effect of integrin-blocking polypeptide III on migration of HUVECs is shown in Table 3. In contrast with the negative control group, integrin-blocking polypeptide III could inhibit the migration of HUVECs induced by 5% FCS and 1% ECGS; the inhibition effect presented a certain dose-dependency at medium and low doses. The inhibition effect of polypeptide III on cell migration slightly decreased at high dose in contrast with that at medium dose. The inhibition effect of polypeptide III at all doses presented extremely significant difference (**P<0.01) on cell migration; the inhibition rate at the dose of 1 μg/ml, 2 μg/ml and 4 μg/ml were all over 50%, reaching 76.78%, 62.46% and 52.86% respectively; when the dose of polypeptide III was 1 μg/ml, its inhibition effect on cell migration reached the highest 76.78%.

Embodiment 4

Test on Integrin-Blocking Polypeptides in Inhibiting Capillary Formation of Human Umbilical Vein Endothelial Cells (HUVECs)

Thawing 10 mg/mL matrigel (BD Company, USA) stocked at −20° C. overnight at 4° C., diluting it with HUVEC culture medium at the ratio of 1:1; smearing 30 μl of the solution on a 96-well plate (Greiner Company, USA), placing the plate at a 37 incubator for 1 h of aggregation. Digesting the HUVECs with 0.2% ethylene diamine tetraacetic acid (EDTA) when they reached the logarithmic phase; collecting the cells and washing them with PBS buffer twice, and then resuspending the cells with blank HUVEC culture medium. Counting the cells under a microscope, adjusting the cell concentration to $1 \times 10^5$ cells/ml. Preparing the testing solution for all groups, and diluting with blank HUVEC culture medium to 100 μl. Seeding the cells into the 96-well plate, 100 μl for each well, adding also the testing solution into each well and incubating the cells in 5% $CO_2$ at 37° C. After 6 h, 12 h, 24 h, 36 h, 48 h, 60 h of incubation, randomly choosing 5 FOVs for each dose, photographing and counting the cells; calculating the number of capillary structures at different doses and analyzing the inhibition effect of polypeptide II and polypeptide III on HUVECs' differentiating into capillaries. The inhibition rate of capillary formation was calculated in accordance with the following formula:

$$\text{inhibition rate of capillary formation (\%)} = 1 - \frac{N_{test}}{N_{control}} \times 100\%$$

wherein $N_{test}$ is the number of capillary structures in the test groups while $N_{control}$ is the number of capillary structures in the negative control group.

Conducting the same experiment three times independently, calculating mean and standard deviation (mean±SD) of all detected data and analyzing the data with T-test, wherein *P<0.05 refers to significant difference and **P<0.01 extremely significant difference.

TABLE 4 inhibition effect of integrin-blocking polypeptide II on capillary formation of HUVECs

| group (n = 5) | 6 h dose (μg/ml) | 6 h number of capillary structures (mean ± SD) | 6 h inhibition rate (%) of capillary formation | 12 h dose (μg/ml) | 12 h number of capillary structures (mean ± SD) | 12 h inhibition rate (%) of capillary formation |
|---|---|---|---|---|---|---|
| polypeptide II | 0.25 | 26.0 ± 4.3 | 8.45% | 0.25 | 14.0 ± 3.3* | 23.08% |
|  | 0.5 | 20.0 ± 0.8** | 29.58% | 0.5 | 11.4 ± 1.6** | 37.36% |
|  | 1 | 18.5 ± 5.0** | 34.86% | 1 | 10.7 ± 1.2** | 40.93% |
|  | 2 | 7.2 ± 0.8** | 74.65% | 2 | 3.5 ± 0.5** | 80.77% |
|  | 4 | 6.0 ± 1.0** | 78.87% | 4 | 3.3 ± 2.5** | 81.68% |
|  | 8 | 8.0 ± 1.4** | 71.83% | 8 | 4.3 ± 0.5** | 76.19% |
| ES | 20 | 17.0 ± 3.6** | 40.14% | 20 | 10.3 ± 2.3** | 43.22% |
| taxol | 10 | 0.0 ± 0.0** | 100.00% | 10 | 0.0 ± 0.0** | 100.00% |
| control | — | 28.4 ± 3.0 | — | — | 18.2 ± 1.7 | — |

TABLE 5 inhibition effect of integrin-blocking polypeptide III on capillary formation of HUVECs

| group (n = 5) | 6 h dose (μg/ml) | 6 h number of capillary structures (mean ± SD) | 6 h inhibition rate (%) of capillary formation | 12 h dose (μg/ml) | 12 h number of capillary structures (mean ± SD) | 12 h inhibition rate (%) of capillary formation |
|---|---|---|---|---|---|---|
| polypeptide III | 0.25 | 26.4 ± 1.9** | 19.02% | 0.25 | 16.4 ± 1.5** | 18.81% |
|  | 0.5 | 20.2 ± 2.3** | 37.88% | 0.5 | 14.6 ± 2.0** | 27.39% |
|  | 1 | 11.0 ± 1.0** | 66.26% | 1 | 8.6 ± 1.5** | 57.10% |
|  | 2 | 10.6 ± 2.8** | 67.28% | 2 | 9.0 ± 1.0** | 55.45% |
| ES | 20 | 22.0 ± 2.5** | 32.52% | 20 | 18.0 ± 2.1** | 10.89% |
| taxol | 10 | 0.0 ± 0.0** | 100% | 10 | 0.0 ± 0.0** | 100% |
| control | — | 32.60 ± 1.34 | — | — | 20.20 ± 1.92 | — |

RESULTS: The inhibition effect of polypeptide II on differentiation of HUVECs is shown in Table 4. The differentiation process of HUVECs after 6 h-60 h of incubation was observed: the capillary structures started to appear after 6 h of incubation, reached the highest point after 6 h-12 h of incubation, started to decrease after 12 h of incubation and almost completely disappeared after 60 h of incubation. The number of capillary structures in polypeptide II groups (at either high, medium or low dose) was smaller than that in the negative control group, which means that polypeptide II presents inhibition effect on HUVECs' differentiating into capillaries at either high, medium or low dose; its inhibition rates at both medium and low doses were over 50%, and they were dose-dependent to some extent. The capillary structures were in minimum number when the doses of polypeptide II were 2 μg/ml, 4 μg/ml and 8 μg/ml, that is to say, polypeptide II presented the highest inhibition rate on capillary formation at these doses. After 6 h of incubation, the inhibition rates of polypeptide II at the doses of 2 μg/ml, 4 μg/ml, and 8 μg/ml reached 74.65%, 78.87% and 71.83% respectively; after 12 h of incubation, the inhibition rates of polypeptide II at the doses of 2 μg/ml, 4 μg/ml and 8 μg/ml reached 80.77%, 81.68% and 76.19% respectively. After 6 h of incubation, the inhibition effect of polypeptide II at the doses of 0.5 μg/ml, 1 μg/ml, 2 μg/ml, 4 μg/ml and 8 μg/ml exhibited extremely significant difference in contrast with the negative control group.

The inhibition effect of polypeptide III on differentiation of HUVECs is shown in Table 5. The differentiation process of HUVECs after 6 h-60 h of incubation was observed: the capillary structures started to appear after 6 h of incubation, reached the highest point after 6 h-12 h of incubation, started to decrease after 12 h of incubation and almost completely disappeared after 60 h of incubation. The number of capillary structures in polypeptide III groups (at either high, medium or low dose) was smaller than that in the negative control group, which means that polypeptide III presents inhibition effect on HUVECs' differentiating into capillaries at either high, medium or low dose; its inhibition rates at both medium and low doses were over 60%, and they were dose-dependent to some extent. The capillary structures were in minimum number when the doses of polypeptide III were 1 μg/ml and 2 μg/ml, that is to say, polypeptide III presented the highest inhibition rate on capillary formation at these doses. After 6 h of incubation, the inhibition rates of polypeptide III at the doses of 1 μg/ml and 2 μg/ml reached 66.26% and 67.28% respectively. After 12 h of incubation, the inhibition rates of polypeptide III at the doses of 1 μg/ml and 2 μg/ml reached 57.10% and 55.45% respectively. After 6 h of incubation, the inhibition effect of polypeptide III at all does, namely, 0.25 μg/ml, 0.5 μg/ml, 1 μg/ml and 2 μg/ml, exhibited extremely significant difference in contrast with the negative control group.

Embodiment 5

Test on the Inhibition Effect of Integrin-Blocking Polypeptide I, Polypeptide II and Polypeptide III on Transplanted Melanoma B16F10 in C57BL/6 Black Mice Taking a certain amount of vigorously growing melanoma tissue, grinding the tissue under sterile conditions and preparing cell suspension at the concentration of $1 \times 10^7$ cells/ml, hypodermically inoculating 0.1 ml of the cell suspension into the right axillary region of mice. Keeping measuring the diameter of the transplanted melanoma with a vernier caliper, and randomly dividing the mice into several groups when the volume of the tumor reached 100-200 mm³. Observing the dynamic effect of integrin-blocking polypeptides on inhibiting the growth of the tumor by means of documenting the change of tumor diameters. Measuring the tumor diameter once every other day and recording the body weight of mice simultaneously. Hypodermically injecting polypeptides and other drugs into the left axillary region of mice from the experimental groups respectively while administering only equal quantity of physiological saline to the mice from the negative control group. The total medication period was 14 days, during which cyclophosphamide was administered once every other day, taxol once every three days, low-dose polypeptide twice a day and all other drugs once a day. After 14 days of medication, killing the mice and surgically dissecting the tumors and measuring the weight of tumors. The tumor volume (TV) was calculated in accordance with the following formula:

$$TV = 1/2 \times a \times b^2$$

wherein a, b refer to the length and width of the tumor respectively.

The relative tumor volume (RTV) can be calculated in accordance with the results of measurement, using the formula: $RTV = V_t/V_0$, wherein $V_0$ refers to the initial tumor volume measured on the date starting medication (namely $d_0$) while $V_t$ the tumor volume obtained through every measurement. The anti-tumor activity was evaluated by relative proliferation rate T/C (%), which was calculated in accordance with the following formula:

$$T/C\ (\%) = \frac{T_{RTV}}{C_{RTV}} \times 100\%$$

wherein $T_{RTV}$ refers to the RTV of test groups; $C_{RTV}$ refers to the RTV of the negative control group.

Conducting the same experiment three times independently, calculating mean and standard deviation (mean±SD) of all detected data and analyzing the data with T-test, wherein *P<0.05 refers to significant difference and **P<0.01 extremely significant difference.

TABLE 6 inhibition effect of polypeptide I on transplanted melanoma B16F10 in C57BL/6 mice

| group | dose (mg/kg/time) | initial weight (g) | initial number | final weight (g) | final number | tumor weight (g) | tumor inhibition rate |
|---|---|---|---|---|---|---|---|
| control | — | 16.7 ± 1.0 | 12 | 21.9 ± 1.4 | 12 | 2.65 ± 1.22 | — |
| taxol | 10 | 16.5 ± 0.7 | 10 | 16.4 ± 2.8 | 8 | 0.77 ± 0.62** | 70.84% |
| polypeptide I (high) | 3 | 17.1 ± 0.8 | 10 | 22.9 ± 1.2 | 9 | 1.66 ± 1.35 | 37.26% |
| polypeptide I (low) | 0.75 | 16.9 ± 1.0 | 10 | 23.6 ± 2.0 | 9 | 1.80 ± 0.78 | 32.17% |

TABLE 7 inhibition effect of polypeptide II on transplanted melanoma B16F10 in C57BL/6 mice

| group | dose (mg/kg/time) | initial weight (g) | initial number | final weight (g) | final number | tumor weight (g) | tumor inhibition rate |
|---|---|---|---|---|---|---|---|
| control | — | 15.8 ± 1.0 | 12 | 22.9 ± 1.4 | 12 | 3.99 ± 1.03 | — |
| taxol | 10 | 15.3 ± 0.7 | 8 | 16.8 ± 2.8 | 6 | 0.98 ± 0.30** | 75.49% |
| cyclophosphamide | 15 | 15.2 ± 0.9 | 8 | 17.3 ± 1.5 | 8 | 1.40 ± 0.06** | 64.95% |
| polypeptide II (high) | 3 | 15.7 ± 0.8 | 8 | 21.9 ± 1.2 | 6 | 2.36 ± 0.38 | 40.80% |
| polypeptide II (medium) | 1.5 | 15.1 ± 0.5 | 8 | 22.6 ± 0.6 | 7 | 2.63 ± 0.69 | 34.17% |
| polypeptide II (low) | 0.75 | 15.3 ± 1.0 | 8 | 21.6 ± 2.0 | 6 | 1.63 ± 0.53** | 59.06% |
| polypeptide II (low, bid) | 0.75 | 15.3 ± 0.9 | 8 | 22.4 ± 1.6 | 7 | 1.79 ± 1.03** | 55.22% |

TABLE 8 inhibition effect of polypeptide III on transplanted melanoma B16F10 in C57BL/6 mice

| group | dose (mg/kg/time) | initial weight (g) | initial number | final weight (g) | final number | tumor weight (g) | tumor inhibition rate |
|---|---|---|---|---|---|---|---|
| control | — | 15.8 ± 1.0 | 12 | 22.9 ± 1.4 | 12 | 3.99 ± 1.03 | — |
| taxol | 10 | 15.3 ± 0.7 | 8 | 16.8 ± 2.8 | 6 | 0.98 ± 0.30** | 75.49% |
| cyclophosphamide | 15 | 15.2 ± 0.9 | 8 | 17.3 ± 1.5 | 8 | 1.40 ± 0.06** | 64.95% |
| polypeptide III(high) | 0.375 | 14.7 ± 0.6 | 8 | 22.2 ± 1.8 | 7 | 1.47 ± 0.42* | 63.07% |
| polypeptide III(medium) | 0.1875 | 15.4 ± 0.5 | 8 | 21.2 ± 1.5 | 7 | 1.60 ± 1.09** | 59.82% |
| polypeptide III(low) | 0.09375 | 15.5 ± 0.6 | 8 | 21.5 ± 0.8 | 6 | 1.25 ± 0.47** | 68.67% |
| polypeptideIII (low, bid) | 0.09375 | 15.3 ± 0.9 | 8 | 22.4 ± 1.6 | 7 | 1.23 ± 0.27** | 69.21% |

RESULTS: The inhibition effect of polypeptide I on transplanted melanoma B16F10 in C57BL/6 black mice is shown in Table 6. The taxol group was administered with taxol 10 mg/kg/time, and the inhibition rate of taxol on transplanted melanoma B16F10 in C57BL/6 black mice was 70.84%; however, this drug greatly reduced the body weight of animals; the weight of mice from the taxol group was lighter than that from the negative control group and the polypeptide groups, which means taxol induces severer toxic and side effects. The inhibition rates of polypeptide I at high and low doses on transplanted melanoma B16F10 in C57BL/6 black mice were 37.26% and 32.17% respectively. The results about the inhibition effect of polypeptide I on transplanted melanoma B16F10 in C57BL/6 black mice demonstrated that, in contrast with the negative control group, polypeptide I presented considerably good effect in inhibiting the growth of the transplanted melanoma B16F10 in C57BL/6 black mice; besides, the weight of mice showed no significant change in contrast with the negative control group, and no significant toxic and side effects were observed.

The inhibition effect of polypeptide II on transplanted melanoma B16F10 in C57BL/6 black mice is shown in Table 7. The taxol group was administered with taxol 10 mg/kg/time, and the inhibition rate of taxol on transplanted melanoma B16F10 in C57BL/6 black mice was 75.49%; however, this drug greatly reduced the body weight of animals; the weight of mice from the taxol group was lighter than that from the control group and the polypeptide groups, which means taxol induces severer toxic and side effects. The inhibition rates of polypeptide II at high, medium, low and low twice a day (hereinafter, "low bid") doses on transplanted melanoma B16F10 in C57BL/6 black mice were 40.80%, 34.17%, 59.06% and 55.22% respectively. The tumor volume of mice from both the low-dose group and the low-dose bid group exhibited extremely significant difference in contrast with that from the negative control group; meanwhile, animals from the experimental groups showed no significant change in body weight, and no obvious toxic and side effects were observed in contrast with the negative control group.

The inhibition effect of polypeptide III on transplanted melanoma B16F10 in C57BL/6 black mice is shown in Table 8. The inhibition rates of polypeptide III at high, medium, low and low-bid doses on transplanted melanoma B16F10 in C57BL/6 black mice were 63.07%, 59.82%, 68.67% and 69.21% respectively. The tumor volume of animals from the high dose polypeptide III group presented significant difference in contrast with that from the negative control group; the tumor volumes of animals from the medium, low, low-bid polypeptide III groups presented extremely significant difference in contrast with that from the negative control group. In contrast with the negative control group, polypeptide III presented most desirable effect in inhibiting growth of transplanted melanoma B16F10 in C57BL/6 black mice when being administered at 0.09375 mg/kg, twice a day; besides, no severe weight change or obvious toxic and side effects were observed on testing animals in contrast with those from the negative control group.

Embodiment 6

Test on the Inhibition Effect of Integrin-Blocking Polypeptide I, Polypeptide II and Polypeptide III on Heterotransplanted Human Breast Cancer MDA-MB-231 in Nude Mice Taking a certain amount of vigorously growing tumor tissue, grinding the tumor tissue under sterile conditions and preparing cell suspension at the concentration of 1×107 cells/ml; then hypodermicaly inoculating 0.1 ml of the cell suspension into the right axillary region of nude mice. Keeping measuring the diameter of the transplanted tumor with a vernier caliper, and randomly dividing the mice into groups when the volume of the tumor reached 100-200 mm³. Observing the dynamic effect of integrin-blocking polypeptides on inhibiting the growth of the tumor by means of documenting the change of tumor diameters. Measuring the tumor diameter once every other day and recording the body weight of mice simultaneously. Intravenously injecting polypeptides to mice from test groups while administering equal quantity of physiological saline to mice from the negative control group. The total medication period was 14 days. Avastin was adopted to set up a positive control group; it was administered through the tail vein once every three days while all other drugs were administered through the tail vein once a day. Leaving mice for a one-week rest after 14 days' medication, then (21 days after medication) killing the mice, surgically dissecting the tumors and measuring the weight of tumors. The tumor volume (TV) was calculated in accordance with the following formula:

$$TV = \tfrac{1}{2} \times a \times b^2$$

wherein a, b refer to the length and width of the tumor respectively.

The relative tumor volume (RTV) can be calculated in accordance with the results of measurement, using the formula: $RTV = V_t/V_0$, wherein $V_0$ refers to the initial tumor volume measured on the date starting medication (namely $d_0$) while $V_t$ the tumor volume obtained through every measurement. The anti-tumor activity was evaluated by relative proliferation rate T/C (%), which was calculated in accordance with the following formula:

$$T/C\ (\%) = \frac{T_{RTV}}{C_{RTV}} \times 100\%$$

wherein $T_{RTV}$ refers to the RTV of experimental groups; $C_{RTV}$ refers to the RTV of the negative control group.

Conducting the same experiment three times independently, calculating mean and standard deviation (mean±SD) of all detected data and analyzing the data with T-test, wherein *P<0.05 refers to significant difference and **P<0.01 extremely significant difference.

TABLE 9 inhibition effect of polypeptide I on heterotransplanted human breast cancer MDA-MB-231 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.19 ± 1.24 | 12 | 22.18 ± 1.88 | 12 | 1.19 ± 0.31 | — |
| avastin | 10 | 20.50 ± 0.77 | 10 | 17.56 ± 1.65 | 9 | 0.26 ± 0.08** | 78.53% |
| endostar(rh-endostatin) | 2.5 | 19.97 ± 1.19 | 10 | 19.67 ± 1.36 | 10 | 0.62 ± 0.21 | 47.71% |
| polypeptide I (high) | 3 | 20.35 ± 0.95 | 10 | 19.34 ± 1.13 | 10 | 0.56 ± 0.10 | 52.95% |
| polypeptide I (medium) | 1.5 | 20.50 ± 1.21 | 10 | 20.21 ± 1.97 | 10 | 0.49 ± 0.13** | 58.82% |
| polypeptide I (low) | 0.75 | 20.69 ± 1.20 | 10 | 22.28 ± 1.75 | 12 | 0.58 ± 0.22* | 51.26% |

TABLE 10 inhibition effect of polypeptide II on heterotransplanted human breast cancer MDA-MB-231 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.11 ± 0.60 | 12 | 23.10 ± 0.61 | 12 | 1.19 ± 0.31 | — |
| avastin | 10 | 20.25 ± 0.64 | 8 | 21.23 ± 0.47 | 6 | 0.26 ± 0.08** | 78.53% |
| endostar (rh-endostatin) | 2.5 | 20.00 ± 0.67 | 8 | 22.94 ± 0.64 | 7 | 0.62 ± 0.21 | 47.71% |
| polypeptide II (high) | 3 | 20.38 ± 0.39 | 8 | 23.13 ± 0.67 | 8 | 0.43 ± 0.12* | 63.80% |
| polypeptide II (medium) | 1.5 | 20.16 ± 0.45 | 8 | 22.86 ± 0.65 | 8 | 0.38 ± 0.12** | 67.82% |
| polypeptide II (low) | 0.75 | 20.31 ± 0.50 | 8 | 23.03 ± 0.65 | 8 | 0.50 ± 0.17* | 57.83% |

TABLE 11 inhibition effect of polypeptide III on heterotransplanted human breast cancer MDA-MB-231 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.11 ± 0.60 | 12 | 23.10 ± 0.61 | 12 | 1.19 ± 0.31 | — |
| avastin | 10 | 20.25 ± 0.64 | 8 | 21.23 ± 0.47 | 6 | 0.26 ± 0.08** | 78.53% |
| endostar (rh-endostatin) | 2.5 | 20.00 ± 0.67 | 8 | 22.94 ± 0.64 | 7 | 0.62 ± 0.21 | 47.71% |
| polypeptide III(high) | 0.75 | 20.09 ± 0.56 | 8 | 23.06 ± 0.64 | 8 | 0.49 ± 0.17* | 58.82% |
| polypeptide III(medium) | 0.375 | 20.00 ± 0.58 | 8 | 22.63 ± 0.57 | 8 | 0.32 ± 0.09** | 72.86% |
| polypeptide III(low) | 0.1875 | 20.03 ± 0.44 | 8 | 23.10 ± 0.42 | 8 | 0.45 ± 0.15* | 61.91% |

RESULTS: the inhibition effect of polypeptide I on heterotransplanted human breast cancer MDA-MB-231 in nude mice is shown in Table 9. The inhibition rate of avastin on heterotransplanted human breast cancer MDA-MB-231 in nude mice was 78.53% and the body weight of mice showed no obvious change; the inhibition rates of polypeptide I at high, medium and low doses on heterotransplanted human breast cancer MDA-MB-231 in nude mice were 52.95%, 58.82% and 51.26% respectively. The tumor volume of mice from the low-dose polypeptide group presented significant difference in contrast with that from the negative control group; the tumor volume of mice from the medium-dose polypeptide group presented extremely significant difference in contrast with that from the negative control group. Meanwhile, animals from the polypeptide groups showed no significant change in body weight, and no obvious toxic and side effects were observed in contrast with the negative control group.

The inhibition effect of polypeptide II on heterotransplanted human breast cancer MDA-MB-231 in nude mice is shown in Table 10. The inhibition rate of avastin on heterotransplanted human breast cancer MDA-MB-231 in nude mice was 78.53% and the body weight of mice showed no obvious change; the inhibition rates of polypeptide II at high, medium and low doses on heterotransplanted human breast cancer MDA-MB-231 in nude mice were 63.80%, 67.82% and 57.83% respectively. The tumor volume of mice from both the high-dose group and the low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human breast cancer MDA-MB-231 in nude mice is shown in Table 11. The inhibition rate of avastin on heterotransplanted human breast cancer MDA-MB-231 in nude mice was 68.95% and the body weight of mice showed no obvious change; the inhibition rates of polypeptide III at high, medium and low doses on heterotransplanted human breast cancer MDA-MB-231 in nude mice were 58.82%, 72.86% and 61.91% respectively. The tumor volume of mice from both the high-dose group and the low-dose group presented significant difference in contrast with that from the negative control group; the tumor volume of mice from the medium-dose group presented extremely significant difference in contrast with that from the negative control group; meanwhile, animals from the experimental groups showed no significant change in body weight, and no obvious toxic and side effects were observed in contrast with the negative control group.

Embodiment 7

Test on the Inhibition Effect of Integrin-Blocking Polypeptide I, Polypeptide II and Polypeptide III on Heterotransplanted Human Gastric Cancer MGC-803 in Nude Mice The tumor inoculation process and analysis methods were the same as those mentioned in embodiment 6. Oxaliplatin and xeloda were adopted to set up the positive control group, administering oxaliplatin once every four days through tail vein injection and xeloda once the other day through oral gavage; drugs of all other groups were administered on daily basis through tail vein injection.

TABLE 12 inhibition effect of polypeptide I on heterotransplanted human gastric cancer MGC-803 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.00 ± 0.52 | 12 | 23.33 ± 0.44 | 12 | 0.78 ± 0.22 | — |
| oxaliplatin + xeloda | oxaliplatin 3.3 mg/kg xeloda 35 mg/kg | 20.09 ± 0.70 | 8 | 20.47 ± 0.70 | 6 | 0.32 ± 0.13* | 51.76% |
| polypeptide I (high) | 3 | 20.18 ± 0.61 | 8 | 23.23 ± 0.67 | 7 | 0.48 ± 0.13 | 38.28% |
| polypeptide I (medium) | 1.5 | 20.02 ± 0.52 | 8 | 22.66 ± 0.61 | 8 | 0.42 ± 0.10 | 38.46% |
| polypeptide I (low) | 0.75 | 20.14 ± 0.52 | 8 | 22.98 ± 0.60 | 8 | 0.50 ± 0.13 | 35.90% |

TABLE 13 inhibition effect of polypeptide II on heterotransplanted human gastric cancer MGC-803 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.29 ± 1.29 | 12 | 22.08 ± 1.88 | 12 | 0.78 ± 0.22 | — |
| oxaliplatin + xeloda | oxaliplatin 3.3 mg/kg xeloda 35 mg/kg | 20.20 ± 0.75 | 10 | 17.50 ± 1.95 | 9 | 0.32 ± 0.13* | 51.76% |
| polypeptide II (high) | 3 | 19.95 ± 1.21 | 10 | 19.60 ± 1.26 | 10 | 0.48 ± 0.13 | 38.28% |

TABLE 13-continued inhibition effect of polypeptide II on heterotransplanted human gastric cancer MGC-803 in nude mice

| group | dose (mg/kg/time) | initial weight (g) | initial number | final weight (g) | final number | tumor weight (g) | tumor inhibition rate |
|---|---|---|---|---|---|---|---|
| polypeptide II (medium) | 1.5 | 20.15 ± 0.97 | 10 | 19.67 ± 1.41 | 10 | 0.16 ± 0.10** | 79.72% |
| polypeptide II (low) | 0.75 | 20.00 ± 1.22 | 10 | 20.40 ± 1.26 | 10 | 0.23 ± 0.13** | 70.67% |

TABLE 14 inhibition effect of polypeptide III on heterotransplanted human gastric cancer MGC-803 in nude mice

| group | dose (mg/kg/time) | initial weight (g) | initial number | final weight (g) | final number | Tumor weight (g) | tumor inhibition rate |
|---|---|---|---|---|---|---|---|
| control | — | 20.29 ± 1.29 | 12 | 22.08 ± 1.88 | 12 | 0.78 ± 0.22 | — |
| oxaliplatin + xeloda | oxaliplatin 3.3 mg/kg xeloda 35 mg/kg | 20.20 ± 0.75 | 10 | 17.50 ± 1.95 | 9 | 0.32 ± 0.13* | 51.76% |
| polypeptide III(high) | 0.75 | 19.75 ± 0.65 | 10 | 20.88 ± 0.85 | 10 | 0.33 ± 0.09 | 57.65% |
| polypeptide III(medium) | 0.375 | 19.63 ± 0.75 | 10 | 20.13 ± 1.03 | 10 | 0.27 ± 0.06* | 66.03% |
| polypeptide III(low) | 0.1875 | 20.25 ± 0.65 | 10 | 22.25 ± 1.71 | 10 | 0.23 ± 0.05** | 70.08% |

RESULTS: The inhibition effect of polypeptide I on heterotransplanted human gastric cancer MGC-803 in nude mice is shown in Table 12. The inhibition rate of the oxaliplatin+xeloda group on heterotransplanted human gastric cancer MGC-803 in nude mice was 51.76%; however, this combination chemotherapy greatly reduced the body weight of animals; mice treated in this way showed lighter body weight and more apparent toxic and side effects than those from the negative control group. The inhibition rates of polypeptide I at high, medium and low doses on heterotransplanted human gastric cancer MGC-803 in nude mice were 38.28%, 38.46% and 35.90% respectively; meanwhile, animals from the polypeptide groups showed no significant change in body weight, and no obvious toxic and side effects were observed in contrast with the negative control group.

The inhibition effect of polypeptide II on heterotransplanted human gastric cancer MGC-803 in nude mice is shown in Table 13. The inhibition rate of the oxaliplatin+xeloda group on heterotransplanted human gastric cancer MGC-803 in nude mice was 51.76%; however, this combination chemotherapy greatly reduced the body weight of animals; mice treated in this way showed lighter body weight and more apparent toxic and side effects than those from the negative control group. The inhibition rates of polypeptide II at high, medium and low doses on heterotransplanted human gastric cancer MGC-803 in nude mice were 38.28%, 79.72% and 70.67% respectively. The tumor volume of mice from both the medium-dose group and the low-dose group exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human gastric cancer MGC-803 in nude mice is shown in Table 14. The inhibition rate of the oxaliplatin+xeloda group on heterotransplanted human gastric cancer MGC-803 in nude mice was 51.76%; however, this combination chemotherapy greatly reduced the body weight of animals; mice treated in this way showed lighter body weight and more apparent toxic and side effects than those from the negative control group. The inhibition rates of polypeptide III at high, medium and low doses on heterotransplanted human gastric cancer MGC-803 in nude mice were 57.65%, 66.03% and 70.08% respectively. The tumor volume of mice from the medium-dose group presented significant difference in contrast with that from the negative control group; the tumor volume of mice from the low-dose group presented extremely significant difference in contrast with that from the negative control group; meanwhile, animals from the polypeptide groups showed no significant change in body weight, and no obvious toxic and side effects were observed in contrast with the negative control group.

Embodiment 8

Test on the Inhibition Effect of Integrin-Blocking Polypeptide I, Polypeptide II and Polypeptide III on Heterotransplanted Human Lung Cancer H460 in Nude Mice The tumor inoculation process and analysis methods were the same as those mentioned in embodiment 6. Taxol used in the positive control group was administered once every 3 days through tail vein injection, while drugs of all other groups were administered on daily basis through tail vein injection.

TABLE 15 inhibition effect of polypeptide I on heterotransplanted human lung cancer H460 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.99 ± 0.72 | 12 | 23.13 ± 0.51 | 12 | 0.88 ± 0.23 | — |
| taxol | 10 | 20.13 ± 0.57 | 8 | 17.80 ± 0.63 | 7 | 0.28 ± 0.07** | 68.21% |
| polypeptide I (high) | 3 | 19.94 ± 0.65 | 8 | 22.96 ± 0.69 | 8 | 0.47 ± 0.17* | 46.60% |
| polypeptide I (medium) | 1.5 | 20.05 ± 0.52 | 8 | 22.93 ± 0.51 | 8 | 0.40 ± 0.05** | 54.54% |
| polypeptide I (low) | 0.75 | 19.91 ± 0.57 | 8 | 23.13 ± 0.58 | 8 | 0.51 ± 0.17* | 42.05% |

TABLE 16 inhibition effect of polypeptide II on heterotransplanted human lung cancer H460 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.13 ± 0.61 | 12 | 23.07 ± 0.53 | 12 | 0.88 ± 0.23 | — |
| taxol | 10 | 20.05 ± 0.68 | 8 | 18.09 ± 0.55 | 7 | 0.28 ± 0.07** | 68.21% |
| polypeptide II (high) | 3 | 20.21 ± 0.57 | 8 | 22.59 ± 0.53 | 8 | 0.37 ± 0.17* | 57.68% |
| polypeptide II (medium) | 1.5 | 20.06 ± 0.47 | 8 | 23.26 ± 0.40 | 8 | 0.30 ± 0.05** | 65.37% |
| polypeptide II (low) | 0.75 | 20.02 ± 0.51 | 8 | 22.87 ± 0.40 | 8 | 0.41 ± 0.17* | 53.49% |

TABLE 17 inhibition effect of polypeptide III on heterotransplanted human lung cancer H460 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.13 ± 0.61 | 12 | 23.07 ± 0.53 | 12 | 0.88 ± 0.23 | — |
| taxol | 10 | 20.05 ± 0.68 | 8 | 18.09 ± 0.55 | 7 | 0.28 ± 0.07** | 68.21% |
| polypeptide III(high) | 0.75 | 20.14 ± 0.64 | 8 | 23.14 ± 0.51 | 8 | 0.28 ± 0.11** | 68.05% |
| polypeptide III(medium) | 0.375 | 19.89 ± 0.62 | 8 | 23.12 ± 0.53 | 8 | 0.23 ± 0.06** | 74.42% |
| polypeptide III(low) | 0.1875 | 20.36 ± 0.68 | 8 | 23.15 ± 0.49 | 8 | 0.27 ± 0.05** | 69.23% |

RESULTS: the inhibition effect of polypeptide I on heterotransplanted human lung cancer H460 in nude mice is shown in Table 15. The inhibition rate of the taxol group on heterotransplanted human lung cancer H460 in nude mice was 68.21%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human lung cancer H460 in nude mice were 46.60%, 54.54% and 42.05% respectively. The tumor volume of mice from both the high-dose group and the low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human lung cancer H460 in nude mice is shown in Table 16. The inhibition rate of the taxol group on heterotransplanted human lung cancer H460 in nude mice was 68.21%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human lung cancer H460 in nude mice were 57.68%, 65.37% and 53.49% respectively. The tumor volume of mice from both the high-dose group and the low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human lung cancer H460 in nude mice is shown in Table 17. The inhibition rate of the taxol group on heterotransplanted human lung cancer H460 in nude mice was 68.21%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human lung cancer H460 in nude mice were 68.05%, 74.42% and 69.23% respectively. All polypeptide groups, including the high-dose group, the medium-dose group and the low-dose group, presented extremely significant difference in contrast with the negative control group; meanwhile, animals from the polypeptide groups showed no significant change in body weight, and no obvious toxic and side effects were observed in contrast with the negative control group.

Embodiment 9

Test on the Inhibition Effect of Integrin-Blocking Polypeptide I, Polypeptide II and Polypeptide III on Heterotransplanted Human Liver Cancer SMMC-7721 in Nude Mice The tumor inoculation process and analysis methods were the same as those mentioned in embodiment 6. Taxol used in the positive control group was administered once every 3 days through tail vein injection, while drugs of all other groups were administered on daily basis through tail vein injection.

TABLE 18 inhibition effect of polypeptide I on heterotransplanted human liver cancer SMMC-7721 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.77 ± 0.61 | 12 | 23.04 ± 0.61 | 12 | 1.27 ± 0.23 | — |
| taxol | 10 | 20.11 ± 0.52 | 8 | 17.22 ± 0.51 | 7 | 0.28 ± 0.05** | 78.10% |
| endostar (rh-endostatin) | 2.5 | 19.83 ± 0.49 | 8 | 23.04 ± 0.68 | 8 | 0.79 ± 0.29 | 36.96% |
| polypeptide I (high) | 3 | 20.18 ± 0.62 | 8 | 22.84 ± 0.55 | 8 | 0.55 ± 0.12* | 56.70% |
| polypeptide I (medium) | 1.5 | 20.23 ± 0.67 | 8 | 22.99 ± 0.55 | 8 | 0.47 ± 0.14** | 63.00% |
| polypeptide I (low) | 0.75 | 19.93 ± 0.54 | 8 | 23.17 ± 0.63 | 8 | 0.53 ± 0.04* | 58.26% |

TABLE 19 inhibition effect of polypeptide II on heterotransplanted human liver cancer SMMC-7721 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.83 ± 0.61 | 12 | 23.26 ± 0.55 | 12 | 1.27 ± 0.23 | — |
| taxol | 10 | 19.81 ± 0.54 | 8 | 16.90 ± 0.51 | 7 | 0.28 ± 0.05** | 78.10% |
| endostar (rh-endostatin) | 2.5 | 19.73 ± 0.50 | 8 | 23.02 ± 0.62 | 8 | 0.79 ± 0.29 | 36.96% |
| polypeptide II (high) | 3 | 19.87 ± 0.66 | 8 | 22.90 ± 0.59 | 8 | 0.39 ± 0.05** | 68.75% |
| polypeptide II (medium) | 1.5 | 20.15 ± 0.56 | 8 | 22.93 ± 0.60 | 8 | 0.31 ± 0.07** | 75.12% |
| polypeptide II (low) | 0.75 | 20.10 ± 0.39 | 8 | 23.21 ± 0.60 | 8 | 0.36 ± 0.05** | 71.54% |

TABLE 20 inhibition effect of polypeptide III on heterotransplanted human liver cancer SMMC-7721 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.83 ± 0.61 | 12 | 23.26 ± 0.55 | 12 | 1.27 ± 0.23 | — |
| taxol | 10 | 19.81 ± 0.54 | 8 | 16.90 ± 0.51 | 7 | 0.28 ± 0.05** | 78.10% |
| endostar (rh-endostatin) | 2.5 | 19.73 ± 0.50 | 8 | 23.02 ± 0.62 | 8 | 0.79 ± 0.29 | 36.96% |
| polypeptide III(high) | 0.75 | 19.89 ± 0.72 | 8 | 22.63 ± 0.39 | 8 | 0.28 ± 0.03** | 77.55% |
| polypeptide III(medium) | 0.375 | 19.97 ± 0.50 | 8 | 23.25 ± 0.54 | 8 | 0.22 ± 0.03** | 82.55% |

TABLE 20-continued inhibition effect of polypeptide III on heterotransplanted
human liver cancer SMMC-7721 in nude mice

| group | dose (mg/kg/ time) | initial weight (g) | initial number | final weight (g) | final number | tumor weight (g) | tumor inhibition rate |
|---|---|---|---|---|---|---|---|
| polypeptide III(low) | 0.1875 | 19.91 ± 0.46 | 8 | 22.70 ± 0.57 | 8 | 0.35 ± 0.04** | 71.85% |

RESULTS: the inhibition effect of polypeptide I on heterotransplanted human liver cancer SMMC-7721 in nude mice is shown in Table 18. The inhibition rate of the taxol group on heterotransplanted human liver cancer SMMC-7721 in nude mice was 78.10%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human liver cancer SMMC-7721 in nude mice were 56.70, 63.00% and 58.26% respectively. The tumor volume of mice from both the high-dose group and the low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human liver cancer SMMC-7721 in nude mice is shown in Table 19. The inhibition rate of the taxol group on heterotransplanted human liver cancer SMMC-7721 in nude mice was 78.10%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human liver cancer SMMC-7721 in nude mice were 68.75%, 75.12% and 71.54% respectively. All polypeptide groups, including the high-dose group, the medium-dose group and the low-dose group, presented extremely significant difference in contrast with the negative control group; meanwhile, animals from the polypeptide groups showed no significant change in body weight, and no obvious toxic and side effects were observed in contrast with the negative control group.

The inhibition effect of polypeptide III on heterotransplanted human liver cancer SMMC-7721 in nude mice is shown in Table 20. The inhibition rate of the taxol group on heterotransplanted human liver cancer SMMC-7721 in nude mice was 78.10%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human liver cancer SMMC-7721 in nude mice were 77.55%, 82.55% and 71.85% respectively. All polypeptide groups, including the high-dose group, the medium-dose group and the low-dose group, presented extremely significant difference in contrast with the negative control group; meanwhile, animals from the polypeptide groups showed no significant change in body weight, and no obvious toxic and side effects were observed in contrast with the negative control group.

Embodiment 10

Test on the Inhibition Effect of Integrin-Blocking Polypeptide I, Polypeptide II and Polypeptide III on Heterotransplanted Human Cervical Cancer HeLa in Nude Mice The tumor inoculation process and analysis methods were the same as those mentioned in embodiment 6. Cisplatin used in the positive control group was administered once every 3 days through tail vein injection, while drugs of all other groups were administered on daily basis through tail vein injection.

TABLE 21 inhibition effect of polypeptide I on heterotransplanted
human cervical cancer HeLa in nude mice

| group | dose (mg/kg/ time) | initial weight (g) | initial number | final weight (g) | final number | tumor weight (g) | tumor inhibition rate |
|---|---|---|---|---|---|---|---|
| control | — | 20.00 ± 0.52 | 12 | 23.33 ± 0.44 | 12 | 1.40 ± 0.37 | — |
| cisplatin | 10 | 20.09 ± 0.70 | 8 | 20.47 ± 0.70 | 6 | 0.38 ± 0.10** | 73.13% |
| endostar (rh-endostatin) | 2.5 | 20.18 ± 0.61 | 8 | 23.23 ± 0.67 | 7 | 0.80 ± 0.20 | 43.08% |
| polypeptide I (high) | 3 | 20.07 ± 0.53 | 8 | 23.18 ± 0.51 | 8 | 0.52 ± 0.05** | 62.85% |
| polypeptide I (medium) | 1.5 | 20.17 ± 0.48 | 8 | 22.96 ± 0.57 | 8 | 0.41 ± 0.07** | 70.71% |
| polypeptide I (low) | 0.75 | 19.62 ± 0.52 | 8 | 22.94 ± 0.46 | 8 | 0.49 ± 0.05** | 65.00% |

TABLE 22 inhibition effect of polypeptide II on heterotransplanted human cervical cancer HeLa in nude mice

| group | dose (mg/kg/time) | initial weight (g) | initial number | final weight (g) | final number | tumor weight (g) | tumor inhibition rate |
|---|---|---|---|---|---|---|---|
| control | — | 20.05 ± 0.58 | 12 | 23.12 ± 0.57 | 12 | 1.40 ± 0.37 | — |
| cisplatin | 10 | 20.16 ± 0.54 | 8 | 17.28 ± 0.56 | 7 | 0.38 ± 0.10** | 73.13% |
| endostar (rh-endostatin) | 2.5 | 19.84 ± 0.55 | 8 | 23.14 ± 0.54 | 8 | 0.80 ± 0.20 | 43.08% |
| polypeptide II (high) | 3 | 19.92 ± 0.75 | 8 | 22.99 ± 0.52 | 8 | 0.62 ± 0.18* | 55.82% |
| polypeptide II (medium) | 1.5 | 20.12 ± 0.63 | 8 | 22.88 ± 0.55 | 8 | 0.45 ± 0.11** | 68.19% |
| polypeptide II (low) | 0.75 | 20.03 ± 0.57 | 8 | 23.14 ± 0.55 | 8 | 0.50 ± 0.12** | 64.45% |

TABLE 23 inhibition effect of polypeptide III on heterotransplanted human cervical cancer HeLa in nude mice

| group | dose (mg/kg/time) | initial weight (g) | initial number | final weight (g) | final number | tumor weight (g) | tumor inhibition rate |
|---|---|---|---|---|---|---|---|
| control | — | 20.05 ± 0.58 | 12 | 23.12 ± 0.57 | 12 | 1.40 ± 0.37 | — |
| cisplatin | 10 | 20.16 ± 0.54 | 8 | 17.28 ± 0.56 | 7 | 0.38 ± 0.10** | 73.13% |
| endostar (rh-endostatin) | 2.5 | 19.84 ± 0.55 | 8 | 23.14 ± 0.54 | 8 | 0.80 ± 0.20 | 43.08% |
| polypeptide III(high) | 0.75 | 19.76 ± 0.43 | 8 | 22.88 ± 0.66 | 8 | 0.50 ± 0.15** | 64.35% |
| Polypeptide III(medium) | 0.375 | 20.19 ± 0.60 | 8 | 23.17 ± 0.58 | 8 | 0.39 ± 0.08** | 72.41% |
| polypeptide III(low) | 0.1875 | 19.98 ± 0.65 | 8 | 23.10 ± 0.56 | 8 | 0.44 ± 0.11** | 68.68% |

RESULTS: the inhibition effect of polypeptide I on heterotransplanted human cervical cancer HeLa in nude mice is shown in Table 21. The inhibition rate of the cisplatin group on heterotransplanted human cervical cancer HeLa in nude mice was 73.13%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human cervical cancer HeLa in nude mice were 62.85%, 70.71% and 65.00% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human cervical cancer HeLa in nude mice is shown in Table 22. The inhibition rate of the cisplatin group on heterotransplanted human cervical cancer HeLa in nude mice was 73.13%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human cervical cancer HeLa in nude mice were 55.82%, 68.19% and 64.45% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human cervical cancer HeLa in nude mice is shown in Table 23. The inhibition rate of the cisplatin group on heterotransplanted human cervical cancer HeLa in nude mice was 73.13%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human cervical cancer HeLa in nude mice were 64.35%, 72.41% and 68.68% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 11

Test on the Inhibition Effect of Integrin-Blocking Polypeptide I, Polypeptide II and Polypeptide III on Heterotransplanted Human Endometrial Cancer HHUA in Nude Mice The tumor inoculation process and analysis methods were the same as those mentioned in embodiment 6. Taxol used in the positive control group was administered once every 3 days through tail vein injection, while drugs of all other groups were administered on daily basis through tail vein injection.

RESULTS: the inhibition effect of polypeptide I on heterotransplanted human endometrial cancer HHUA in nude mice is shown in Table 24. The inhibition rate of the taxol group on heterotransplanted human endometrial cancer HHUA in nude mice was 79.82%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human endometrial cancer HHUA in nude mice were 47.36%, 55.30% and 54.39% respectively.

TABLE 24 inhibition effect of polypeptide I on heterotransplanted human endometrial cancer HHUA in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.66 | 12 | 23.01 ± 0.48 | 12 | 1.14 ± 0.35 | — |
| taxol | 10 | 20.94 ± 0.58 | 8 | 18.88 ± 0.68 | 7 | 0.23 ± 0.07** | 79.82% |
| endostar (rh-endostatin) | 2.5 | 20.88 ± 0.79 | 8 | 22.89 ± 0.51 | 8 | 0.65 ± 0.15 | 43.00% |
| polypeptide I (high) | 3 | 19.82 ± 0.60 | 8 | 23.14 ± 0.48 | 8 | 0.60 ± 0.14 | 47.36% |
| polypeptide I (medium) | 1.5 | 19.96 ± 0.58 | 8 | 22.93 ± 0.56 | 8 | 0.51 ± 0.10* | 55.30% |
| polypeptide I (low) | 0.75 | 19.87 ± 0.58 | 8 | 22.81 ± 0.60 | 8 | 0.52 ± 0.12* | 54.39% |

TABLE 25 inhibition effect of polypeptide II on heterotransplanted human endometrial cancer HHUA in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.66 | 12 | 23.01 ± 0.48 | 12 | 1.14 ± 0.35 | — |
| taxol | 10 | 20.94 ± 0.58 | 8 | 18.88 ± 0.68 | 7 | 0.23 ± 0.07** | 79.82% |
| endostar (rh-endostatin) | 2.5 | 20.88 ± 0.79 | 8 | 22.89 ± 0.51 | 8 | 0.65 ± 0.15 | 43.00% |
| polypeptide II (high) | 3 | 20.08 ± 0.59 | 8 | 23.04 ± 0.55 | 8 | 0.46 ± 0.11** | 59.65% |
| polypeptide II (medium) | 1.5 | 19.70 ± 0.52 | 8 | 22.95 ± 0.46 | 8 | 0.37 ± 0.07** | 67.54% |
| polypeptide II (low) | 0.75 | 20.28 ± 0.61 | 8 | 22.93 ± 0.46 | 8 | 0.41 ± 0.11** | 64.03% |

TABLE 26 inhibition effect of polypeptide III on heterotransplanted human endometrial cancer HHUA in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.66 | 12 | 23.01 ± 0.48 | 12 | 1.14 ± 0.35 | — |
| taxol | 10 | 20.94 ± 0.58 | 8 | 18.88 ± 0.68 | 7 | 0.23 ± 0.07** | 79.82% |
| endostar (rh-endostatin) | 2.5 | 19.88 ± 0.79 | 8 | 22.89 ± 0.51 | 8 | 0.65 ± 0.15 | 43.00% |
| polypeptide III (high) | 0.75 | 19.89 ± 0.53 | 8 | 23.07 ± 0.56 | 8 | 0.38 ± 0.10** | 66.67% |
| polypeptide III (medium) | 0.375 | 20.31 ± 0.51 | 8 | 23.18 ± 0.57 | 8 | 0.30 ± 0.06** | 73.21% |
| polypeptide III (low) | 0.1875 | 19.74 ± 0.55 | 8 | 22.92 ± 0.57 | 8 | 0.33 ± 0.07** | 70.53% |

The tumor volume of mice from both the medium-dose group and the low-dose group exhibited significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human endometrial cancer HHUA in nude mice is shown in Table 25. The inhibition rate of the taxol group on heterotransplanted human endometrial cancer HHUA in nude mice was 79.82%, however, this chemotherapy greatly reduced the body weight of animals; mice treated in this way showed lighter body weight and more apparent toxic and side effects than that from the negative control group and the polypeptide groups. The inhibition rates of polypeptide II at high, medium and low doses on heterotransplanted human endometrial cancer HHUA in nude mice were 59.65%, 67.54% and 64.03% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human endometrial cancer HHUA in nude mice is shown in Table 26. The inhibition rate of the taxol group on heterotransplanted human endometrial cancer HHUA in nude mice was 73.13%, however, this chemotherapy greatly reduced the body weight of animals; mice treated in this way showed lighter body weight and more apparent toxic and side effects than those from the negative control group and the polypeptide groups. The inhibition rates of polypeptide IIIat high, medium and low doses on heterotransplanted human endometrial cancer HHUA in nude mice were 66.67%, 73.21% and 70.53% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 12

Test on the Inhibition Effect of Integrin-Blocking Polypeptide I, Polypeptide II and Polypeptide III on Heterotransplanted Human Prostate Cancer DU-145 in Nude Mice The tumor inoculation process and analysis methods were the same as those mentioned in embodiment 6. Cisplatin used in the positive control group was administered once every 3 days through tail vein injection, while drugs of all other groups were administered on daily basis through tail vein injection.

TABLE 27 inhibition effect of polypeptide I on heterotransplanted human prostate cancer DU-145 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.77 ± 0.61 | 12 | 23.04 ± 0.61 | 12 | 1.43 ± 0.34 | — |
| cisplatin | 10 | 20.11 ± 0.52 | 8 | 17.22 ± 0.51 | 7 | 0.37 ± 0.10** | 73.84% |
| endostar (rh-endostatin) | 2.5 | 19.83 ± 0.49 | 8 | 23.04 ± 0.68 | 8 | 0.86 ± 0.16 | 38.46% |
| polypeptide I (high) | 3 | 19.88 ± 0.58 | 8 | 22.99 ± 0.37 | 8 | 0.48 ± 0.10** | 66.43% |
| polypeptide I (medium) | 1.5 | 19.97 ± 0.66 | 8 | 23.10 ± 0.61 | 8 | 0.40 ± 0.16** | 72.02% |
| polypeptide I (low) | 0.75 | 20.07 ± 0.54 | 8 | 22.85 ± 0.61 | 8 | 0.46 ± 0.14** | 67.83% |

TABLE 28 inhibition effect of polypeptide II on heterotransplanted human prostate cancer DU-145 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.77 ± 0.61 | 12 | 23.04 ± 0.61 | 12 | 1.43 ± 0.34 | — |
| cisplatin | 10 | 20.11 ± 0.52 | 8 | 17.22 ± 0.51 | 7 | 0.37 ± 0.10** | 73.84% |
| endostar (rh-endostatin) | 2.5 | 19.83 ± 0.49 | 8 | 23.04 ± 0.68 | 8 | 0.86 ± 0.16 | 38.46% |
| polypeptide II (high) | 3 | 19.63 ± 0.49 | 8 | 22.99 ± 0.55 | 8 | 0.65 ± 0.14* | 54.25% |
| polypeptide II (medium) | 1.5 | 20.08 ± 0.46 | 8 | 23.04 ± 0.48 | 8 | 0.46 ± 0.10** | 67.83% |
| polypeptide II (low) | 0.75 | 20.31 ± 0.60 | 8 | 23.10 ± 0.48 | 8 | 0.53 ± 0.12** | 62.92% |

TABLE 29 inhibition effect of polypeptide III on heterotransplanted human prostate cancer DU-145 in nude mice

| group | dose (mg/kg/ time) | initial weight (g) | initial number | final weight (g) | final number | tumor weight (g) | tumor inhibition rate |
|---|---|---|---|---|---|---|---|
| control | 10 | 19.77 ± 0.61 | 12 | 23.04 ± 0.61 | 12 | 1.43 ± 0.34 | — |
| cisplatin | 5 | 20.11 ± 0.52 | 8 | 17.22 ± 0.51 | 7 | 0.37 ± 0.10** | 73.84% |
| endostar (rh-endostatin) | 2.5 | 19.83 ± 0.49 | 8 | 23.04 ± 0.68 | 8 | 0.86 ± 0.16 | 38.46% |
| polypeptide III (high) | 0.75 | 20.18 ± 0.62 | 8 | 22.84 ± 0.55 | 8 | 0.56 ± 0.14** | 60.73% |
| polypeptide III (medium) | 0.375 | 20.23 ± 0.67 | 8 | 22.99 ± 0.55 | 8 | 0.43 ± 0.13** | 69.90% |
| polypeptide III (low) | 0.1875 | 19.93 ± 0.54 | 8 | 23.17 ± 0.63 | 8 | 0.51 ± 0.15** | 64.08% |

RESULTS: the inhibition effect of polypeptide I on heterotransplanted human prostate cancer DU-145 in nude mice is shown in Table 27. The inhibition rate of the cisplatin group on heterotransplanted human prostate cancer DU-145 in nude mice was 73.84%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human prostate cancer DU-145 in nude mice were 66.43%, 72.02% and 67.83% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human prostate cancer DU-145 in nude mice is shown in Table 28. The inhibition rate of the cisplatin group on heterotransplanted human prostate cancer DU-145 in nude mice was 73.84%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human prostate cancer DU-145 in nude mice were 54.25%, 67.83% and 62.92% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human prostate cancer DU-145 in nude mice is shown in Table 29. The inhibition rate of the cisplatin group on heterotransplanted human prostate cancer DU-145 in nude mice was 73.84%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human prostate cancer DU-145 in nude mice were 60.73%, 69.90% and 64.08% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 13

Test on the Inhibition Effect of Integrin-Blocking Polypeptide I, Polypeptide II and Polypeptide III on Heterotransplanted Human Testicular Cancer 5637 in Nude Mice The tumor inoculation process and analysis methods were the same as those mentioned in embodiment 6. 5-fluorouracil (5-FU) used in the positive control group was administered once every 3 days through tail vein injection, while drugs of all other groups were administered on daily basis through tail vein injection.

TABLE 30 inhibition effect of polypeptide I on heterotransplanted human testicular cancer 5637 in nude mice

| group | dose (mg/kg/ time) | initial weight (g) | initial number | final weight (g) | final number | tumor weight (g) | tumor inhibition rate |
|---|---|---|---|---|---|---|---|
| control | — | 20.09 ± 0.65 | 12 | 23.11 ± 0.61 | 12 | 1.26 ± 0.29 | — |
| 5-Fu | 10 | 19.90 ± 0.48 | 8 | 17.03 ± 0.53 | 7 | 0.28 ± 0.06** | 77.80% |
| endostar (rh-endostatin) | 2.5 | 20.00 ± 0.70 | 8 | 22.98 ± 0.72 | 8 | 0.76 ± 0.21 | 39.49% |

TABLE 30-continued inhibition effect of polypeptide I on heterotransplanted human testicular cancer 5637 in nude mice

| group | dose (mg/kg/ time) | initial weight (g) | initial number | final weight (g) | final number | tumor weight (g) | tumor inhibition rate |
|---|---|---|---|---|---|---|---|
| polypeptide I (high) | 3 | 19.83 ± 0.49 | 8 | 23.04 ± 0.68 | 8 | 0.57 ± 0.11* | 54.76% |
| polypeptide I (medium) | 1.5 | 19.63 ± 0.49 | 8 | 22.99 ± 0.55 | 8 | 0.46 ± 0.10** | 63.49% |
| polypeptide I (low) | 0.75 | 20.08 ± 0.46 | 8 | 23.04 ± 0.48 | 8 | 0.55 ± 0.11* | 56.34% |

TABLE 31 inhibition effect of polypeptide II on heterotransplanted human testicular cancer 5637 in nude mice

| group | dose (mg/kg/ time) | initial weight (g) | initial number | final weight (g) | final number | tumor weight (g) | tumor inhibition rate |
|---|---|---|---|---|---|---|---|
| control | — | 20.09 ± 0.65 | 12 | 23.11 ± 0.61 | 12 | 1.26 ± 0.29 | — |
| 5-Fu | 10 | 19.90 ± 0.48 | 8 | 17.03 ± 0.53 | 7 | 0.28 ± 0.06** | 77.80% |
| endostar (rh-endostatin) | 2.5 | 20.00 ± 0.70 | 8 | 22.98 ± 0.72 | 8 | 0.76 ± 0.21 | 39.49% |
| polypeptide II (high) | 3 | 20.03 ± 0.61 | 8 | 23.16 ± 0.51 | 8 | 0.60 ± 0.16* | 52.49% |
| polypeptide II (medium) | 1.5 | 20.05 ± 0.58 | 8 | 22.96 ± 0.59 | 8 | 0.45 ± 0.10** | 64.32% |
| polypeptide II (low) | 0.75 | 19.97 ± 0.62 | 8 | 23.09 ± 0.59 | 8 | 0.49 ± 0.11** | 60.96% |

TABLE 32 inhibition effect of polypeptide III on heterotransplanted human testicular cancer 5637 in nude mice

| group | dose (mg/kg/ time) | initial weight (g) | initial number | final weight (g) | final number | tumor weight (g) | tumor inhibition rate |
|---|---|---|---|---|---|---|---|
| control | — | 20.09 ± 0.65 | 12 | 23.11 ± 0.61 | 12 | 1.26 ± 0.29 | — |
| 5-Fu | 10 | 19.90 ± 0.48 | 8 | 17.03 ± 0.53 | 7 | 0.28 ± 0.06** | 77.80% |
| endostar (rh-endostatin) | 2.5 | 20.00 ± 0.70 | 8 | 22.98 ± 0.72 | 8 | 0.76 ± 0.21 | 39.49% |
| polypeptide III (high) | 0.75 | 19.96 ± 0.57 | 8 | 23.12 ± 0.73 | 8 | 0.50 ± 0.10** | 60.51% |
| polypeptide III (medium) | 0.375 | 20.03 ± 0.60 | 8 | 23.35 ± 0.50 | 8 | 0.44 ± 0.12** | 65.11% |
| polypeptide III (low) | 0.1875 | 19.89 ± 0.57 | 8 | 23.02 ± 0.64 | 8 | 0.47 ± 0.12** | 62.63% |

RESULTS: the inhibition effect of polypeptide I on heterotransplanted human testicular cancer 5637 in nude mice is shown in Table 30. The inhibition rate of the 5-FU group on heterotransplanted human testicular cancer 5637 in nude mice was 77.80%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human testicular cancer 5637 in nude mice were 54.76%, 63.49% and 56.34% respectively. The tumor volume of mice from both the high-dose group and low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human testicular cancer 5637 in nude mice is shown in Table 31. The inhibition rate of the 5-FU group on heterotransplanted human testicular cancer 5637 in nude mice was 77.80%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human testicular cancer 5637 in nude mice were 52.49%, 64.32% and 60.96% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human testicular cancer 5637 in nude mice is shown in Table 32. The inhibition rate of the 5-FU group on heterotransplanted human testicular cancer 5637 in nude mice was 73.84%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human testicular cancer 5637 in nude mice were 60.51%, 65.11% and 62.63% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 14

Test on the Inhibition Effect of Integrin-Blocking Polypeptide I, Polypeptide II and Polypeptide III on Heterotransplanted Human Gallbladder Cancer GBC-SD in Nude Mice The tumor inoculation process and analysis methods were the same as those mentioned in embodiment 6. Avastin used in the positive control group was administered once every 2 days through tail vein injection, while drugs of all other groups were administered on daily basis through tail vein injection.

TABLE 33 inhibition effect of polypeptide I on heterotransplanted human gallbladder cancer GBC-SD in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.34 | 12 | 23.11 ± 0.70 | 12 | 1.20 ± 0.30 | — |
| avastin | 10 | 20.13 ± 0.65 | 8 | 20.89 ± 0.61 | 7 | 0.25 ± 0.06** | 78.85% |
| endostar (rh-endostatin) | 2.5 | 20.11 ± 0.59 | 8 | 23.13 ± 0.38 | 7 | 0.71 ± 0.15 | 40.83% |
| Polypeptide I (high) | 3 | 20.88 ± 0.79 | 8 | 22.89 ± 0.51 | 8 | 0.50 ± 0.11* | 58.33% |
| Polypeptide I (medium) | 1.5 | 20.08 ± 0.59 | 8 | 23.04 ± 0.55 | 8 | 0.42 ± 0.10** | 65.00% |
| Polypeptide I (low) | 0.75 | 19.70 ± 0.52 | 8 | 22.95 ± 0.46 | 8 | 0.52 ± 0.11* | 56.67% |

TABLE 34 inhibition effect of polypeptide II on heterotransplanted human gallbladder cancer GBC-SD in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.34 | 12 | 23.11 ± 0.70 | 12 | 1.20 ± 0.30 | — |
| avastin | 10 | 20.13 ± 0.65 | 8 | 20.89 ± 0.61 | 7 | 0.25 ± 0.06** | 78.85% |
| endostar (rh-endostatin) | 2.5 | 20.11 ± 0.59 | 8 | 23.13 ± 0.38 | 7 | 0.71 ± 0.15 | 40.83% |
| polypeptide II (high) | 3 | 20.06 ± 0.63 | 8 | 23.10 ± 0.64 | 8 | 0.47 ± 0.11* | 60.48% |
| polypeptide II (medium) | 1.5 | 19.80 ± 0.39 | 8 | 22.99 ± 0.51 | 8 | 0.37 ± 0.10** | 69.19% |
| polypeptide II (low) | 0.75 | 20.01 ± 0.51 | 8 | 22.76 ± 0.51 | 8 | 0.46 ± 0.11* | 62.00% |

TABLE 35 inhibition effect of polypeptide III on heterotransplanted human gallbladder cancer GBC-SD in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.34 | 12 | 23.11 ± 0.70 | 12 | 1.20 ± 0.30 | — |
| avastin | 10 | 20.13 ± 0.65 | 8 | 20.89 ± 0.61 | 7 | 0.25 ± 0.06** | 78.85% |

TABLE 35-continued inhibition effect of polypeptide III on heterotransplanted
human gallbladder cancer GBC-SD in nude mice

| group | dose (mg/kg/time) | initial weight (g) | initial number | final weight (g) | final number | tumor weight (g) | tumor inhibition rate |
|---|---|---|---|---|---|---|---|
| endostar (rh-endostatin) | 2.5 | 20.11 ± 0.59 | 8 | 23.13 ± 0.38 | 7 | 0.71 ± 0.15 | 40.83% |
| polypeptide III (high) | 0.75 | 20.22 ± 0.40 | 8 | 23.10 ± 0.56 | 8 | 0.44 ± 0.11* | 63.73% |
| polypeptide III (medium) | 0.375 | 20.10 ± 0.56 | 8 | 22.85 ± 0.57 | 8 | 0.30 ± 0.09** | 74.62% |
| polypeptide III (low) | 0.1875 | 20.05 ± 0.52 | 8 | 22.94 ± 0.51 | 8 | 0.43 ± 0.09* | 64.55% |

RESULTS: the inhibition effect of polypeptide I on heterotransplanted human gallbladder cancer GBC-SD in nude mice is shown in Table 33. The inhibition rate of avastin on heterotransplanted human gallbladder cancer GBC-SD in nude mice was 78.85%; the body weight of mice from the avastin group presents no significant change in contrast with that from the negative control group. The inhibition rates of polypeptide I at high, medium and low doses on heterotransplanted human gallbladder cancer GBC-SD in nude mice were 58.33%, 65.00% and 56.67% respectively. The tumor volume of mice from both the high-dose group and low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human gallbladder cancer GBC-SD in nude mice is shown in Table 34. The inhibition rate of avastin on heterotransplanted human gallbladder cancer GBC-SD in nude mice was 78.85%; the body weight of mice from the avastin group presents no significant change in contrast with that from the negative control group. The inhibition rates of polypeptide II at high, medium and low doses on heterotransplanted human gallbladder cancer GBC-SD in nude mice were 60.48%, 69.19% and 62.00% respectively. The tumor volume of mice from both the high-dose group and low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human gallbladder cancer GBC-SD in nude mice is shown in Table 35. The inhibition rate of avastin on heterotransplanted human gallbladder cancer GBC-SD in nude mice was 78.85%; the body weight of mice from the avastin group presents no significant change in contrast with that from the negative control group. The inhibition rates of polypeptide III at high, medium and low doses on heterotransplanted human gallbladder cancer GBC-SD in nude mice were 63.73%, 74.62% and 64.55% respectively. The tumor volume of mice from both the high-dose group and low-dose group presents significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

Embodiment 15

Test on the Inhibition Effect of Integrin-Blocking Polypeptide I, Polypeptide II and Polypeptide III on Heterotransplanted Human Bladder Cancer HT1376 in Nude Mice The tumor inoculation process and analysis methods were the same as those mentioned in embodiment 6. Avastin used in the positive control group was administered once every 3 days through tail vein injection, while drugs of all other groups were administered on daily basis through tail vein injection.

TABLE 36 inhibition effect of polypeptide I on heterotransplanted
human bladder cancer HT1376 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.21 ± 0.60 | 12 | 23.03 ± 0.43 | 12 | 1.26 ± 0.32 | — |
| avastin | 10 | 19.83 ± 0.58 | 8 | 20.94 ± 0.47 | 7 | 0.24 ± 0.06** | 79.60% |
| endostar (rh-endostatin) | 2.5 | 20.15 ± 0.52 | 8 | 22.99 ± 0.62 | 7 | 0.73 ± 0.16 | 42.06% |
| polypeptide I (high) | 3 | 19.84 ± 0.55 | 8 | 23.14 ± 0.54 | 8 | 0.64 ± 0.13 | 49.20% |
| polypeptide I (medium) | 1.5 | 19.76 ± 0.43 | 8 | 22.88 ± 0.66 | 8 | 0.55 ± 0.09* | 56.34% |
| polypeptide I (low) | 0.75 | 20.19 ± 0.60 | 8 | 23.17 ± 0.58 | 8 | 0.59 ± 0.16 | 53.17% |

TABLE 37 inhibition effect of polypeptide II on heterotransplanted human bladder cancer HT1376 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.21 ± 0.60 | 12 | 23.03 ± 0.43 | 12 | 1.26 ± 0.32 | — |
| avastin | 10 | 19.83 ± 0.58 | 8 | 20.94 ± 0.47 | 7 | 0.24 ± 0.06** | 79.60% |
| endostar (rh-endostatin) | 2.5 | 20.15 ± 0.52 | 8 | 22.99 ± 0.62 | 7 | 0.73 ± 0.16 | 42.06% |
| polypeptide II (high) | 3 | 19.85 ± 0.55 | 8 | 23.21 ± 0.62 | 8 | 0.47 ± 0.12* | 60.97% |
| polypeptide II (medium) | 1.5 | 20.01 ± 0.66 | 8 | 22.88 ± 0.63 | 8 | 0.35 ± 0.09** | 71.10% |
| polypeptide II (low) | 0.75 | 20.00 ± 0.67 | 8 | 22.86 ± 0.63 | 8 | 0.39 ± 0.10** | 67.62% |

TABLE 38 inhibition effect of polypeptide III on heterotransplanted human bladder cancer HT1376 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.21 ± 0.60 | 12 | 23.03 ± 0.43 | 12 | 1.26 ± 0.32 | — |
| avastin | 10 | 19.83 ± 0.58 | 8 | 20.94 ± 0.47 | 7 | 0.24 ± 0.06** | 79.60% |
| endostar (rh-endostatin) | 2.5 | 20.15 ± 0.52 | 8 | 22.99 ± 0.62 | 7 | 0.73 ± 0.16 | 42.06% |
| polypeptide III (high) | 0.75 | 20.12 ± 0.70 | 8 | 22.90 ± 0.69 | 8 | 0.38 ± 0.10** | 67.92% |
| polypeptide III (medium) | 0.375 | 20.13 ± 0.67 | 8 | 22.85 ± 0.46 | 8 | 0.28 ± 0.08** | 76.94% |
| polypeptide III (low) | 0.1875 | 19.89 ± 0.62 | 8 | 23.20 ± 0.61 | 8 | 0.33 ± 0.09** | 72.55% |

RESULTS: the inhibition effect of polypeptide I on heterotransplanted human bladder cancer HT1376 in nude mice is shown in Table 36. The inhibition rate of avastin on heterotransplanted human bladder cancer HT1376 in nude mice was 79.60%; the body weight of mice from the avastin group presented no significant change in contrast with that from the negative control group. The inhibition rates of polypeptide I at high, medium and low doses on heterotransplanted human bladder cancer HT1376 in nude mice were 49.20%, 56.34% and 53.17% respectively. The tumor volume of mice from the medium-dose group exhibited significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human bladder cancer HT1376 in nude mice is shown in Table 37. The inhibition rate of avastin on heterotransplanted human bladder cancer HT1376 in nude mice was 79.60%; the body weight of mice from the avastin group presented no significant change in contrast with that from the negative control group. The inhibition rates of polypeptide II at high, medium and low doses on heterotransplanted human bladder cancer HT1376 in nude mice were 60.97%, 71.10% and 67.62% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human bladder cancer HT1376 in nude mice is shown in Table 38. The inhibition rate of avastin on heterotransplanted human bladder cancer HT1376 in nude mice was 79.60%; the body weight of mice from the avastin group presented no significant change in contrast with that from the negative control group. The inhibition rates of polypeptide III at high, medium and low doses on heterotransplanted human bladder cancer HT1376 in nude mice were 67.92%, 76.94% and 72.55% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 16

Test on the Inhibition Effect of Integrin-Blocking Polypeptide I, Polypeptide II and Polypeptide III on Heterotransplanted Human Pancreatic Cancer SW-1990 in Nude Mice The tumor inoculation process and analysis methods were the same as those mentioned in embodiment 6. Avastin used in the positive control group was administered once every 3 days through tail vein injection, while drugs of all other groups were administered on daily basis through tail vein injection.

TABLE 39 inhibition effect of polypeptide I on heterotransplanted human pancreatic cancer SW-1990 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.87 ± 0.41 | 12 | 23.08 ± 0.59 | 12 | 1.29 ± 0.32 | — |
| avastin | 10 | 19.94 ± 0.59 | 8 | 20.99 ± 0.66 | 7 | 0.27 ± 0.07** | 79.07% |
| endostar (rh-endostatin) | 2.5 | 19.88 ± 0.50 | 8 | 22.87 ± 0.57 | 7 | 0.65 ± 0.14 | 49.66% |
| polypeptide I (high) | 3 | 20.16 ± 0.45 | 8 | 22.86 ± 0.65 | 8 | 0.58 ± 0.10* | 55.04% |
| polypeptide I (medium) | 1.5 | 20.31 ± 0.50 | 8 | 23.03 ± 0.65 | 8 | 0.47 ± 0.08** | 63.57% |
| polypeptide I (low) | 0.75 | 20.09 ± 0.56 | 8 | 23.06 ± 0.64 | 8 | 0.51 ± 0.09** | 60.47% |

TABLE 40 inhibition effect of polypeptide II on heterotransplanted human pancreatic cancer SW-1990 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.87 ± 0.41 | 12 | 23.08 ± 0.59 | 12 | 1.29 ± 0.32 | — |
| avastin | 10 | 19.94 ± 0.59 | 8 | 20.99 ± 0.66 | 7 | 0.27 ± 0.07** | 79.07% |
| endostar (rh-endostatin) | 2.5 | 19.88 ± 0.50 | 8 | 22.87 ± 0.57 | 7 | 0.65 ± 0.14 | 49.66% |
| polypeptide II (high) | 3 | 20.21 ± 0.64 | 8 | 23.11 ± 0.61 | 8 | 0.45 ± 0.10** | 65.05% |
| polypeptide II (medium) | 1.5 | 19.76 ± 0.55 | 8 | 22.8 ± 0.57 | 8 | 0.35 ± 0.09** | 72.97% |
| polypeptide II (low) | 0.75 | 19.91 ± 0.58 | 8 | 22.80 ± 0.57 | 8 | 0.39 ± 0.10** | 70.09% |

TABLE 41 inhibition effect of polypeptide III on heterotransplanted human pancreatic cancer SW-1990 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.87 ± 0.41 | 12 | 23.08 ± 0.59 | 12 | 1.29 ± 0.32 | — |
| avastin | 10 | 19.94 ± 0.59 | 8 | 20.99 ± 0.66 | 7 | 0.27 ± 0.07** | 79.07% |
| endostar (rh-endostatin) | 2.5 | 19.88 ± 0.50 | 8 | 22.87 ± 0.57 | 7 | 0.65 ± 0.14 | 49.66% |
| polypeptide III (high) | 0.75 | 20.28 ± 0.53 | 8 | 23.00 ± 0.39 | 8 | 0.37 ± 0.08** | 71.01% |
| polypeptide III (medium) | 0.375 | 20.05 ± 0.60 | 8 | 22.93 ± 0.56 | 8 | 0.28 ± 0.06** | 78.64% |
| polypeptide III (low) | 0.1875 | 20.27 ± 0.67 | 8 | 23.21 ± 0.61 | 8 | 0.33 ± 0.08** | 74.68% |

RESULTS: the inhibition effect of polypeptide I on heterotransplanted human pancreatic cancer SW-1990 in nude mice is shown in Table 39. The inhibition rate of avastin on heterotransplanted human pancreatic cancer SW-1990 in nude mice was 79.07%; the body weight of mice from the avastin group presented no significant change in contrast with that from the negative control group. The inhibition rates of polypeptide I at high, medium and low doses on heterotransplanted human pancreatic cancer SW-1990 in nude mice were 55.04%, 63.57% and 60.47% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human pancreatic cancer SW-1990 in nude mice is shown in Table 40. The inhibition rate of avastin on heterotransplanted human pancreatic cancer SW-1990 in nude mice was 79.07%; the body weight of mice from the avastin group presented no significant change in contrast with that from the negative control group. The inhibition rates of polypeptide II at high, medium and low doses on heterotransplanted human pancreatic cancer SW-1990 in nude mice were 65.05%, 72.97% and 70.09% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human pancreatic cancer SW-1990 in nude mice is shown in Table 41. The inhibition rate of avastin on heterotransplanted human pancreatic cancer SW-1990 in nude mice was 79.07%; the body weight of mice from the avastin group presented no significant change in contrast with that from the negative control group. The inhibition rates of polypeptide III at high, medium and low doses on heterotransplanted human pancreatic cancer SW-1990 in nude mice were 71.01%, 78.64% and 74.68% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 17

Test on the Inhibition Effect of Integrin-Blocking Polypeptide I, Polypeptide II and Polypeptide III on Heterotransplanted Human Esophageal Cancer Ec109 in Nude Mice The tumor inoculation process and analysis methods were the same as those mentioned in embodiment 6. Avastin used in the positive control group was administered once every 3 days through tail vein injection, while drugs of all other groups were administered on daily basis through tail vein injection.

TABLE 42 inhibition effect of polypeptide I on heterotransplanted human esophageal cancer Ec109 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.19 ± 0.57 | 12 | 22.82 ± 0.63 | 12 | 1.53 ± 0.38 | — |
| avastin | 10 | 20.04 ± 0.55 | 8 | 20.93 ± 0.51 | 7 | 0.47 ± 0.10** | 69.00% |
| endostar (rh-endostatin) | 2.5 | 19.86 ± 0.49 | 8 | 22.92 ± 0.45 | 7 | 0.89 ± 0.24 | 41.57% |
| polypeptide I (high) | 3 | 20.00 ± 0.67 | 8 | 22.94 ± 0.64 | 7 | 0.54 ± 0.08** | 64.71% |
| polypeptide I (medium) | 1.5 | 20.09 ± 0.56 | 8 | 23.06 ± 0.64 | 8 | 0.47 ± 0.06** | 69.00% |
| polypeptide I (low) | 0.75 | 20.00 ± 0.58 | 8 | 22.63 ± 0.57 | 8 | 0.53 ± 0.08** | 65.36% |

TABLE 43 inhibition effect of polypeptide II on heterotransplanted human esophageal cancer Ec109 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.19 ± 0.57 | 12 | 22.82 ± 0.63 | 12 | 1.53 ± 0.38 | — |
| avastin | 10 | 20.04 ± 0.55 | 8 | 20.93 ± 0.51 | 7 | 0.47 ± 0.10** | 69.00% |
| endostar (rh-endostatin) | 2.5 | 19.86 ± 0.49 | 8 | 22.92 ± 0.45 | 7 | 0.89 ± 0.24 | 41.57% |
| polypeptide II (high) | 3 | 19.93 ± 0.64 | 8 | 22.90 ± 0.59 | 8 | 0.71 ± 0.15* | 53.34% |
| polypeptide II (medium) | 1.5 | 20.06 ± 0.56 | 8 | 23.08 ± 0.58 | 8 | 0.55 ± 0.12** | 63.88% |
| polypeptide II (low) | 0.75 | 20.05 ± 0.66 | 8 | 22.97 ± 0.58 | 8 | 0.62 ± 0.13* | 59.65% |

TABLE 44 inhibition effect of polypeptide III on heterotransplanted human esophageal cancer Ec109 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.19 ± 0.57 | 12 | 22.82 ± 0.63 | 12 | 1.53 ± 0.38 | — |
| avastin | 10 | 20.04 ± 0.55 | 8 | 20.93 ± 0.51 | 7 | 0.47 ± 0.10** | 69.00% |

TABLE 44-continued inhibition effect of polypeptide III on heterotransplanted
human esophageal cancer Ec109 in nude mice

| group | dose (mg/kg/ time) | initial weight (g) | initial number | final weight (g) | final number | tumor weight (g) | tumor inhibition rate |
|---|---|---|---|---|---|---|---|
| endostar (rh-endostatin) | 2.5 | 19.86 ± 0.49 | 8 | 22.92 ± 0.45 | 7 | 0.89 ± 0.24 | 41.57% |
| polypeptide III (high) | 0.75 | 19.98 ± 0.57 | 8 | 23.17 ± 0.67 | 8 | 0.62 ± 0.18* | 59.75% |
| polypeptide III (medium) | 0.375 | 20.18 ± 0.53 | 8 | 23.31 ± 0.73 | 8 | 0.50 ± 0.12** | 67.13% |
| polypeptide III (low) | 0.1875 | 20.06 ± 0.44 | 8 | 23.14 ± 0.52 | 8 | 0.53 ± 0.14** | 65.63% |

RESULTS: the inhibition effect of polypeptide I on heterotransplanted human esophageal cancer Ec109 in nude mice is shown in Table 42. The inhibition rate of avastin on heterotransplanted human esophageal cancer Ec109 in nude mice was 69.00%; the body weight of mice from the avastin group presented no significant change in contrast with that from the negative control group. The inhibition rates of polypeptide I at high, medium and low doses on heterotransplanted human esophageal cancer Ec109 in nude mice were 64.71%, 69.00% and 65.36% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human esophageal cancer Ec109 in nude mice is shown in Table 43. The inhibition rate of avastin on heterotransplanted human esophageal cancer Ec109 in nude mice was 69.00%; the body weight of mice from the avastin group presented no significant change in contrast with that from the negative control group. The inhibition rates of polypeptide II at high, medium and low doses on heterotransplanted human esophageal cancer Ec109 in nude mice were 53.34%, 63.88% and 59.65% respectively. The tumor volume of mice from both the high-dose group and the low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human esophageal cancer Ec109 in nude mice is shown in Table 44. The inhibition rate of avastin on heterotransplanted human esophageal cancer Ec109 in nude mice was 69.00%; the body weight of mice from the avastin group presented no significant change in contrast with that from the negative control group. The inhibition rates of polypeptide III at high, medium and low doses on heterotransplanted human esophageal cancer Ec109 in nude mice were 59.75%, 67.13% and 65.63% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

Embodiment 18

Test on the Inhibition Effect of Integrin-Blocking Polypeptide I, Polypeptide II and Polypeptide III on Heterotransplanted Human Colon Cancer HT-29 in Nude Mice The tumor inoculation process and analysis methods were the same as those mentioned in embodiment 6. Cisplatin used in the positive control group was administered once every 3 days through tail vein injection, while drugs of all other groups were administered on daily basis through tail vein injection.

TABLE 45 inhibition effect of polypeptide I on heterotransplanted
human colon cancer HT-29 in nude mice

| group | dose (mg/kg/ time) | initial weight (g) | initial number | final weight (g) | final number | tumor weight (g) | tumor inhibition rate |
|---|---|---|---|---|---|---|---|
| control | — | 20.09 ± 0.64 | 12 | 22.78 ± 0.62 | 12 | 1.44 ± 0.36 | — |
| cisplatin | 10 | 20.17 ± 0.56 | 8 | 17.75 ± 0.53 | 7 | 0.30 ± 0.05** | 79.17% |
| endostar (rh-endostatin) | 2.5 | 19.96 ± 0.60 | 8 | 22.91 ± 0.61 | 8 | 0.58 ± 0.14 | 59.50% |
| polypeptide I (high) | 3 | 19.95 ± 1.21 | 10 | 19.60 ± 1.26 | 10 | 0.56 ± 0.15** | 61.11% |
| polypeptide I (medium) | 1.5 | 20.15 ± 0.97 | 10 | 19.67 ± 1.41 | 10 | 0.49 ± 0.12** | 65.97% |
| polypeptide I (low) | 0.75 | 20.00 ± 1.22 | 10 | 20.40 ± 1.26 | 10 | 0.46 ± 0.13** | 68.05% |

TABLE 46 inhibition effect of polypeptide II on heterotransplanted human colon cancer HT-29 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.64 | 12 | 22.78 ± 0.62 | 12 | 1.44 ± 0.36 | — |
| cisplatin | 10 | 20.17 ± 0.56 | 8 | 17.75 ± 0.53 | 7 | 0.30 ± 0.05** | 79.17% |
| endostar (rh-endostatin) | 2.5 | 19.96 ± 0.60 | 8 | 22.91 ± 0.61 | 8 | 0.58 ± 0.14 | 59.50% |
| polypeptide II (high) | 3 | 19.90 ± 0.65 | 8 | 22.77 ± 0.60 | 8 | 0.39 ± 0.09** | 72.93% |
| polypeptide II (medium) | 1.5 | 19.80 ± 0.54 | 8 | 23.13 ± 0.71 | 8 | 0.26 ± 0.07** | 81.96% |
| polypeptide II (low) | 0.75 | 19.89 ± 0.61 | 8 | 22.81 ± 0.71 | 8 | 0.31 ± 0.07** | 78.32% |

TABLE 47 inhibition effect of polypeptide III on heterotransplanted human colon cancer HT-29 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.64 | 12 | 22.78 ± 0.62 | 12 | 1.44 ± 0.36 | — |
| cisplatin | 10 | 20.17 ± 0.56 | 8 | 17.75 ± 0.53 | 7 | 0.30 ± 0.05** | 79.17% |
| endostar (rh-endostatin) | 2.5 | 19.96 ± 0.60 | 8 | 22.91 ± 0.61 | 8 | 0.58 ± 0.14 | 59.50% |
| polypeptide III (high) | 0.75 | 20.12 ± 0.67 | 8 | 22.90 ± 0.52 | 8 | 0.30 ± 0.09** | 79.11% |
| polypeptide III (medium) | 0.375 | 20.12 ± 0.58 | 8 | 23.04 ± 0.63 | 8 | 0.21 ± 0.06** | 85.62% |
| polypeptide III (low) | 0.1875 | 20.28 ± 0.70 | 8 | 22.84 ± 0.52 | 8 | 0.23 ± 0.07** | 83.70% |

RESULTS: the inhibition effect of polypeptide I on heterotransplanted human colon cancer HT-29 in nude mice is shown in Table 45. The inhibition rate of the cisplatin group on heterotransplanted human colon cancer HT-29 in nude mice was 79.17%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human colon cancer HT-29 in nude mice were 61.11%, 65.97% and 68.05% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human colon cancer HT-29 in nude mice is shown in Table 46. The inhibition rate of the cisplatin group on heterotransplanted human colon cancer HT-29 in nude mice was 79.17%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human colon cancer HT-29 in nude mice were 72.93%, 81.96% and 78.32% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human colon cancer HT-29 in nude mice is shown in Table 47. The inhibition rate of the cisplatin group on heterotransplanted human colon cancer HT-29 in nude mice was 79.17%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human colon cancer HT-29 in nude mice were 79.11%, 85.62% and 83.70% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 19

Test on the Inhibition Effect of Integrin-Blocking Polypeptide I, Polypeptide II and Polypeptide III on Heterotransplanted Human Thyroid Cancer SW-579 in Nude Mice The tumor inoculation process and analysis methods were the same as those mentioned in embodiment 6. Cisplatin used in the positive control group was administered once every 3 days through tail vein injection, while drugs of all other groups were administered on daily basis through tail vein injection.

is shown in Table 48. The inhibition rate of the cisplatin group on heterotransplanted human thyroid cancer SW-579 in nude mice was 74.09%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human thyroid cancer SW-579 in nude mice were 58.01%, 64.89% and 64.12% respectively. The tumor volume of mice from the high-dose group presented significant

TABLE 48 inhibition effect of polypeptide I on heterotransplanted human thyroid cancer SW-579 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.95 ± 0.54 | 12 | 22.83 ± 0.56 | 12 | 1.31 ± 0.30 | — |
| cisplatin | 10 | 20.15 ± 0.66 | 8 | 18.25 ± 0.65 | 7 | 0.34 ± 0.07** | 74.09% |
| endostar (rh-endostatin) | 2.5 | 20.07 ± 0.61 | 8 | 22.70 ± 0.54 | 8 | 0.88 ± 0.19 | 32.82% |
| polypeptide I (high) | 3 | 19.75 ± 0.65 | 10 | 20.88 ± 0.85 | 10 | 0.55 ± 0.12* | 58.01% |
| polypeptide I (medium) | 1.5 | 19.63 ± 0.75 | 10 | 20.13 ± 1.03 | 10 | 0.46 ± 0.16** | 64.89% |
| polypeptide I (low) | 0.75 | 20.25 ± 0.65 | 10 | 22.25 ± 1.71 | 10 | 0.47 ± 0.14** | 64.12% |

TABLE 49 inhibition effect of polypeptide II on heterotransplanted human thyroid cancer SW-579 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.95 ± 0.54 | 12 | 22.83 ± 0.56 | 12 | 1.31 ± 0.30 | — |
| cisplatin | 10 | 20.15 ± 0.66 | 8 | 18.25 ± 0.65 | 7 | 0.34 ± 0.07** | 74.09% |
| endostar (rh-endostatin) | 2.5 | 20.07 ± 0.61 | 8 | 22.70 ± 0.54 | 8 | 0.88 ± 0.19 | 32.82% |
| polypeptide II (high) | 3 | 19.82 ± 0.39 | 8 | 23.15 ± 0.67 | 8 | 0.57 ± 0.15* | 56.59% |
| polypeptide II (medium) | 1.5 | 19.88 ± 0.50 | 8 | 23.23 ± 0.67 | 8 | 0.43 ± 0.10** | 66.94% |
| polypeptide II (low) | 0.75 | 19.64 ± 0.44 | 8 | 22.92 ± 0.67 | 8 | 0.51 ± 0.13** | 60.97% |

TABLE 50 inhibition effect of polypeptide III on heterotransplanted human thyroid cancer SW-579 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.95 ± 0.54 | 12 | 22.83 ± 0.56 | 12 | 1.31 ± 0.30 | — |
| cisplatin | 10 | 20.15 ± 0.66 | 8 | 18.25 ± 0.65 | 7 | 0.34 ± 0.07** | 74.09% |
| endostar (rh-endostatin) | 2.5 | 20.07 ± 0.61 | 8 | 22.70 ± 0.54 | 8 | 0.88 ± 0.19 | 32.82% |
| polypeptide III (high) | 0.75 | 19.76 ± 0.53 | 8 | 22.56 ± 0.55 | 8 | 0.48 ± 0.14** | 63.38% |
| polypeptide III (medium) | 0.375 | 19.96 ± 0.54 | 8 | 23.09 ± 0.54 | 8 | 0.39 ± 0.08** | 70.58% |
| polypeptide III (low) | 0.1875 | 19.98 ± 0.55 | 8 | 23.18 ± 0.66 | 8 | 0.44 ± 0.09** | 66.40% |

RESULTS: the inhibition effect of polypeptide I on heterotransplanted human thyroid cancer SW-579 in nude mice difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human thyroid cancer SW-579 in nude mice is shown in Table 49. The inhibition rate of the cisplatin group on heterotransplanted human thyroid cancer SW-579 in nude mice was 74.09%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human thyroid cancer SW-579 in nude mice were 56.59%, 66.94% and 60.97% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human thyroid cancer SW-579 in nude mice is shown in Table 50. The inhibition rate of the cisplatin group on heterotransplanted human thyroid cancer SW-579 in nude mice was 74.09%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human thyroid cancer SW-579 in nude mice were 63.38%, 70.58% and 66.40% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 20

Test on the Inhibition Effect of Integrin-Blocking Polypeptide I, Polypeptide II and Polypeptide III on Heterotransplanted Human Renal Cancer A498 in Nude Mice The tumor inoculation process and analysis methods were the same as those mentioned in embodiment 6. Cisplatin used in the positive control group was administered once every 3 days through tail vein injection, while drugs of all other groups were administered on daily basis through tail vein injection.

TABLE 51 inhibition effect of polypeptide I on heterotransplanted human renal cancer A498 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.99 ± 0.72 | 12 | 23.13 ± 0.51 | 12 | 1.23 ± 0.26 | — |
| cisplatin | 10 | 20.13 ± 0.57 | 8 | 17.80 ± 0.63 | 7 | 0.25 ± 0.06** | 79.83% |
| endostar (rh-endostatin) | 2.5 | 19.94 ± 0.65 | 8 | 22.96 ± 0.69 | 8 | 0.70 ± 0.14 | 43.20% |
| polypeptide I (high) | 3 | 20.21 ± 0.57 | 8 | 22.59 ± 0.53 | 8 | 0.57 ± 0.15* | 53.65% |
| polypeptide I (medium) | 1.5 | 20.06 ± 0.47 | 8 | 23.26 ± 0.40 | 8 | 0.49 ± 0.10** | 60.16% |
| polypeptide I (low) | 0.75 | 20.02 ± 0.51 | 8 | 22.87 ± 0.40 | 8 | 0.51 ± 0.13* | 58.53% |

TABLE 52 inhibition effect of polypeptide II on heterotransplanted human renal cancer A498 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.99 ± 0.72 | 12 | 23.13 ± 0.51 | 12 | 1.23 ± 0.26 | — |
| cisplatin | 10 | 20.13 ± 0.57 | 8 | 17.80 ± 0.63 | 7 | 0.25 ± 0.06** | 79.83% |
| endostar (rh-endostatin) | 2.5 | 19.94 ± 0.65 | 8 | 22.96 ± 0.69 | 8 | 0.70 ± 0.14 | 43.20% |
| polypeptide II (high) | 3 | 20.05 ± 0.52 | 8 | 22.93 ± 0.51 | 8 | 0.43 ± 0.11** | 64.90% |
| polypeptide II (medium) | 1.5 | 19.91 ± 0.57 | 8 | 23.13 ± 0.58 | 8 | 0.35 ± 0.09** | 71.41% |
| polypeptide II (low) | 0.75 | 19.94 ± 0.56 | 8 | 23.14 ± 0.58 | 8 | 0.41 ± 0.11** | 67.03% |

TABLE 53 inhibition effect of polypeptide III on heterotransplanted human renal cancer A498 in nude mice

| group | dose (mg/kg/ time) | initial weight (g) | initial number | final weight (g) | final number | tumor weight (g) | tumor inhibition rate |
|---|---|---|---|---|---|---|---|
| control | — | 19.99 ± 0.72 | 12 | 23.13 ± 0.51 | 12 | 1.23 ± 0.26 | — |
| cisplatin | 10 | 20.13 ± 0.57 | 8 | 17.80 ± 0.63 | 7 | 0.25 ± 0.06** | 79.83% |
| endostar (rh-endostatin) | 2.5 | 19.94 ± 0.65 | 8 | 22.96 ± 0.69 | 8 | 0.70 ± 0.14 | 43.20% |
| polypeptide III (high) | 0.75 | 19.68 ± 0.59 | 8 | 23.18 ± 0.50 | 8 | 0.41 ± 0.12** | 66.36% |
| polypeptide III (medium) | 0.375 | 19.83 ± 0.65 | 8 | 22.92 ± 0.59 | 8 | 0.30 ± 0.07** | 75.36% |
| polypeptide III (low) | 0.1875 | 19.97 ± 0.66 | 8 | 22.82 ± 0.69 | 8 | 0.36 ± 0.10** | 70.74% |

RESULTS: the inhibition effect of polypeptide I on heterotransplanted human renal cancer A498 in nude mice is shown in Table 51. The inhibition rate of the cisplatin group on heterotransplanted human renal cancer A498 in nude mice was 79.83%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human renal cancer A498 in nude mice were 53.65%, 60.16% and 58.53% respectively. The tumor volume of mice from both the high-dose group and low-dose group presented significant difference in contrast with that from the negative control group; the tumor volume of mice from the medium-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human renal cancer A498 in nude mice is shown in Table 52. The inhibition rate of the cisplatin group on heterotransplanted human renal cancer A498 in nude mice was 79.83%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human renal cancer A498 in nude mice were 64.90%, 71.41% and 67.03% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human renal cancer A498 in nude mice is shown in Table 53. The inhibition rate of the cisplatin group on heterotransplanted human renal cancer A498 in nude mice was 79.83%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human renal cancer A498 in nude mice were 66.36%, 75.36% and 70.74% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 21

Test on the Inhibition Effect of Integrin-Blocking Polypeptide I, Polypeptide II and Polypeptide III on Heterotransplanted Human Ovarian Cancer SK-OV-3 in Nude Mice The tumor inoculation process and analysis methods were the same as those mentioned in embodiment 6. Cisplatin used in the positive control group was administered once every 3 days through tail vein injection, while drugs of all other groups were administered on daily basis through tail vein injection.

TABLE 54 inhibition effect of polypeptide I on heterotransplanted human ovarian cancer SK-OV-3 in nude mice

| group | dose (mg/kg/ time) | initial weight (g) | initial number | final weight (g) | final number | tumor weight (g) | tumor inhibition rate |
|---|---|---|---|---|---|---|---|
| control | — | 19.87 ± 0.43 | 12 | 23.03 ± 0.59 | 12 | 1.34 ± 0.27 | — |
| cisplatin | 10 | 20.04 ± 0.58 | 8 | 18.15 ± 0.57 | 7 | 0.29 ± 0.06** | 78.36% |
| endostar (rh-endostatin) | 2.5 | 19.99 ± 0.71 | 8 | 23.19 ± 0.72 | 8 | 0.88 ± 0.17 | 34.32% |

TABLE 54-continued inhibition effect of polypeptide I on heterotransplanted human ovarian cancer SK-OV-3 in nude mice

| group | dose (mg/kg/ time) | initial weight (g) | initial number | final weight (g) | final number | tumor weight (g) | tumor inhibition rate |
|---|---|---|---|---|---|---|---|
| polypeptide I (high) | 3 | 20.03 ± 0.61 | 8 | 23.16 ± 0.51 | 8 | 0.47 ± 0.12** | 67.13% |
| polypeptide I (medium) | 1.5 | 20.05 ± 0.58 | 8 | 22.96 ± 0.59 | 8 | 0.39 ± 0.07** | 70.89% |
| polypeptide I (low) | 0.75 | 19.97 ± 0.62 | 8 | 23.09 ± 0.59 | 8 | 0.41 ± 0.10** | 69.40% |

TABLE 55 inhibition effect of polypeptide II on heterotransplanted human ovarian cancer SK-OV-3 in nude mice

| group | dose (mg/kg/ time) | initial weight (g) | initial number | final weight (g) | final number | tumor weight (g) | tumor inhibition rate |
|---|---|---|---|---|---|---|---|
| control | — | 19.87 ± 0.43 | 12 | 23.03 ± 0.59 | 12 | 1.34 ± 0.27 | — |
| cisplatin | 10 | 20.04 ± 0.58 | 8 | 18.15 ± 0.57 | 7 | 0.29 ± 0.06** | 78.36% |
| endostar (rh-endostatin) | 2.5 | 19.99 ± 0.71 | 8 | 23.19 ± 0.72 | 8 | 0.88 ± 0.17 | 34.32% |
| polypeptide II (high) | 3 | 20.22 ± 0.52 | 8 | 22.97 ± 0.65 | 8 | 0.49 ± 0.14** | 63.25% |
| polypeptide II (medium) | 1.5 | 19.83 ± 0.58 | 8 | 23.32 ± 0.50 | 8 | 0.36 ± 0.08** | 72.76% |
| polypeptide II (low) | 0.75 | 19.91 ± 0.61 | 8 | 23.07 ± 0.50 | 8 | 0.42 ± 0.10** | 68.36% |

TABLE 56 inhibition effect of polypeptide III on heterotransplanted human ovarian cancer SK-OV-3 in nude mice

| group | dose (mg/kg/ time) | initial weight (g) | initial number | final weight (g) | final number | tumor weight (g) | tumor inhibition rate |
|---|---|---|---|---|---|---|---|
| control | — | 19.87 ± 0.43 | 12 | 23.03 ± 0.59 | 12 | 1.34 ± 0.27 | — |
| cisplatin | 10 | 20.04 ± 0.58 | 8 | 18.15 ± 0.57 | 7 | 0.29 ± 0.06** | 78.36% |
| endostar (rh-endostatin) | 2.5 | 19.99 ± 0.71 | 8 | 23.19 ± 0.72 | 8 | 0.88 ± 0.17 | 34.32% |
| polypeptide III (high) | 0.75 | 20.18 ± 0.58 | 8 | 22.95 ± 0.64 | 8 | 0.40 ± 0.11** | 69.98% |
| polypeptide III (medium) | 0.375 | 19.91 ± 0.55 | 8 | 22.92 ± 0.70 | 8 | 0.31 ± 0.07** | 76.63% |
| polypeptide III (low) | 0.1875 | 19.55 ± 0.57 | 8 | 22.83 ± 0.50 | 8 | 0.35 ± 0.09** | 73.87% |

RESULTS: the inhibition effect of polypeptide I on heterotransplanted human ovarian cancer SK-OV-3 in nude mice is shown in Table 54. The inhibition rate of the cisplatin group on heterotransplanted human ovarian cancer SK-OV-3 in nude mice was 78.36%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human ovarian cancer SK-OV-3 in nude mice were 67.13%, 70.89% and 69.40% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human ovarian cancer SK-OV-3 in nude mice is shown in Table 55. The inhibition rate of the cisplatin group on heterotransplanted human ovarian cancer SK-OV-3 in nude mice was 78.36%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human ovarian cancer SK-OV-3 in nude mice were 63.25%, 72.76% and 68.36% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human ovarian cancer SK-OV-3 in nude mice is shown in Table 56. The inhibition rate of the cisplatin group on heterotransplanted human ovarian cancer SK-OV-3 in nude mice was 78.36%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human ovarian cancer SK-OV-3 in nude mice were 69.98%, 76.63% and 73.87% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 22

Test on the Inhibition Effect of Integrin-Blocking Polypeptide I, Polypeptide II and Polypeptide III on Heterotransplanted Sarcoma HT-1080 in Nude Mice The tumor inoculation process and analysis methods were the same as those mentioned in embodiment 6. 5-fluorouracil (5-FU) used in the positive control group was administered once every 3 days through tail vein injection, while drugs of all other groups were administered on daily basis through tail vein injection.

TABLE 57 inhibition effect of polypeptide I on heterotransplanted sarcoma HT-1080 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.66 | 12 | 23.01 ± 0.48 | 12 | 1.37 ± 0.35 | — |
| 5-Fu | 10 | 19.94 ± 0.58 | 8 | 17.88 ± 0.68 | 7 | 0.30 ± 0.07** | 78.10% |
| endostar (rh-endostatin) | 2.5 | 19.88 ± 0.79 | 8 | 22.89 ± 0.51 | 8 | 0.69 ± 0.15 | 49.72% |
| polypeptide I (high) | 3 | 20.11 ± 0.59 | 8 | 23.13 ± 0.38 | 7 | 0.49 ± 0.14** | 64.23% |
| polypeptide I (medium) | 1.5 | 20.06 ± 0.63 | 8 | 23.10 ± 0.64 | 8 | 0.36 ± 0.08** | 73.72% |
| polypeptide I (low) | 0.75 | 19.80 ± 0.39 | 8 | 22.99 ± 0.51 | 8 | 0.42 ± 0.10** | 69.34% |

TABLE 58 inhibition effect of polypeptide I Ion heterotransplanted sarcoma HT-1080 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.66 | 12 | 23.01 ± 0.48 | 12 | 1.37 ± 0.35 | — |
| 5-Fu | 10 | 19.94 ± 0.58 | 8 | 17.88 ± 0.68 | 7 | 0.30 ± 0.07** | 78.10% |
| endostar (rh-endostatin) | 2.5 | 19.88 ± 0.79 | 8 | 22.89 ± 0.51 | 8 | 0.69 ± 0.15 | 49.72% |
| polypeptide II (high) | 3 | 20.08 ± 0.59 | 8 | 23.04 ± 0.55 | 8 | 0.45 ± 0.11** | 67.06% |
| polypeptide II (medium) | 1.5 | 19.70 ± 0.52 | 8 | 22.95 ± 0.46 | 8 | 0.35 ± 0.07** | 74.43% |
| polypeptide II (low) | 0.75 | 20.28 ± 0.61 | 8 | 22.93 ± 0.46 | 8 | 0.40 ± 0.11** | 70.60% |

TABLE 59 inhibition effect of polypeptide II Ion heterotransplanted sarcoma HT-1080 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.66 | 12 | 23.01 ± 0.48 | 12 | 1.37 ± 0.35 | — |
| 5-Fu | 10 | 19.94 ± 0.58 | 8 | 17.88 ± 0.68 | 7 | 0.30 ± 0.07** | 78.10% |
| endostar (rh-endostatin) | 2.5 | 19.88 ± 0.79 | 8 | 22.89 ± 0.51 | 8 | 0.69 ± 0.15 | 49.72% |

TABLE 59-continued inhibition effect of polypeptide II Ion heterotransplanted sarcoma HT-1080 in nude mice

| group | dose (mg/kg/time) | initial weight (g) | initial number | final weight (g) | final number | tumor weight (g) | tumor inhibition rate |
|---|---|---|---|---|---|---|---|
| polypeptide III (high) | 0.75 | 19.89 ± 0.53 | 8 | 23.07 ± 0.56 | 8 | 0.37 ± 0.10** | 73.29% |
| polypeptide III (medium) | 0.375 | 20.31 ± 0.51 | 8 | 23.18 ± 0.57 | 8 | 0.28 ± 0.06** | 79.90% |
| polypeptide III (low) | 0.1875 | 19.74 ± 0.55 | 8 | 22.92 ± 0.57 | 8 | 0.33 ± 0.07** | 75.87% |

RESULTS: the inhibition effect of polypeptide I on heterotransplanted sarcoma HT-1080 in nude mice is shown in Table 57. The inhibition rate of the 5-FU group on heterotransplanted sarcoma HT-1080 in nude mice was 78.10%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted sarcoma HT-1080 in nude mice were 64.23%, 73.72% and 69.34% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted sarcoma HT-1080 in nude mice is shown in Table 58. The inhibition rate of the 5-FU group on heterotransplanted sarcoma HT-1080 in nude mice was 78.10%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted sarcoma HT-1080 in nude mice were 67.06%, 74.43% and 70.60% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted sarcoma HT-1080 in nude mice is shown in Table 59. The inhibition rate of the 5-FU group on heterotransplanted sarcoma HT-1080 in nude mice was 78.10%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted sarcoma HT-1080 in nude mice were 73.29%, 79.90% and 75.87% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

Embodiment 23

Test on the Inhibition Effect of Integrin-Blocking Polypeptide I, Polypeptide II and Polypeptide III on Heterotransplanted Human Laryngeal Cancer Hep-2 in Nude Mice The tumor inoculation process and analysis methods were the same as those mentioned in embodiment 6. Avastin used in the positive control group was administered once every 3 days through tail vein injection, while drugs of all other groups were administered on daily basis through tail vein injection.

TABLE 60 inhibition effect of polypeptide I on heterotransplanted human laryngeal cancer Hep-2 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.00 ± 0.52 | 12 | 23.33 ± 0.44 | 12 | 1.12 ± 0.20 | — |
| avastin | 10 | 20.09 ± 0.70 | 8 | 20.47 ± 0.70 | 6 | 0.26 ± 0.06** | 76.79% |
| endostar (rh-endostatin) | 2.5 | 20.18 ± 0.61 | 8 | 23.23 ± 0.67 | 7 | 0.59 ± 0.10 | 46.96% |
| polypeptide I (high) | 3 | 20.15 ± 0.52 | 8 | 22.99 ± 0.62 | 8 | 0.50 ± 0.10* | 55.35% |
| polypeptide I (medium) | 1.5 | 19.85 ± 0.55 | 8 | 23.21 ± 0.62 | 8 | 0.41 ± 0.16** | 63.39% |
| polypeptide I (low) | 0.75 | 20.01 ± 0.66 | 8 | 22.88 ± 0.63 | 8 | 0.43 ± 0.07** | 60.90% |

TABLE 61 inhibition effect of polypeptide II on heterotransplanted
human laryngeal cancer Hep-2 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.00 ± 0.52 | 12 | 23.33 ± 0.44 | 12 | 1.12 ± 0.20 | — |
| avastin | 10 | 20.09 ± 0.70 | 8 | 20.47 ± 0.70 | 6 | 0.26 ± 0.06** | 76.79% |
| endostar (rh-endostatin) | 2.5 | 20.18 ± 0.61 | 8 | 23.23 ± 0.67 | 7 | 0.59 ± 0.10 | 46.96% |
| polypeptide II (high) | 3 | 20.02 ± 0.52 | 8 | 22.66 ± 0.61 | 8 | 0.44 ± 0.08* | 60.76% |
| polypeptide II (medium) | 1.5 | 20.14 ± 0.52 | 8 | 22.98 ± 0.60 | 8 | 0.33 ± 0.07** | 70.41% |
| polypeptide II (low) | 0.75 | 19.96 ± 0.52 | 8 | 22.88 ± 0.70 | 8 | 0.39 ± 0.06** | 64.98% |

TABLE 62 inhibition effect of polypeptide III on heterotransplanted
human laryngeal cancer Hep-2 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.00 ± 0.52 | 12 | 23.33 ± 0.44 | 12 | 1.12 ± 0.20 | — |
| avastin | 10 | 20.09 ± 0.70 | 8 | 20.47 ± 0.70 | 6 | 0.26 ± 0.06 | 76.79% |
| endostar (rh-endostatin) | 2.5 | 20.18 ± 0.61 | 8 | 23.23 ± 0.67 | 7 | 0.59 ± 0.10 | 46.96% |
| polypeptide III (high) | 0.75 | 20.07 ± 0.53 | 8 | 23.18 ± 0.51 | 8 | 0.42 ± 0.10* | 62.81% |
| polypeptide III (medium) | 0.375 | 20.17 ± 0.48 | 8 | 22.96 ± 0.57 | 8 | 0.28 ± 0.05** | 75.13% |
| polypeptide III (low) | 0.1875 | 19.62 ± 0.52 | 8 | 22.94 ± 0.46 | 8 | 0.37 ± 0.08** | 67.29% |

RESULTS: the inhibition effect of polypeptideIon heterotransplanted human laryngeal cancer Hep-2 in nude mice is shown in Table 60. The inhibition rate of avastin on heterotransplanted human laryngeal cancer Hep-2 in nude mice was 76.79%, and the body weight of mice from the avastin group showed no significant change. The inhibition rates of polypeptide I at high, medium and low doses on heterotransplanted human laryngeal cancer Hep-2 in nude mice were 55.35%, 63.39% and 60.90% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human laryngeal cancer Hep-2 in nude mice is shown in Table 61. The inhibition rate of avastin on heterotransplanted human laryngeal cancer Hep-2 in nude mice was 76.79%, and the body weight of mice from the avastin group showed no significant change. The inhibition rates of polypeptide II at high, medium and low doses on heterotransplanted human laryngeal cancer Hep-2 in nude mice were 60.76%, 70.41% and 64.98% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human laryngeal cancer Hep-2 in nude mice is shown in Table 62. The inhibition rate of avastin on heterotransplanted human laryngeal cancer Hep-2 in nude mice was 76.79%, and the body weight of mice from the avastin group showed no significant change. The inhibition rates of polypeptide III at high, medium and low doses on heterotransplanted human laryngeal cancer Hep-2 in nude mice were 62.81%, 75.13% and 67.29% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

Embodiment 24

Test on the Inhibition Effect of Integrin-Blocking Polypeptide I, Polypeptide II and Polypeptide III on Heterotransplanted Human Brain Tumor SF763 in Nude Mice The tumor inoculation process and analysis methods were the same as those mentioned in embodiment 6. Taxol used in the positive control group was administered once every 3 days through tail vein injection, while drugs of all other groups were administered on daily basis through tail vein injection.

TABLE 63 inhibition effect of polypeptideIon heterotransplanted human brain tumor SF763 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.89 ± 0.64 | 12 | 23.03 ± 0.81 | 12 | 1.18 ± 0.33 | — |
| taxol | 10 | 20.14 ± 0.43 | 8 | 17.97 ± 0.63 | 6 | 0.28 ± 0.07** | 76.29% |
| polypeptide I (high) | 3 | 19.83 ± 0.58 | 8 | 20.94 ± 0.47 | 8 | 0.47 ± 0.08** | 60.16% |
| polypeptide I (medium) | 1.5 | 20.15 ± 0.52 | 8 | 22.99 ± 0.62 | 8 | 0.34 ± 0.07** | 71.19% |
| polypeptide I (low) | 0.75 | 20.12 ± 0.70 | 8 | 22.90 ± 0.69 | 8 | 0.38 ± 0.06** | 67.80% |

TABLE 64 inhibition effect of polypeptide II on heterotransplanted human brain tumor SF763 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.89 ± 0.64 | 12 | 23.03 ± 0.81 | 12 | 1.18 ± 0.33 | — |
| taxol | 10 | 20.14 ± 0.43 | 8 | 17.97 ± 0.63 | 7 | 0.28 ± 0.07** | 76.29% |
| polypeptide II (high) | 3 | 19.94 ± 0.48 | 8 | 23.24 ± 0.66 | 8 | 0.41 ± 0.14* | 65.48% |
| polypeptide II (medium) | 1.5 | 20.21 ± 0.58 | 8 | 22.88 ± 0.52 | 8 | 0.29 ± 0.07** | 75.02% |
| polypeptide II (low) | 0.75 | 20.01 ± 0.78 | 8 | 22.95 ± 0.52 | 8 | 0.35 ± 0.13** | 70.61% |

TABLE 65 inhibition effect of polypeptide III on heterotransplanted human brain tumor SF763 in nude mice

| group | dose (mg/kg/time) | initial weight (g) | initial number | final weight (g) | final number | tumor weight (g) | tumor inhibition rate |
|---|---|---|---|---|---|---|---|
| control | — | 19.89 ± 0.64 | 12 | 23.03 ± 0.81 | 12 | 1.18 ± 0.33 | — |
| taxol | 10 | 20.14 ± 0.43 | 8 | 17.97 ± 0.63 | 7 | 0.28 ± 0.07** | 76.29% |
| polypeptide III (high) | 0.75 | 19.86 ± 0.48 | 8 | 23.09 ± 0.53 | 8 | 0.31 ± 0.09** | 74.06% |
| polypeptide III (medium) | 0.375 | 20.18 ± 0.64 | 8 | 23.37 ± 0.56 | 8 | 0.24 ± 0.05** | 79.76% |
| polypeptide III (low) | 0.1875 | 19.99 ± 0.62 | 8 | 23.31 ± 0.57 | 8 | 0.32 ± 0.08** | 72.82% |

RESULTS: the inhibition effect of polypeptide I on heterotransplanted human brain tumor SF763 in nude mice is shown in Table 63. The inhibition rate of the taxol group on heterotransplanted human brain tumor SF763 in nude mice was 76.29%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human brain tumor SF763 in nude mice were 60.16%, 71.19% and 67.80% respectively. The tumor volume of mice from all polypeptide groups, including the high-dose group, the medium-dose group and the low-dose group, exhibited extremely significant difference in contrast with that from the negative control group; meanwhile, animals from the polypeptide groups showed no significant change in body weight, and no obvious toxic and side effects were observed in contrast with the negative control group.

The inhibition effect of polypeptide II on heterotransplanted human brain tumor SF763 in nude mice is shown in Table 64. The inhibition rate of the taxol group on heterotransplanted human brain tumor SF763 in nude mice was 76.29%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human brain tumor SF763 in nude mice were 65.48%, 75.02% and 70.61% respectively. The tumor volume of mice from the high-dose group presented significant difference in contrast with that from the negative control group; the tumor volume of mice from both the medium-dose group and the low-dose group presented extremely significant difference in contrast with that from the negative control group; meanwhile, animals from the polypeptide groups showed no significant change in body weight, and no obvious toxic and side effects were observed in contrast with the negative control group.

The inhibition effect of polypeptide III on heterotransplanted human brain tumor SF763 in nude mice is shown in Table 65. The inhibition rate of the taxol group on heterotransplanted human brain tumor SF763 in nude mice was 76.29%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human brain tumor SF763 in nude mice were 74.06%, 79.76% and 72.82% respectively. All polypeptide groups, including the high-dose group, the medium-dose group and the low-dose group, exhibited extremely significant difference in contrast with the negative control group; meanwhile, animals from the polypeptide groups showed no significant change in body weight, and no obvious toxic and side effects were observed in contrast with the negative control group.

Embodiment 25

Test on the Inhibition Effect of Integrin-Blocking Polypeptide I, Polypeptide II and Polypeptide III on Heterotransplanted Human Rectal Cancer Colo 320 in Nude Mice The tumor inoculation process and analysis methods were the same as those mentioned in embodiment 6. Taxol used in the positive control group was administered once every 3 days through tail vein injection, while drugs of all other groups were administered on daily basis through tail vein injection.

TABLE 66 inhibition effect of polypeptideIon heterotransplanted human rectal cancer Colo 320 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.63 | 12 | 23.22 ± 0.50 | 12 | 1.25 ± 0.31 | — |
| taxol | 10 | 19.96 ± 0.59 | 8 | 17.08 ± 0.57 | 7 | 0.29 ± 0.07** | 76.62% |
| endostar (rh-endostatin) | 2.5 | 20.05 ± 0.70 | 8 | 23.05 ± 0.67 | 8 | 0.68 ± 0.28 | 45.41% |
| polypeptide I (high) | 3 | 19.94 ± 0.59 | 8 | 20.99 ± 0.66 | 7 | 0.51 ± 0.09** | 59.20% |
| polypeptide I (medium) | 1.5 | 19.88 ± 0.50 | 8 | 22.87 ± 0.57 | 7 | 0.44 ± 0.05** | 64.80% |
| polypeptide I (low) | 0.75 | 20.21 ± 0.64 | 8 | 23.11 ± 0.61 | 8 | 0.52 ± 0.08** | 58.40% |

TABLE 67 inhibition effect of polypeptide II on heterotransplanted human rectal cancer Colo 320 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.63 | 12 | 23.22 ± 0.50 | 12 | 1.25 ± 0.31 | — |
| taxol | 10 | 19.96 ± 0.59 | 8 | 17.08 ± 0.57 | 7 | 0.29 ± 0.07** | 76.62% |
| endostar (rh-endostatin) | 2.5 | 20.05 ± 0.70 | 8 | 23.05 ± 0.67 | 8 | 0.68 ± 0.28 | 45.41% |
| polypeptide II (high) | 3 | 19.88 ± 0.58 | 8 | 22.99 ± 0.37 | 8 | 0.41 ± 0.09** | 67.41% |
| polypeptide II (medium) | 1.5 | 19.97 ± 0.66 | 8 | 23.10 ± 0.61 | 8 | 0.31 ± 0.03** | 75.42% |
| polypeptide II (low) | 0.75 | 20.07 ± 0.54 | 8 | 22.85 ± 0.61 | 8 | 0.35 ± 0.10** | 72.26% |

TABLE 68 inhibition effect of polypeptide III on heterotransplanted human rectal cancer Colo 320 in nude mice

| group | dose (mg/kg/time) | initial weight (g) | initial number | final weight (g) | final number | tumor weight (g) | tumor inhibition rate |
|---|---|---|---|---|---|---|---|
| control | — | 20.09 ± 0.63 | 12 | 23.22 ± 0.50 | 12 | 1.25 ± 0.31 | — |
| taxol | 10 | 19.96 ± 0.59 | 8 | 17.08 ± 0.57 | 7 | 0.29 ± 0.07** | 76.62% |
| endostar (rh-endostatin) | 2.5 | 20.05 ± 0.70 | 8 | 23.05 ± 0.67 | 8 | 0.68 ± 0.28 | 45.41% |
| polypeptide III (high) | 0.75 | 19.82 ± 0.60 | 8 | 23.14 ± 0.48 | 8 | 0.33 ± 0.08** | 73.51% |
| polypeptide III (medium) | 0.375 | 19.96 ± 0.58 | 8 | 22.93 ± 0.56 | 8 | 0.24 ± 0.05** | 80.89% |

TABLE 68-continued inhibition effect of polypeptide III on heterotransplanted
human rectal cancer Colo 320 in nude mice

| group | dose (mg/kg/time) | initial weight (g) | initial number | final weight (g) | final number | tumor weight (g) | tumor inhibition rate |
|---|---|---|---|---|---|---|---|
| polypeptide III (low) | 0.1875 | 19.87 ± 0.58 | 8 | 22.81 ± 0.60 | 8 | 0.37 ± 0.07** | 70.34% |

RESULTS: the inhibition effect of polypeptide I on heterotransplanted human rectal cancer Colo 320 in nude mice is shown in Table 66. The inhibition rate of the taxol group on heterotransplanted human rectal cancer Colo 320 in nude mice was 76.62%, however, this chemotherapy greatly reduced the body weight of animals; mice treated in this way showed lighter body weight and more apparent toxic and side effects than those from the negative control group and the polypeptide groups. The inhibition rates of polypeptide I at high, medium and low doses on heterotransplanted human rectal cancer Colo 320 in nude mice were 59.20%, 64.80% and 58.40% respectively. All polypeptide groups, including the high-dose group, the medium-dose group and the low-dose group, exhibited extremely significant difference in contrast with the negative control group; meanwhile, animals from the polypeptide groups showed no significant change in body weight, and no obvious toxic and side effects were observed in contrast with the negative control group.

The inhibition effect of polypeptide II on heterotransplanted human rectal cancer Colo 320 in nude mice is shown in Table 67. The inhibition rate of the taxol group on heterotransplanted human rectal cancer Colo 320 in nude mice was 76.62%, however, this chemotherapy greatly reduced the body weight of animals; mice treated in this way showed lighter body weight and more apparent toxic and side effects than those from the negative control group and the polypeptide groups. The inhibition rates of polypeptide II at high, medium and low doses on heterotransplanted human rectal cancer Colo 320 in nude mice were 67.41%, 75.42% and 72.26% respectively. All polypeptide groups, including the high-dose group, the medium-dose group and the low-dose group, exhibited extremely significant difference in contrast with the negative control group; meanwhile, animals from the polypeptide groups showed no significant change in body weight, and no obvious toxic and side effects were observed in contrast with the negative control group.

The inhibition effect of polypeptide III on heterotransplanted human rectal cancer Colo 320 in nude mice is shown in Table 68. The inhibition rate of the taxol group on heterotransplanted human rectal cancer Colo 320 in nude mice was 76.62%, however, this chemotherapy greatly reduced the body weight of animals; mice treated in this way showed lighter body weight and more apparent toxic and side effects than those from the negative control group and the polypeptide groups. The inhibition rates of polypeptide III at high, medium and low doses on heterotransplanted human rectal cancer Colo 320 in nude mice were 73.51%, 80.89% and 70.34% respectively. All polypeptide groups, including the high-dose group, the medium-dose group and the low-dose group, exhibited extremely significant difference in contrast with the negative control group; meanwhile, animals from the polypeptide groups showed no significant change in body weight, and no obvious toxic and side effects were observed in contrast with the negative control group.

Embodiment 26

Test on the In Vivo Immunoprotective Effect of Polypeptide I, Polypeptide II and Polypeptide III on Collagen-Induced Arthritis in Mouse Models Investigating the therapeutic effect of polypeptides disclosed in the present invention on mouse collagen-induced arthritis (CIA) by means of establishing CIA mouse models. Taking specific, pathogen-free DBA/1 mice (provided by Sino-British SIPPR/BK Lab. Animal Ltd, Shanghai, China; animal production license: SCXK (Shanghai) 2008-0016) as animal subjects, randomly dividing 7-or 8-week-old male mice with body weight of 18-22 g into the normal control group, model control group, polypeptide I groups including the low-dose (0.2 mg/kg), medium-dose (0.4 mg/kg) and high-dose (0.8 mg/kg) subgroups, polypeptide II groups including the low-dose (0.2 mg/kg), medium-dose (0.4 mg/kg) and high-dose (0.8 mg/kg) subgroups, polypeptide III groups including the low-dose (0.2 mg/kg), medium-dose (0.4 mg/kg) and high-dose (0.8 mg/kg) subgroups, and the (methotrexate 1 mg/kg) positive control group. Apart from the normal control group, CIA mouse models were established for all test groups on day 0. Predissolving chicken cartilage collagen type III (cIII) in 0.1 mol/l acetic acid to prepare 4 mg/ml collagen solution, and then keeping the solution at 4° C. overnight. On day 0 of the experiment, sufficiently emulsifying type III collagen solution with isovolumetric complete Freund's adjuvant (CFA) containing 4 mg/ml myeobaeterium tuberculosis (strain H37Rv); anesthetizing DBA/1 mice and intradermically injecting 50 μl emulsion at the tail of each mouse; on day 21 of the experiment, inducing the secondary immune response by intradermically injecting 50 μl emulsion at the tail of each mouse again; the emulsion used for said secondary immune response is prepared by sufficiently emulsifying 4 mg/ml type III collagen (cIII) and isovolumetric incomplete Freund's adjuvant (IFA). On day 30 of the experiment, hypodermically administering drugs for each mouse: all polypeptide groups were divided into low-dose (0.2 mg/kg for polypeptide I and polypeptide II, and 0.1 mg/kg for polypeptide III), medium-dose (0.4 mg/kg for polypeptide I and polypeptide II, and 0.2 mg/mg for polypeptide III) and high-dose (0.8 mg/kg for polypeptide I and polypeptide II, and 0.4 mg/kg for polypeptide III) subgroups, twice a day, 10 days in succession; mice from the positive control group were administered with methotrexate (1 mg/kg), once every 5 days, three times in total; mice from the normal control group and model control group were administered only with physiological saline on daily basis, 10 days in succession. During day 21 to day 70 of the experiment, evaluating the impact of the drugs on CIA mouse models by measuring the body weight, scoring the joint change and examining left and right hind ankles, once every 3 days. On day 70 of the experiment, killing mice through cervical dislocation.

The arthritis was evaluated in accordance with the following criteria:

1) joint scoring: four legs: scoring in terms of level 0 to level 4, 5 levels in total. Specifically: 0=no red spot or swelling; 1=small red spot or slight swelling appeared at one of front/hind toe joints); 2=red spot or swelling appeared at more than one front/hind toe joints; 3=paw swelling beneath ankles; 4=paw swelling including ankles. Four feet were scored independently, with 16 as the highest point. Scoring was conducted during day 21 to day 70 of the experiment, once every 3 days, and recording all the data.

2) measuring the diameter of mouse ankles

Measuring the diameter of both left and right ankles (inside-outside) and the thickness of paws of mice with a vernier caliper before the model establishment and during day 21 to day 70 of the experiment, once every 3 days; recording all the data.

The measured data were listed in the form of mean and standard deviation (mean±SD), conducting T-test with SPSS11.0 software for all test groups and control groups, wherein * referred to p<0.05 and **p<0.01.

RESULTS: comparing the model mice with the normal mice. On day 0 of the experiment, the model mice were firstly hypodermically injected at the tail with an emulsion made by collagen and isovolumetric CFA (containing deactivated myeobaeterium tuberculosis); on day 21 of the experiment, the model mice were again hypodermically injected at the tail with an emulsion made by collagen and isovolumetric IFA; on day 27 of the experiment, swelling at paws appeared on CIA mice and points for arthritis scoring started increasing; the highest degree of swelling on model mice appeared on day 45-60; in addition, the body weight of model mice stopped increasing since day 35 and even slightly decreased later on.

Polypeptide I at all doses presented in vivo immunoprotective effect on CIA mouse models. As is shown in Table 69: the swelling degree of paws in mice from the positive control group, and all high-dose, medium-dose and low-dose polypeptide I groups exhibited extremely significant difference (p<0.01) in contrast with that from the model control group; the result was statistically significant. The swelling degree of joints in mice from the positive control group and all high-dose, medium-dose and low-dose polypeptide I groups exhibited extremely significant difference (p<0.01) in contrast with that from the model control group; the result was statistically significant. The joint scoring of mice from all high-dose, medium-dose and low-dose polypeptide I was significantly lower (p<0.01) than that from the model control group; the result was statistically significant.

TABLE 69 in vivo immunoprotective effect of polypeptide I on CIA mouse models

| group | number (n) | dose (mg/kg) | swelling of paws (mm) | swelling of joints (mm) | clinical scoring |
| --- | --- | --- | --- | --- | --- |
| normal control | 10 | — | 0.15 ± 0.07** | 0.14 ± 0.04** | 0.00 ± 0.00** |
| model control | 10 | — | 2.12 ± 0.37 | 1.90 ± 0.40 | 15.5 ± 2.3 |
| positive control | 10 | 1 | 0.90 ± 0.19** | 0.75 ± 0.17** | 8.3 ± 1.2** |
| Polypeptide I(high) | 10 | 0.8 | 1.31 ± 0.26** | 1.05 ± 0.31** | 11.4 ± 1.6** |
| Polypeptide I(medium) | 10 | 0.4 | 0.94 ± 0.18** | 0.79 ± 0.17** | 9.1 ± 1.4** |
| Polypeptide I(low) | 10 | 0.2 | 1.21 ± 0.22** | 0.97 ± 0.23** | 9.7 ± 1.5** |

* referring to p < 0.05,
**referring to p < 0.01.

Polypeptide II at all doses presented in vivo immunoprotective effect on CIA mouse models. As is shown in Table 70: the swelling degree of paws in mice from the positive control group, and all high-dose, medium-dose and low-dose polypeptide II groups exhibited extremely significant difference (p<0.01) in contrast with that from the model control group; the result was statistically significant. The swelling degree of joints in mice from the positive control group and all high-dose, medium-dose and low-dose polypeptide II exhibited extremely significant difference (p<0.01) in contrast with that from the model control group; the result was statistically significant. The joint scoring of mice from all high-dose, medium-dose and low-dose polypeptide II was extremely lower (p<0.01) than that from the model control group; the result was statistically significant.

TABLE 70 in vivo immunoprotective effect of polypeptide II on CIA mouse models

| group | number (n) | dose (mg/kg) | swelling of paws (mm) | swelling of joints (mm) | clinical scoring |
| --- | --- | --- | --- | --- | --- |
| normal control | 10 | — | 0.13 ± 0.03** | 0.13 ± 0.03** | 0.00 ± 0.00** |
| model control | 10 | — | 1.90 ± 0.38 | 1.86 ± 0.38 | 15.55 ± 2.33 |
| positive control | 10 | 1 | 0.90 ± 0.18** | 0.75 ± 0.18** | 8.01 ± 1.21** |
| polypeptide II (high) | 10 | 0.8 | 1.44 ± 0.29** | 1.16 ± 0.32** | 10.73 ± 1.65** |

TABLE 70-continued in vivo immunoprotective effect of polypeptide II on CIA mouse models

| group | number (n) | dose (mg/kg) | swelling of paws (mm) | swelling of joints (mm) | clinical scoring |
|---|---|---|---|---|---|
| polypeptide II (medium) | 10 | 0.4 | 0.99 ± 0.20** | 0.83 ± 0.21** | 9.269 ± 1.3** |
| polypeptide II (low) | 10 | 0.2 | 1.12 ± 0.32** | 0.95 ± 0.24** | 9.82 ± 1.48** |

\* referring to $p < 0.05$,
\*\*referring to $p < 0.01$.

Polypeptide III at all doses presented in vivo immunoprotective effect on CIA mouse models. As is shown in Table 71: the swelling degree of paws in model mice from the positive control group, and all high-dose, medium-dose and low-dose polypeptide III groups exhibited extremely significant difference ($p<0.01$) in contrast with that from the model control group; the result was statistically significant. The swelling degree of joints in mice from the positive control group and all high-dose, medium-dose and low-dose polypeptide III exhibited extremely significant difference ($p<0.01$) in contrast with that from the model control group; the result was statistically significant. The joint scoring of mice from all high-dose, medium-dose and low-dose polypeptide III was extremely lower ($p<0.01$) than that from the model control group; the result was statistically significant.

TABLE 71 in vivo immunoprotective effect of polypeptide III on CIA mouse models

| group | number (n) | dose (mg/kg) | swelling of paws (mm) | swelling of joints (mm) | clinical scoring |
|---|---|---|---|---|---|
| normal control | 10 | — | 0.13 ± 0.03** | 0.13 ± 0.03** | 0.00 ± 0.00** |
| model control | 10 | — | 1.90 ± 0.38 | 1.86 ± 0.38 | 15.55 ± 2.33 |
| positive control | 10 | 1 | 0.90 ± 0.18** | 0.75 ± 0.18** | 8.01 ± 1.21** |
| Polypeptide III(high) | 10 | 0.4 | 1.23 ± 0.25** | 1.05 ± 0.26** | 10.41 ± 1.56** |
| polypeptide III(medium) | 10 | 0.2 | 0.85 ± 0.17** | 0.68 ± 0.19** | 9.13 ± 1.37** |
| polypeptide III(low) | 10 | 0.1 | 1.03 ± 0.21** | 0.92 ± 0.27** | 9.73 ± 1.46** |

\* referring to $p < 0.05$,
\*\*referring to $p < 0.01$.

CONCLUSION: polypeptide I, polypeptide II and polypeptide III have therapeutic effect on collagen-induce arthritis in mice.

Embodiment 27

Test on the In Vivo Immunoprotective Effect of Polypeptide I, Polypeptide II and Polypeptide III on Adjuvant Arthritis in Rat Models Investigating the therapeutic effect of polypeptides disclosed in the present invention on adjuvant-induce arthritis (AIA) in rats by means of establishing AIA rat models. Taking specific, pathogen-free SD rats (provided by Sino-British SIPPR/BK Lab Animal Ltd, Shanghai, China; animal production license: SCXK (Shanghai) 2008-0016) as animal subjects, randomly dividing male rats with body weight of 140-160 g into the normal control group, model control group, polypeptide I groups including the low-dose (0.4 mg/kg), medium-dose (0.8 mg/kg) and high-dose (1.6 mg/kg) subgroups, polypeptide II groups including the low-dose (0.4 mg/kg), medium-dose (0.8 mg/kg) and high-dose (1.6 mg/kg) subgroups, polypeptide III groups including the low-dose (0.2 mg/kg), medium-dose (0.4 mg/kg) and high-dose (0.8 mg/kg) subgroups, and the (methotrexate 1 mg/kg) positive control group. Apart from the normal control group, AIA rat models were established for all test groups on day 0 by injecting at the left hind paw of all rats with 0.08 ml CFA containing 10 mg/ml deactivated myeobaeterium tuberculosis (strain H37RA). On day 10 of the experiment, hypodermically administering drugs for each rat: all polypeptide groups were divided into low-dose (0.4 mg/kg for polypeptide I and polypeptide II, and 0.2 mg/kg for polypeptide III), medium-dose (0.8 mg/kg for Polypeptide I and Polypeptide II, and 0.4 mg/kg for polypeptide III) and high-dose (1.6 mg/kg for polypeptide I and polypeptide II, and 0.8 mg/kg for polypeptide III) subgroups, twice a day, 10 days in succession; rats from the positive control group were administered with methotrexate (1 mg/kg), once every 5 days, three times in total; rats from the normal control group and model control group were administered only with physiological saline on daily basis, 10 days in succession. On day 8, 11, 14, 17, 20, 23 and 26 of the experiment, evaluating the impact of the drugs on AIA rat models by examining the diameter of both left and right hind ankles.

The arthritis was evaluated in accordance with the following criteria:
1) joint scores: four legs: scoring in terms of level 0 to level 4, 5 levels in total. Specifically: 0=no red spot or swelling; 1=small red spot or slight swelling appeared at one of front/hind toe joints); 2=red spot or swelling appeared at more than one front/hind toe joints; 3=paw swelling beneath ankles; 4=paw swelling including ankles. Four feet were scored independently, with 16 as the highest point.

Scoring joints on day 8, 11, 14, 17, 20, 23 and 26 of the experiment and recording all the data.

2) measuring the diameter of rat ankles

Measuring the diameter of both left and right ankles (inside-outside) and the thickness of paws of mice with a vernier caliper before the model establishment and during day 11 to day 23 of the experiment, once every 26 days; recording all the data.

The measured data were listed in the form of mean and standard deviation (mean±SD), conducting T-test with SPSS11.0 software for all test groups and control groups, wherein * referred to p<0.05 and **p<0.01.

RESULTS: comparing the model rats with the normal rats. The primary arthritis appeared at the left hind paw of model rats soon after injection of CFA containing deactivated myeobaeterium tuberculosis at the left hind paw, along with apparent swelling and ulceration; the secondary arthritis appeared at the right high paw about 10 days later, with increasingly high scores; meanwhile, apparent angiogenesis occurred at rat ears, with obvious redness and swelling; swelling also appeared at tail joints.

Polypeptide I at all doses presented in vivo immunoprotective effect on AIA rat models. As is shown in Table 72: the diameter of the left hind paw of rats from both the positive control group and polypeptide I medium-dose group presented extremely significant difference (p<0.01) in contrast with that from the model control group; the diameter of the left hind paw of rats from both polypeptide I low-dose group and polypeptide I high-dose group presented significant difference (p<0.05) in contrast with that from the model control group; the result was statistically significant. The diameter of the right hind paw of rats from the positive control group, as well as polypeptide I low-dose, medium-dose and high-dose groups presented significant difference (p<0.05) in contrast with that from the model control group. The joint scoring of rats from all high-dose, medium-dose and low-dose groups of polypeptide I was significantly lower (p<0.05) than that from the model control group; the result was statistically significant.

Polypeptide II at all doses presented in vivo immunoprotective effect on AIA rat models. As is shown in Table 73: the diameter of the left hind paw of rats from both the positive control group and polypeptide II medium-dose group presented extremely significant difference (p<0.01) in contrast with that from the model control group; the diameter of the left hind paw of rats from both polypeptide II low-dose group and polypeptide II high-dose group presented significant difference (p<0.05) in contrast with that from the model control group; the result was statistically significant. The swelling degree of the right paw of rats from the positive control group, as well as polypeptide II low-dose, medium-dose and high-dose groups presented significant difference (p<0.05) in contrast with that from the model control group. The joint scoring of rats from all high-dose, medium-dose and low-dose groups of polypeptide II was significantly lower (p<0.05) than that from the model control group; the result was statistically significant.

TABLE 73 in vivo immunoprotective effect of polypeptide II on AIA rat models

| group | number (n) | dose (mg/kg) | swelling of left paw (mm) | swelling of right paw (mm) | clinical scoring |
|---|---|---|---|---|---|
| normal control | 10 | — | 0.90 ± 0.17** | 0.38 ± 0.11** | 0.00 ± 0.00** |
| model control | 10 | — | 7.01 ± 1.42 | 3.21 ± 0.69 | 13.11 ± 2.62 |
| positive control | 10 | 1 | 3.51 ± 0.77** | 0.59 ± 0.17** | 5.02 ± 1.11* |
| polypeptide II (high) | 10 | 1.6 | 4.69 ± 0.94* | 1.39 ± 0.36* | 7.21 ± 1.44* |
| polypeptide II (medium) | 10 | 0.8 | 3.88 ± 0.75** | 0.82 ± 0.24* | 5.57 ± 1.25* |
| polypeptide II (low) | 10 | 0.4 | 4.42 ± 0.86* | 1.1 ± 0.23* | 6.34 ± 1.22* |

*referring to p < 0.05,
**referring to p < 0.01.

CONCLUSION: polypeptide II has therapeutic effect on adjuvant-induced arthritis in rats Polypeptide III at all doses presented in vivo immunoprotective effect on AIA rat models. As is shown in Table 74: the diameter of the left hind paw of rats from both the positive control group and polypeptide III medium-dose group presented extremely significant difference (p<0.01) in contrast with that from the model control group; the diameter of the left hind paw of rats from both polypeptide III low-dose group and polypeptide I high-dose group presented significant difference (p<0.05) in contrast with that from the model control group; the result was statistically significant. The diameter of the right hind paw of rats from the positive control group, as well as polypeptide III low-dose, medium-dose and high-dose groups presented significant difference (p<0.05) in contrast with that from the model control group. The joint scoring of rats from all high-dose, medium-dose and low-dose groups of polypeptide III was significantly lower (p<0.05) than that from the model control group; the result was statistically significant.

TABLE 72 in vivo immunoprotective effect of polypeptide I on AIA rat models

| group | number (n) | dose (mg/kg) | swelling of left paws (mm) | swelling of right paws (mm) | clinical scoring |
|---|---|---|---|---|---|
| normal control | 10 | — | 0.79 ± 0.18** | 0.56 ± 0.08** | 0.0 ± 0.0** |
| model control | 10 | — | 7.11 ± 1.4 | 3.38 ± 0.94 | 13.5 ± 2.6 |
| positive control | 10 | 1 | 3.52 ± 0.72** | 0.63 ± 0.19** | 4.8 ± 1.0* |
| polypeptide I(high) | 10 | 1.6 | 4.81 ± 0.95* | 1.35 ± 0.30* | 7.0 ± 1.2* |
| polypeptide I(medium) | 10 | 0.8 | 3.83 ± 0.76** | 0.94 ± 0.18* | 5.5 ± 1.0* |
| polypeptide I(low) | 10 | 0.4 | 4.25 ± 0.85* | 1.36 ± 0.31* | 7.1 ± 1.1* |

*referring to p < 0.05,
**referring to p < 0.01.

TABLE 74 in vivo immunoprotective effect of polypeptide III on AIA rat models

| group | number (n) | dose (mg/kg) | swelling of left paw (mm) | swelling of right paw (mm) | clinical scoring |
|---|---|---|---|---|---|
| normal control | 10 | — | 0.90 ± 0.17** | 0.38 ± 0.11** | 0.00 ± 0.00** |
| model control | 10 | — | 7.01 ± 1.42 | 3.21 ± 0.69 | 13.11 ± 2.62 |
| positive control | 10 | 1 | 3.51 ± 0.77** | 0.59 ± 0.17** | 5.02 ± 1.11* |
| polypeptide III(high) | 10 | 0.8 | 4.65 ± 0.94* | 1.17 ± 0.26* | 6.33 ± 1.20* |
| polypeptide III(medium) | 10 | 0.4 | 3.72 ± 0.76** | 0.73 ± 0.21* | 5.29 ± 1.04* |
| polypeptide IIII(low) | 10 | 0.2 | 4.0 ± 0.74* | 1.09 ± 0.28* | 5.69 ± 1.12* |

*referring to p < 0.05,
**referring to p < 0.01.

CONCLUSION: polypeptide I, polypeptide II and polypeptide III have therapeutic effect on adjuvant-induced arthritis in rats.

What is claimed is:

1. An integrin-blocking polypeptide comprising the amino acid sequence of SEQ ID NO: 3.

2. The integrin-blocking polypeptide as defined in claim 1, further comprising an adjuvant adopted for covalent connection with said integrin-blocking polypeptide, wherein the adjuvant is bovine serum albumin (BSA), human serum albumin (HSA) or polyethylene glycol (PEG).

3. A method of treating a tumor in a subject in need thereof, comprising the step of administering an anti-tumor drug comprising an integrin-blocking polypeptide to the subject, wherein the integrin-blocking polypeptide is a polypeptide comprising SEQ ID NO: 3 or a polypeptide consisting of SEQ ID NO: 2, and wherein the tumor is melanoma, sarcoma or a primary or secondary cancer originated from head and neck region, brain, thyroid, esophagus, pancreas, lung, liver, stomach, breast, kidney, gallbladder, colon, rectum, ovary, cervix, uterus, prostate, bladder or testicle.

4. The method as defined in claim 3, wherein the anti-tumor drug is administered via a route selected from the group consisting of hypodermic injection, intramuscular injection, intravenous injection, intravenous drip, oral administration and nasal spray.

5. An integrin-blocking polypeptide consisting of an amino acid sequence selected from the group consisting of SEQ ID NO: 2 and SEQ ID NO: 3.

6. An integrin-blocking polypeptide consisting of:
an amino acid sequence selected from the group consisting of SEQ ID NO: 2 and SEQ ID NO: 3; and
an adjuvant covalently connected to the amino acid sequence, wherein the adjuvant is selected from the group consisting of bovine serum albumin (BSA), human serum albumin (HSA) and polyethylene glycol (PEG).

* * * * *

UNITED STATES PATENT AND TRADEMARK OFFICE
CERTIFICATE OF CORRECTION

PATENT NO. : 9,458,203 B2
APPLICATION NO. : 14/368960
DATED : October 4, 2016
INVENTOR(S) : Hanmei Xu et al.

Page 1 of 3

It is certified that error appears in the above-identified patent and that said Letters Patent is hereby corrected as shown below:

In the Specification

Column 1, Line 15, please change
"This follows relates" to --The following relates--

Column 2, Line 24, please change
"short,)." to --short).--

Column 2, Line 63, please change
"angiogenesis-a" to --angiogenesis, a--

Column 3, Line 1, please change
"effect on" to --effects on--

Column 3, Line 59, please change
"cells-the" to --cells, the--

Column 3, Line 67, please change
"in a health" to --in healthy--

Column 4, Line 41, please change
"realize effective" to --realize an effective--

Column 4, Line 44, please change
"cell-cell" to --cell, cell--

Column 4, Line 52, please change
"angiogenesis-a" to --angiogenesis, a--

Signed and Sealed this
Sixteenth Day of May, 2017

Michelle K. Lee
*Director of the United States Patent and Trademark Office*

CERTIFICATE OF CORRECTION (continued)
U.S. Pat. No. 9,458,203 B2

Column 4, Line 53, please change
"Integrin-inhibiting" to --integrin-inhibiting--

Column 4, Line 64, please change
"detected out that" to --detected that--

Column 6, Line 59, please change
"were undergone" to --were undergoing--

Column 7, Line 4, please change
"effect in" to --effects in--

Column 7, Line 42, please change
"angiogenesis-a" to --angiogenesis, a--

Column 7, Line 51, please change
"tumors-it" to --tumors, it--

Column 7, Line 52, please change
"have low" to --having low--

Column 8, Line 17, please change
"side effect" to --side effects--

Column 12, Line 10, please change
"at the room" to --at room--

Column 12, Line 26, please change
"at the room" to --at room--

Column 12, Line 27, please change
"at the room" to --at room--

Column 16, Line 65, please change
"all does" to --all doses--

Column 38, Line 8, please change
"IIIat" to --III at--

Column 66, Table 58/1, Line 31, please change
"I Ion" to --II on--

Column 67, Table 59/1, Line 3 (approx.), please change
"II Ion" to --III on--

CERTIFICATE OF CORRECTION (continued)
U.S. Pat. No. 9,458,203 B2

Column 69, Line 36, please change
"polypeptideIon" to --polypeptide I on--

Column 71, Table 63/1, Line 3 (approx.), please change
"polypeptideIon" to --polypeptide I on--

Column 73, Table 66/1, Line 19 (approx.), please change
"polypeptideIon" to --polypeptide I on--

Column 79, Line 46, please change
"collagen-induce" to --collagen-induced--

```
                       SEQUENCE LISTING

<160> NUMBER OF SEQ ID NOS: 35

<210> SEQ ID NO 1
<211> LENGTH: 43
<212> TYPE: PRT
<213> ORGANISM: Artificial Sequence
<220> FEATURE:
<223> OTHER INFORMATION: anti-angiogenic integrin blocker

<400> SEQUENCE: 1

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala
        35                  40

<210> SEQ ID NO 2
<211> LENGTH: 50
<212> TYPE: PRT
<213> ORGANISM: Artificial Sequence
<220> FEATURE:
<223> OTHER INFORMATION: Anti-angiogenic integrin blocker

<400> SEQUENCE: 2

Arg Gly Asp Gly Gly Gly Gly Phe Gln Pro Val Leu His Leu Val Ala
1               5                   10                  15

Leu Asn Ser Pro Leu Ser Gly Gly Met Arg Gly Ile Arg Gly Ala Asp
            20                  25                  30

Phe Gln Cys Phe Gln Gln Ala Arg Ala Val Gly Leu Ala Gly Thr Phe
        35                  40                  45

Arg Ala
    50

<210> SEQ ID NO 3
<211> LENGTH: 50
<212> TYPE: PRT
<213> ORGANISM: Artificial Sequence
<220> FEATURE:
<223> OTHER INFORMATION: anti-angiogenic integrin blocker
```

-continued

<400> SEQUENCE: 3

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Gly Gly Gly Gly Arg
        35                  40                  45

Gly Asp
    50

<210> SEQ ID NO 4
<211> LENGTH: 47
<212> TYPE: PRT
<213> ORGANISM: Artificial Sequence
<220> FEATURE:
<223> OTHER INFORMATION: anti-angiogenic integrin blocker

<400> SEQUENCE: 4

Arg Gly Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala Phe
        35                  40                  45

<210> SEQ ID NO 5
<211> LENGTH: 56
<212> TYPE: PRT
<213> ORGANISM: Artificial Sequence
<220> FEATURE:
<223> OTHER INFORMATION: anti-angiogenic integrin blocker

<400> SEQUENCE: 5

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Phe Gly Gly Gly Gly
        35                  40                  45

Ala Cys Arg Gly Asp Cys Phe Cys
    50                  55

<210> SEQ ID NO 6
<211> LENGTH: 12
<212> TYPE: PRT
<213> ORGANISM: Artificial Sequence
<220> FEATURE:
<223> OTHER INFORMATION: anti-angiogenic integrin blocker

<400> SEQUENCE: 6

Gly Gly Gly Gly Ala Cys Arg Gly Asp Cys Phe Cys
1               5                   10

<210> SEQ ID NO 7
<211> LENGTH: 44
<212> TYPE: PRT
<213> ORGANISM: Artificial Sequence
<220> FEATURE:
<223> OTHER INFORMATION: anti-angiogenic integrin blocker

```
<400> SEQUENCE: 7

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Phe
        35                  40

<210> SEQ ID NO 8
<211> LENGTH: 53
<212> TYPE: PRT
<213> ORGANISM: Artificial Sequence
<220> FEATURE:
<223> OTHER INFORMATION: anti-angiogenic integrin blocker

<400> SEQUENCE: 8

Ala Cys Asp Cys Arg Gly Asp Cys Phe Cys Phe Gln Pro Val Leu His
1               5                   10                  15

Leu Val Ala Leu Asn Ser Pro Leu Ser Gly Gly Met Arg Gly Ile Arg
            20                  25                  30

Gly Ala Asp Phe Gln Cys Phe Gln Gln Ala Arg Ala Val Gly Leu Ala
        35                  40                  45

Gly Thr Phe Arg Ala
    50

<210> SEQ ID NO 9
<211> LENGTH: 57
<212> TYPE: PRT
<213> ORGANISM: Artificial Sequence
<220> FEATURE:
<223> OTHER INFORMATION: anti-angiogenic integrin blocker

<400> SEQUENCE: 9

Ala Cys Asp Cys Arg Gly Asp Cys Phe Cys Gly Gly Gly Gly Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala
    50                  55

<210> SEQ ID NO 10
<211> LENGTH: 46
<212> TYPE: PRT
<213> ORGANISM: Artificial Sequence
<220> FEATURE:
<223> OTHER INFORMATION: anti-angiogenic integrin blocker

<400> SEQUENCE: 10

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Arg Gly Asp
        35                  40                  45

<210> SEQ ID NO 11
<211> LENGTH: 57
<212> TYPE: PRT
<213> ORGANISM: Artificial Sequence
```

```
<220> FEATURE:
<223> OTHER INFORMATION: anti-angiogenic integrin blocker

<400> SEQUENCE: 11

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Gly Gly Gly Ala
        35                  40                  45

Cys Asp Cys Arg Gly Asp Cys Phe Cys
    50                  55

<210> SEQ ID NO 12
<211> LENGTH: 53
<212> TYPE: PRT
<213> ORGANISM: Artificial Sequence
<220> FEATURE:
<223> OTHER INFORMATION: anti-angiogenic integrin blocker

<400> SEQUENCE: 12

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Ala Cys Asp Cys Arg
        35                  40                  45

Gly Asp Cys Phe Cys
    50

<210> SEQ ID NO 13
<211> LENGTH: 46
<212> TYPE: PRT
<213> ORGANISM: Artificial Sequence
<220> FEATURE:
<223> OTHER INFORMATION: anti-angiogenic integrin blocker

<400> SEQUENCE: 13

Arg Gly Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala
        35                  40                  45

<210> SEQ ID NO 14
<211> LENGTH: 7
<212> TYPE: PRT
<213> ORGANISM: Artificial Sequence
<220> FEATURE:
<223> OTHER INFORMATION: Integrin ligand sequence

<400> SEQUENCE: 14

Arg Gly Asp Gly Gly Gly Gly
1               5

<210> SEQ ID NO 15
<211> LENGTH: 10
<212> TYPE: PRT
<213> ORGANISM: Artificial Sequence
<220> FEATURE:
<223> OTHER INFORMATION: integrin blocker
```

```
<400> SEQUENCE: 15

Ala Cys Asp Cys Arg Gly Asp Cys Phe Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: integrin blocker

<400> SEQUENCE: 16

Ala Cys Asp Cys Arg Gly Asp Cys Phe Cys Gly Gly Gly Gly
1               5                   10

<210> SEQ ID NO 17
<211> LENGTH: 45
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: MISC_FEATURE
<222> LOCATION: (1)..(1)
<223> OTHER INFORMATION: One or more polypeptides in a sequence or a
      polypeptide sequence containing Arg-Gly-Asp
<220> FEATURE:
<221> NAME/KEY: MISC_FEATURE
<222> LOCATION: (45)..(45)
<223> OTHER INFORMATION: One or more polypeptides in a sequence or a
      polypeptide sequence containing Arg-Gly-Asp

<400> SEQUENCE: 17

Xaa Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Xaa
        35                  40                  45

<210> SEQ ID NO 18
<211> LENGTH: 44
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: MISC_FEATURE
<222> LOCATION: (1)..(1)
<223> OTHER INFORMATION: One or more polypeptides in a sequence or a
      polypeptide sequence containing Arg-Gly-Asp

<400> SEQUENCE: 18

Xaa Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala
        35                  40

<210> SEQ ID NO 19
<211> LENGTH: 44
<212> TYPE: PRT
<213> ORGANISM: Artificial Sequence
<220> FEATURE:
<223> OTHER INFORMATION: anti-angiogenic integrin blocker
```

```
<220> FEATURE:
<221> NAME/KEY: MISC_FEATURE
<222> LOCATION: (44)..(44)
<223> OTHER INFORMATION: One or more polypeptides in a sequence or a
      polypeptide sequence containing Arg-Gly-Asp

<400> SEQUENCE: 19

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Xaa
        35                  40

<210> SEQ ID NO 20
<211> LENGTH: 43
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: bovine serum albumin, human serum albumen or
      polyethylene glycol
<220> FEATURE:
<221> NAME/KEY: BINDING
<222> LOCATION: (43)..(43)
<223> OTHER INFORMATION: bovine serum albumin, human serum albumen or
      polyethylene glycol

<400> SEQUENCE: 20

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala
        35                  40

<210> SEQ ID NO 21
<211> LENGTH: 45
<212> TYPE: PRT
<213> ORGANISM: Artificial Sequence
<220> FEATURE:
<223> OTHER INFORMATION: Anti-angiogenic integrin blocker
<220> FEATURE:
<221> NAME/KEY: BINDING
<222> LOCATION: (1)..(1)
<223> OTHER INFORMATION: Human serum albumen, bovine serum albumen or
      polyethylene glycol
<220> FEATURE:
<221> NAME/KEY: BINDING
<222> LOCATION: (45)..(45)
<223> OTHER INFORMATION: Human serum albumen, bovine serum albumen or
      polyethylene glycol

<400> SEQUENCE: 21

Xaa Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Xaa
        35                  40                  45
```

```
<210> SEQ ID NO 22
<211> LENGTH: 44
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: bovine serum albumen, human serum albumen,
      polyethylene glycol
<220> FEATURE:
<221> NAME/KEY: BINDING
<222> LOCATION: (44)..(44)
<223> OTHER INFORMATION: bovine serum albumen, human serum albumen,
      polyethylene glycol

<400> SEQUENCE: 22

Xaa Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala
        35                  40

<210> SEQ ID NO 23
<211> LENGTH: 44
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: bovine serum albumen, human serum albumen,
      polyethylene glycol
<220> FEATURE:
<221> NAME/KEY: BINDING
<222> LOCATION: (44)..(44)
<223> OTHER INFORMATION: bovine serum albumen, human serum albumen,
      polyethylene glycol

<400> SEQUENCE: 23

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Xaa
        35                  40

<210> SEQ ID NO 24
<211> LENGTH: 50
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (50)..(50)
<223> OTHER INFORMATION: human serum albumen, bovine serum albumen,
      polyethylene glycol
```

-continued

```
<400> SEQUENCE: 24

Arg Gly Asp Gly Gly Gly Phe Gln Pro Val Leu His Leu Val Ala
1               5                   10                  15

Leu Asn Ser Pro Leu Ser Gly Gly Met Arg Gly Ile Arg Gly Ala Asp
            20                  25                  30

Phe Gln Cys Phe Gln Gln Ala Arg Ala Val Gly Leu Ala Gly Thr Phe
        35                  40                  45

Arg Ala
    50

<210> SEQ ID NO 25
<211> LENGTH: 50
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (50)..(50)
<223> OTHER INFORMATION: human serum albumen, bovine serum albumen,
      polyethylene glycol

<400> SEQUENCE: 25

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Gly Gly Gly Arg
        35                  40                  45

Gly Asp
    50

<210> SEQ ID NO 26
<211> LENGTH: 47
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (47)..(47)
<223> OTHER INFORMATION: human serum albumen, bovine serum albumen,
      polyethylene glycol

<400> SEQUENCE: 26

Arg Gly Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala Phe
        35                  40                  45
```

```
<210> SEQ ID NO 27
<211> LENGTH: 56
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (56)..(56)
<223> OTHER INFORMATION: human serum albumen, bovine serum albumen,
      polyethylene glycol

<400> SEQUENCE: 27

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Phe Gly Gly Gly
        35                  40                  45

Ala Cys Arg Gly Asp Cys Phe Cys
    50                  55

<210> SEQ ID NO 28
<211> LENGTH: 44
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (44)..(44)
<223> OTHER INFORMATION: human serum albumen, bovine serum albumen,
      polyethylene glycol

<400> SEQUENCE: 28

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Phe
        35                  40

<210> SEQ ID NO 29
<211> LENGTH: 53
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<220> FEATURE:
<221> NAME/KEY: BINDING
<222> LOCATION: (53)..(53)
```

<400> SEQUENCE: 29

Ala Cys Asp Cys Arg Gly Asp Cys Phe Cys Phe Gln Pro Val Leu His
1               5                   10                  15

Leu Val Ala Leu Asn Ser Pro Leu Ser Gly Gly Met Arg Gly Ile Arg
            20                  25                  30

Gly Ala Asp Phe Gln Cys Phe Gln Gln Ala Arg Ala Val Gly Leu Ala
        35                  40                  45

Gly Thr Phe Arg Ala
    50

<210> SEQ ID NO 30
<211> LENGTH: 57
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (57)..(57)
<223> OTHER INFORMATION: human serum albumen, bovine serum albumen,
      polyethylene glycol

<400> SEQUENCE: 30

Ala Cys Asp Cys Arg Gly Asp Cys Phe Cys Gly Gly Gly Gly Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala
    50                  55

<210> SEQ ID NO 31
<211> LENGTH: 46
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (46)..(46)
<223> OTHER INFORMATION: human serum albumen, bovine serum albumen,
      polyethylene glycol

<400> SEQUENCE: 31

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Arg Gly Asp
        35                  40                  45

-continued

```
<210> SEQ ID NO 32
<211> LENGTH: 57
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: binding
<222> LOCATION: (1)..(1)
<223> OTHER INFORMATION: human serum albumen, bovine serum albumen,
      polyethylene glycol
<220> FEATURE:
<221> NAME/KEY: binding
<222> LOCATION: (57)..(57)
<223> OTHER INFORMATION: human serum albumen, bovine serum albumen,
      polyethylene glycol

<400> SEQUENCE: 32

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Gly Gly Gly Ala
        35                  40                  45

Cys Asp Cys Arg Gly Asp Cys Phe Cys
    50                  55

<210> SEQ ID NO 33
<211> LENGTH: 46
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (46)..(46)
<223> OTHER INFORMATION: human serum albumen, bovine serum albumen,
      polyethylene glycol

<400> SEQUENCE: 33

Arg Gly Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala
        35                  40                  45

<210> SEQ ID NO 34
<211> LENGTH: 53
<212> TYPE: PRT
<213> ORGANISM: Artificial Sequence
<220> FEATURE:
<223> OTHER INFORMATION: anti-angiogenic integrin blocker
<220> FEATURE:
<221> NAME/KEY: BINDING
<222> LOCATION: (1)..(1)
<223> OTHER INFORMATION: human serum albumen, bovine serum albumen,
      polyethylene glycol
<220> FEATURE:
<221> NAME/KEY: BINDING
<222> LOCATION: (53)..(53)
<223> OTHER INFORMATION: human serum albumen, bovine serum albumen,
      polyethylene glycol
```

```
-continued

<400> SEQUENCE: 34

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Ala Cys Asp Cys Arg
        35                  40                  45

Gly Asp Cys Phe Cys
    50

<210> SEQ ID NO 35
<211> LENGTH: 6
<212> TYPE: PRT
<213> ORGANISM: Artificial Sequence
<220> FEATURE:
<223> OTHER INFORMATION: integrin recognization sequence

<400> SEQUENCE: 35

Gly Gly Gly Arg Gly Asp
1               5
```